US012594388B2

(12) United States Patent
Shahaf et al.

(10) Patent No.: US 12,594,388 B2
(45) Date of Patent: Apr. 7, 2026

(54) DEVICE TO DELIVER A PREDETERMINED AMOUNT OF A SUBSTANCE TO A NATURAL ORIFICE OF THE BODY

(71) Applicant: SipNose Ltd., Yokne'am Ilit (IL)

(72) Inventors: Daniel Shahaf, M.P. Emek Ha-Yarden (IL); Iris Shichor, Zichron Yaakov (IL)

(73) Assignee: AptarGroup, Inc., Crystal Lake, IL (US)

( * ) Notice: Subject to any disclaimer, the term of this patent is extended or adjusted under 35 U.S.C. 154(b) by 933 days.

(21) Appl. No.: 17/834,303

(22) Filed: Jun. 7, 2022

(65) Prior Publication Data

US 2022/0409830 A1     Dec. 29, 2022

Related U.S. Application Data

(63) Continuation-in-part of application No. 14/433,048, filed as application No. PCT/IL2014/050752 on Aug. 21, 2014, now Pat. No. 11,383,048.
(Continued)

(30) Foreign Application Priority Data

Dec. 16, 2013     (DE) ........................... 2020131057150

(51) Int. Cl.
A61M 15/00     (2006.01)
A61M 11/00     (2006.01)
(52) U.S. Cl.
CPC ........ *A61M 15/009* (2013.01); *A61M 11/007* (2014.02); *A61M 15/0048* (2014.02)
(58) Field of Classification Search
CPC .............. A61M 15/009; A61M 11/007; A61M 15/0048; A61M 15/0003; A61M 15/0021;
(Continued)

(56) References Cited

U.S. PATENT DOCUMENTS 462,990 A     11/1891   Oppenheimer
3,921,637 A   11/1975   Bennie et al.
(Continued)

FOREIGN PATENT DOCUMENTS

CN     1981886     6/2007
CN     104520198   4/2015
(Continued)

OTHER PUBLICATIONS

Affidavit of Ms. Lia Kaufman dtd Aug. 3, 2020, pp. 1-9, with Facts and Arguments brief, published Aug. 7, 2020 in the Register of the Opposition proceedings in EP 3400047 B1, available at https://register.epo.org/application?number=EP17711702&Ing=en&tab=doclist (last accessed Nov. 9, 2023).
(Continued)

*Primary Examiner* — Elliot S Ruddie
(74) *Attorney, Agent, or Firm* — Foley & Lardner LLP

(57)     ABSTRACT

A device for delivering a predetermined amount of at least one substance to a body orifice of a subject includes a) a container for containing said at least one substance; b) a delivery end for placement in proximity to the orifice, the delivery end being in fluid communication with the container; c) a valve mechanically connectable to said container, characterized by at least two configurations: (i) an ACTIVE CONFIGURATION in which said valve enables delivery of predetermined amount of said substance from said container to said body orifice via said delivery end; and, (ii) an INACTIVE CONFIGURATION, in which said valve prevents delivery of said predetermined amount of said substance from said container to said body orifice; d) a trigger mechanism adapted to reconfigure said valve from said INACTIVE CONFIGURATION to said ACTIVE CONFIGURATION, and vice versa; and e) a fluid tight chamber.

28 Claims, 42 Drawing Sheets

Related U.S. Application Data

(60) Provisional application No. 61/868,614, filed on Aug. 22, 2013, provisional application No. 61/868,627, filed on Aug. 22, 2013.

(58) Field of Classification Search
CPC ............ A61M 15/003; A61M 15/0036; A61M 15/0041; A61M 2016/0027; A61M 2202/0225; A61M 15/0093; A61M 2205/583; A61M 15/08; A61M 2205/073; A61M 11/02; A61M 15/0025; A61M 2202/0208; A61M 2202/025; A61M 2202/0266; A61M 2202/0291; A61M 2205/3306; A61M 2205/3375; A61M 2205/581; A61M 2206/10; A61M 2209/045; A61M 2210/0618; A61M 2210/0625; A61M 2210/065; A61M 2210/0662; A61M 2210/1089; A61M 2210/1475; A61M 31/00; B05B 11/0027; B05B 11/0032; B05B 11/0054; B05B 11/061; B05B 11/062
See application file for complete search history.

(56) References Cited

U.S. PATENT DOCUMENTS

| | | | |
|---|---|---|---|
| 3,998,226 | A | 12/1976 | Harris |
| 4,017,007 | A | 4/1977 | Riccio |
| 4,114,615 | A | 9/1978 | Wetterlin |
| 4,620,670 | A | 11/1986 | Hughes |
| 5,048,729 | A | 9/1991 | Pritchard |
| 5,307,953 | A | 5/1994 | Regan |
| 5,740,794 | A | 4/1998 | Smith et al. |
| 6,123,228 | A | 9/2000 | Hippensteel |
| 6,135,979 | A | 10/2000 | Weston |
| 6,186,141 | B1 | 2/2001 | Pike et al. |
| 6,398,074 | B1 | 6/2002 | Bruna et al. |
| 6,708,846 | B1 | 3/2004 | Fuchs et al. |
| 6,971,385 | B1 | 12/2005 | Flora |
| 7,497,390 | B2 | 3/2009 | Beller |
| 7,726,308 | B1 | 6/2010 | Flora |
| 7,802,569 | B2 | 9/2010 | Yeates et al. |
| 7,900,659 | B2 | 3/2011 | Whitley et al. |
| 8,360,056 | B2 | 1/2013 | Ishizeki et al. |
| 2001/0008637 | A1 | 7/2001 | Hochrainer et al. |
| 2002/0023641 | A1 | 2/2002 | Stadelhofer |
| 2002/0092520 | A1* | 7/2002 | Casper ............. A61M 15/0081 128/200.22 |
| 2002/0092521 | A1 | 7/2002 | Sullivan et al. |
| 2002/0092524 | A1 | 7/2002 | Lockhart et al. |
| 2002/0174865 | A1 | 11/2002 | Gatton et al. |
| 2003/0015191 | A1 | 1/2003 | Armstrong et al. |
| 2003/0079743 | A1 | 5/2003 | Genova et al. |
| 2003/0127533 | A1 | 7/2003 | Stihl |
| 2003/0181917 | A1 | 9/2003 | Gertner |
| 2003/0187404 | A1 | 10/2003 | Waldenburg |
| 2003/0209455 | A1 | 11/2003 | Pynson et al. |
| 2004/0050885 | A1 | 3/2004 | Stradella |
| 2004/0153033 | A1 | 8/2004 | Mazzoni |
| 2005/0028812 | A1 | 2/2005 | Djupesland |
| 2005/0131357 | A1 | 6/2005 | Denton et al. |
| 2005/0188985 | A1 | 9/2005 | Sullivan et al. |
| 2006/0067911 | A1 | 3/2006 | Nilsson et al. |
| 2006/0107957 | A1 | 5/2006 | Djupesland |
| 2006/0151629 | A1 | 7/2006 | Vedrine et al. |
| 2006/0213514 | A1 | 9/2006 | Price et al. |
| 2006/0254583 | A1 | 11/2006 | Deboeck et al. |
| 2006/0254585 | A1 | 11/2006 | Ishizeki et al. |
| 2007/0051362 | A1 | 3/2007 | Sullivan et al. |
| 2007/0060868 | A1 | 3/2007 | Tsutsui |
| 2007/0125371 | A1 | 6/2007 | Djupesland |
| 2007/0151562 | A1 | 7/2007 | Jones et al. |
| 2007/0154407 | A1 | 7/2007 | Peters et al. |
| 2007/0256688 | A1 | 11/2007 | Schuster et al. |

| | | | |
|---|---|---|---|
| 2008/0029084 | A1 | 2/2008 | Costantino et al. |
| 2008/0092887 | A1 | 4/2008 | Hodson et al. |
| 2008/0210229 | A1 | 9/2008 | Corbacho |
| 2009/0166379 | A1 | 7/2009 | Wright et al. |
| 2009/0275668 | A1 | 11/2009 | Kamishita |
| 2009/0285849 | A1 | 11/2009 | Barsanti et al. |
| 2009/0308388 | A1 | 12/2009 | Chawla |
| 2009/0314293 | A1 | 12/2009 | Djupesland |
| 2010/0083963 | A1 | 4/2010 | Wharton et al. |
| 2010/0258115 | A1 | 10/2010 | Kawamura et al. |
| 2010/0282246 | A1* | 11/2010 | Djupesland ........... A61M 15/08 128/200.14 |
| 2010/0331765 | A1 | 12/2010 | Sullivan et al. |
| 2011/0048414 | A1* | 3/2011 | Hoekman ............. A61M 31/00 128/200.23 |
| 2011/0088690 | A1 | 4/2011 | Djupesland et al. |
| 2011/0168172 | A1* | 7/2011 | Patton ............... A61M 15/0028 128/200.23 |
| 2011/0283996 | A1 | 11/2011 | Abrams |
| 2012/0291779 | A1 | 11/2012 | Haartsen et al. |
| 2013/0096495 | A1 | 4/2013 | Holmqvist et al. |
| 2013/0180524 | A1 | 7/2013 | Shahaf et al. |
| 2013/0239964 | A1 | 9/2013 | Young et al. |
| 2013/0267864 | A1 | 10/2013 | Addington et al. |
| 2013/0299607 | A1 | 11/2013 | Wilkerson et al. |
| 2013/0345673 | A1 | 12/2013 | Ferreri et al. |
| 2014/0060532 | A1 | 3/2014 | Hodges et al. |
| 2015/0122257 | A1 | 5/2015 | Winkler et al. |
| 2015/0144129 | A1 | 5/2015 | Djupesland et al. |
| 2015/0165136 | A1 | 6/2015 | Galgon et al. |
| 2015/0174343 | A1 | 6/2015 | Muellinger et al. |
| 2015/0209325 | A1 | 7/2015 | Najarian et al. |
| 2015/0258287 | A1 | 9/2015 | Shahaf et al. |
| 2015/0297845 | A1 | 10/2015 | Shahaf et al. |
| 2016/0101245 | A1 | 4/2016 | Hoekman et al. |
| 2016/0101246 | A1 | 4/2016 | Dennis et al. |
| 2016/0129205 | A1 | 5/2016 | Shahaf et al. |
| 2018/0072480 | A1 | 3/2018 | Genosar |
| 2018/0110922 | A1 | 4/2018 | Dunki-Jacobs et al. |
| 2018/0344950 | A1 | 12/2018 | Goumeniouk et al. |
| 2019/0015613 | A1 | 1/2019 | Shahaf et al. |
| 2019/0060168 | A1 | 2/2019 | Koska |
| 2020/0197631 | A1 | 6/2020 | Stedman et al. |
| 2020/0197633 | A1 | 6/2020 | Shahaf et al. |
| 2020/0289768 | A1 | 9/2020 | Shahaf et al. |
| 2020/0289769 | A1* | 9/2020 | Poullain ........... A61M 15/0041 |
| 2020/0306463 | A1 | 10/2020 | Shahaf et al. |
| 2020/0398006 | A1 | 12/2020 | Clark et al. |

FOREIGN PATENT DOCUMENTS

| | | |
|---|---|---|
| CN | 107580513 | 1/2018 |
| DE | 19502725 | 8/1996 |
| DE | 19708406 | 9/1998 |
| DE | 20 2013 105 715 U1 | 2/2014 |
| EP | 1 023 098 B1 | 9/2004 |
| EP | 1 752 176 A1 | 2/2007 |
| EP | 2 002 856 A1 | 12/2008 |
| EP | 2 030 645 A1 | 3/2009 |
| EP | 2 922 770 | 9/2015 |
| GB | 0 724 974 A | 2/1955 |
| GB | 2 415 376 A | 12/2005 |
| JP | 2002-505981 A | 2/2002 |
| WO | WO-90/12567 A1 | 11/1990 |
| WO | WO-02/505981 | 9/1999 |
| WO | WO-99/46055 | 9/1999 |
| WO | WO-99/46055 A1 | 9/1999 |
| WO | WO-99/58180 | 11/1999 |
| WO | WO-02/055133 A2 | 7/2002 |
| WO | WO-02/060517 A2 | 8/2002 |
| WO | WO-2009/002267 | 12/2008 |
| WO | WO-2012/029064 A1 | 3/2012 |
| WO | WO-2012/105236 A1 | 8/2012 |
| WO | WO-2013/128447 A1 | 9/2013 |
| WO | WO-2015/025324 A1 | 2/2015 |
| WO | WO-2016/054742 | 4/2016 |
| WO | WO-2016/071914 A1 | 5/2016 |
| WO | WO-2016/199135 A1 | 12/2016 |
| WO | WO-2018/051371 | 3/2018 |

(56) References Cited

FOREIGN PATENT DOCUMENTS

| WO | WO-2019/003216 A1 | 1/2019 |
| WO | WO-2019/073165 | 4/2019 |
| WO | WO-2019/079335 A1 | 4/2019 |
| WO | WO-2019/220443 A1 | 11/2019 |
| WO | WO-2020/154182 | 7/2020 |

OTHER PUBLICATIONS

Pharmaseed Ltd., Author: N/A, Title: Brain and Blood PK Profile Following Intranasal Topirmate Administration—Comparison Between SipNose and Other Nasal Devices ("Pharmaseed"), pp. 1-43, with Petition in response to Patentee's observations (62 pages total), published Mar. 4, 2021 in the Register of the Opposition proceedings in EP 3400047 B1, available at https://register.epo.org/application?number=EP17711702&Ing=en&tab=doclistÐdocument E16) (last accessed Nov. 9, 2023).

SipNose, Author: N/A, Title: Preclinical Device S1A2NP8 Batch Release Form ("SipNose"), pp. 1-2, with Petition (21 pages total), published Mar. 4, 2021 in the Register of the Opposition proceedings in EP 3400047 B1, available at https://register.epo.org/application?number=EP17711702&Ing=en&tab=doclist (last accessed Nov. 9, 2023).

Supplemental European Search Report in EP 21764082 DTD Feb. 2, 2024.

Damm et al., "Intranasal Volume and Olfactory Function", Chemical Senses, 2002, pp. 831-839, vol. 27, Oxford University Press.

Derendorf et al., "Molecular and clinical pharmacology of intranasal corticosteroids: clinical and therapeutic implications", Allergy, 2008, pp. 1292-1300, vol. 63, 2008 Blackwell Munksgaard.

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

International Preliminary Report on Patentability for International Application No. PCT/IL2014/050752, dated Feb. 23, 2016.

International Search Report & International Written Opinion of the International Searching Authority issued in International Application No. PCT/IL2014/050752, dated Dec. 18, 2014.

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology-Lung Cellular and Molecular Physiology, 2016, pp. L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure over time", International Journal of Obesity, 2014, pp. 650-656, vol. 38, 2014 Macmillan Publishers Limited.

Scheibe et al., "Intranasal Administration of Drugs", Archives of Otolaryngology-Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

* cited by examiner

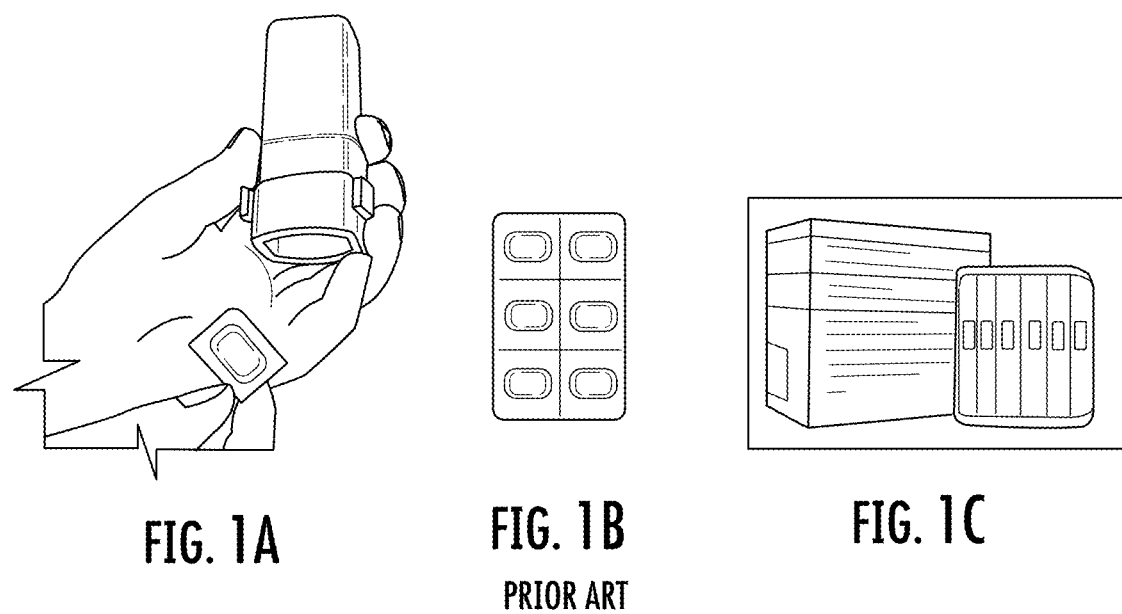
FIG. 1A          FIG. 1B          FIG. 1C
PRIOR ART
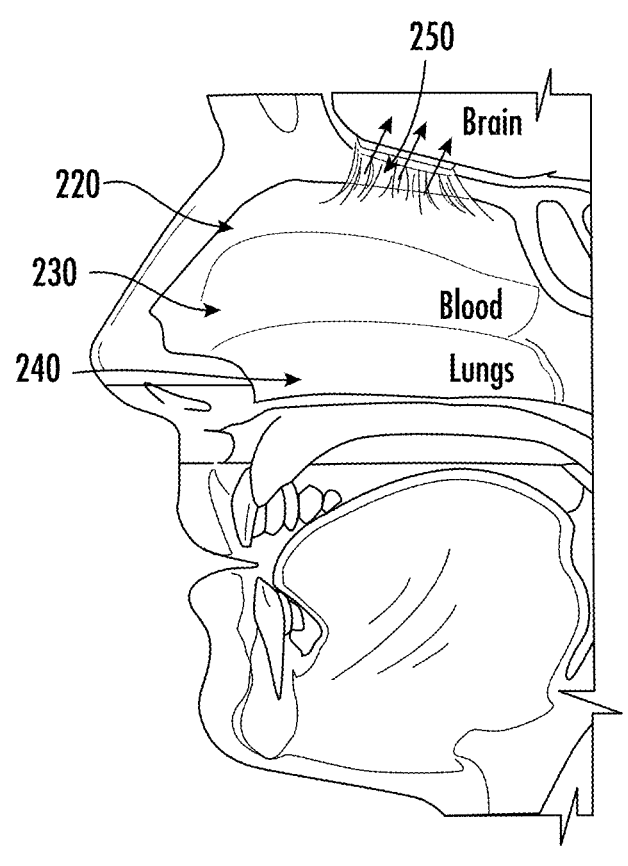
FIG. 2

Fig. 3A                    Fig. 3B

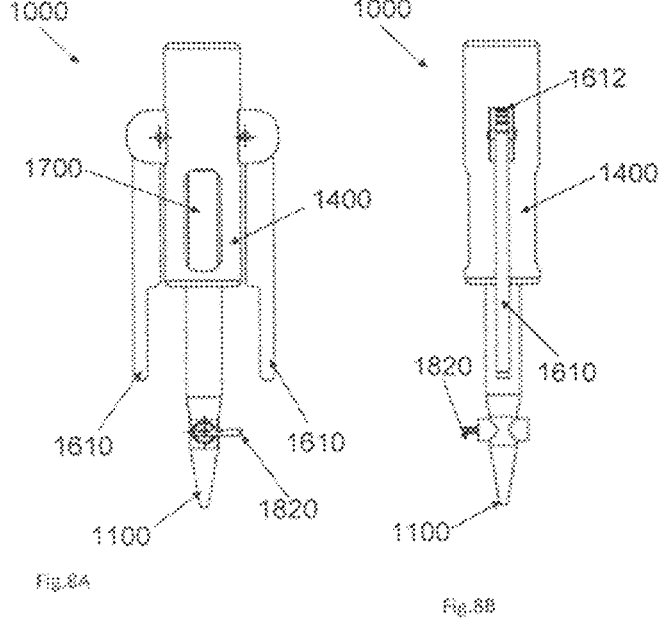
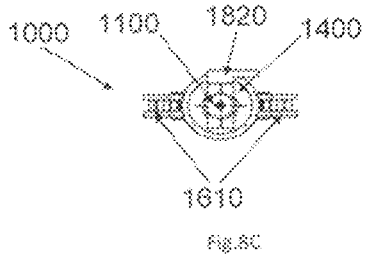

SECTION B-B

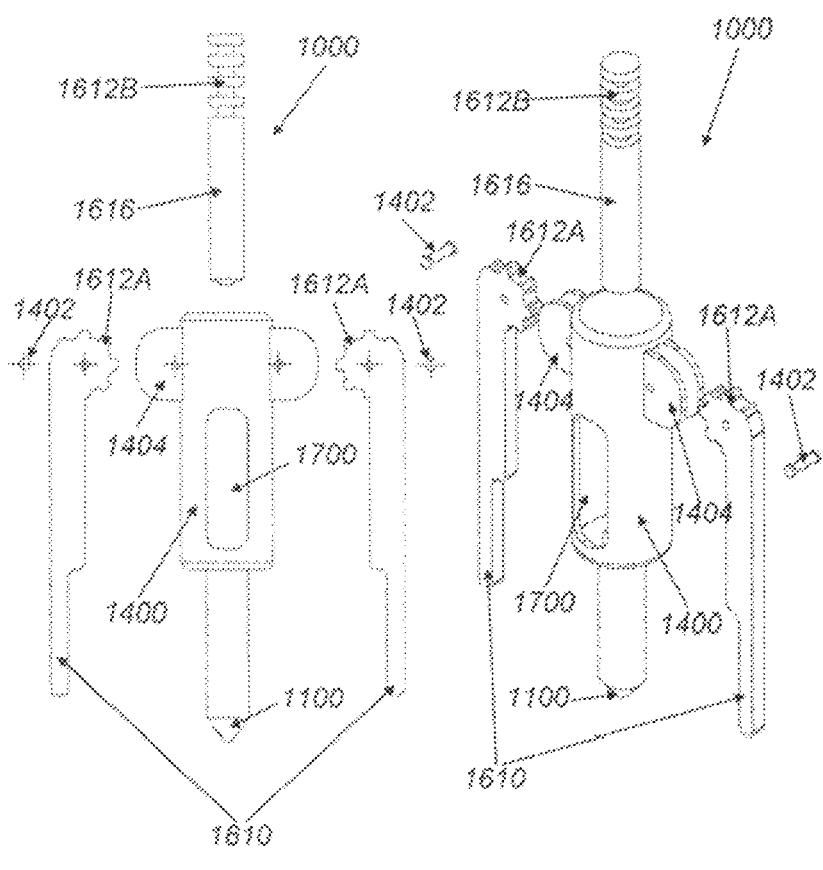
Fig.10A                              Fig.10B

SECTION A-A

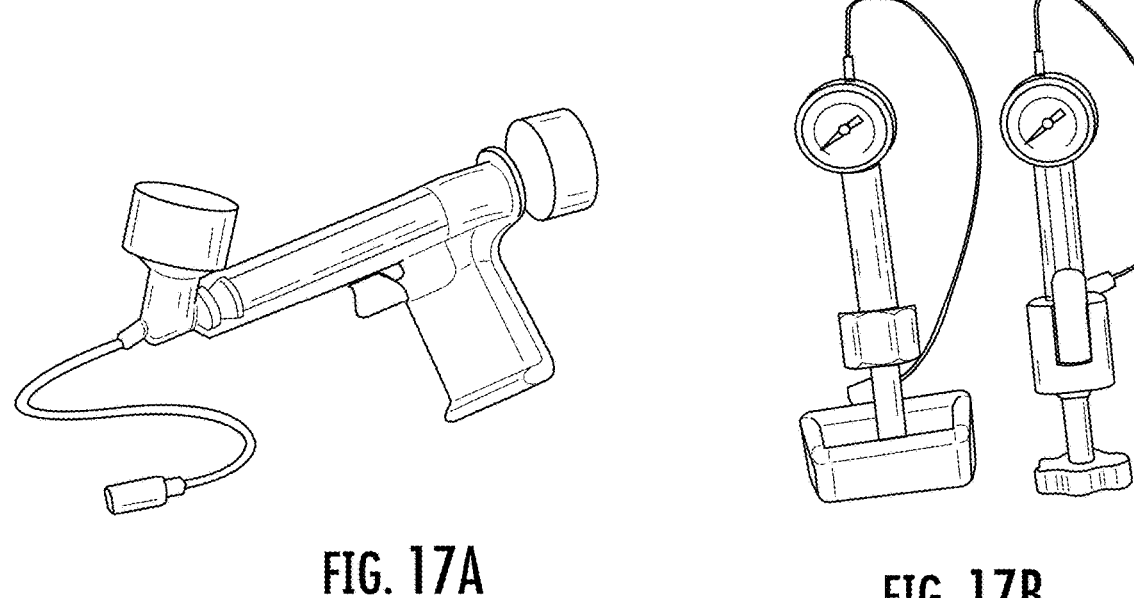
FIG. 17A
FIG. 17B
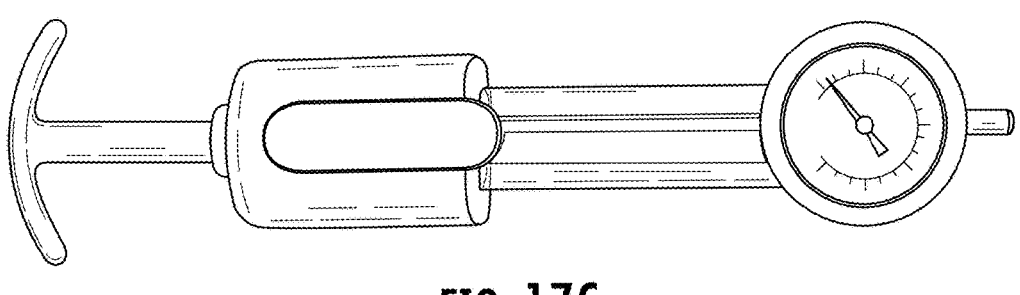
FIG. 17C

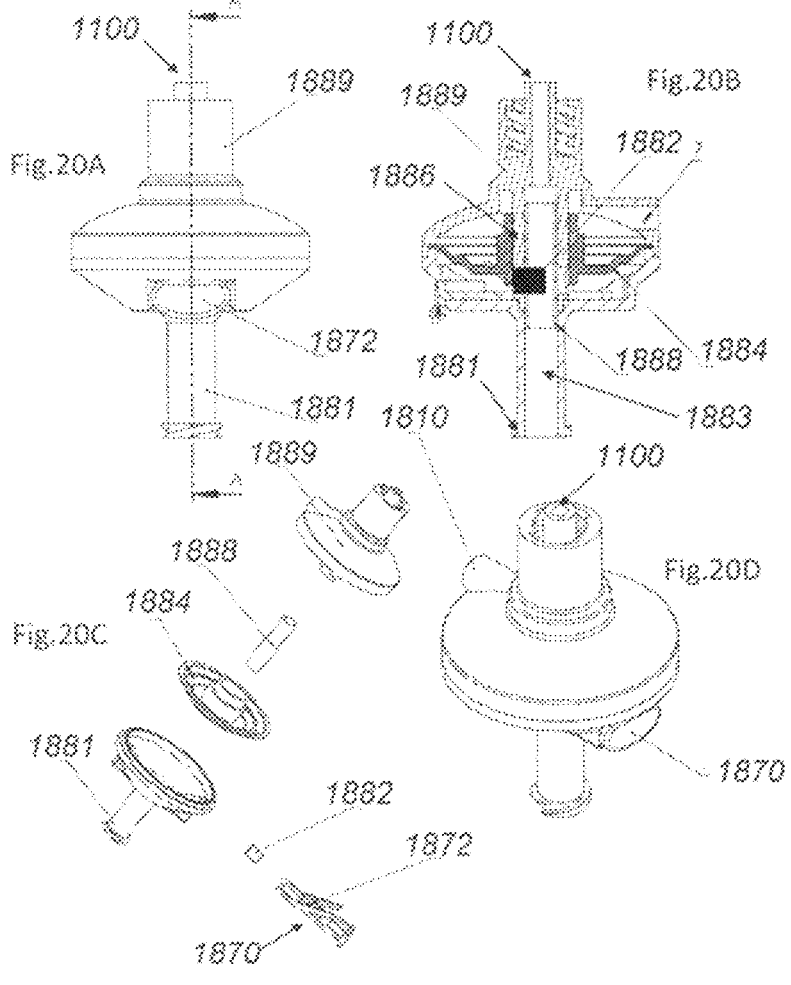

SECTION A-A

DETAIL C
SCALE 4 : 1

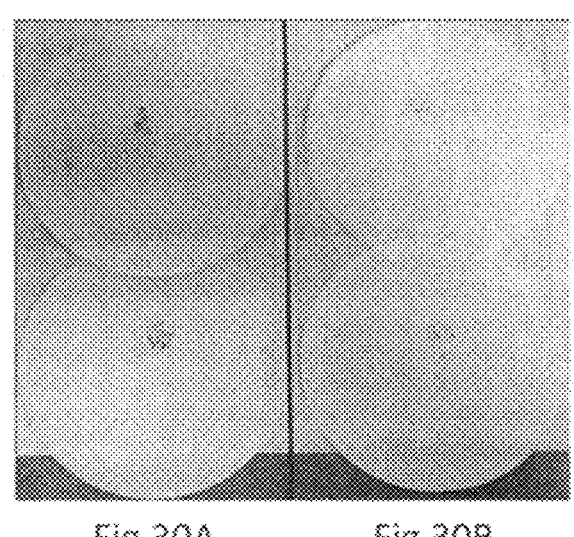
Fig.30A        Fig.30B
Fig.31A
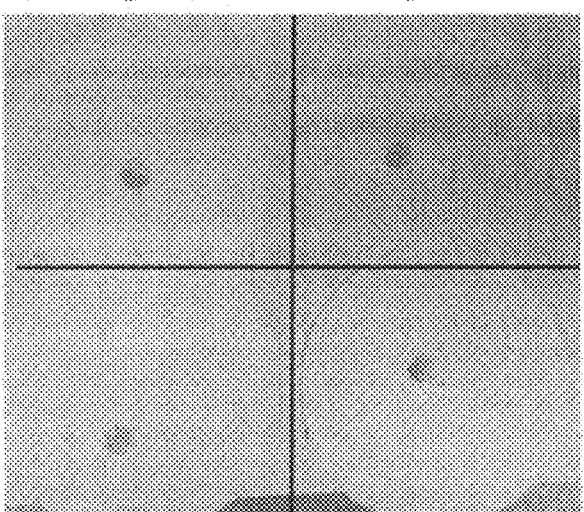
Fig.31C
Fig.31B
Fig. 31D

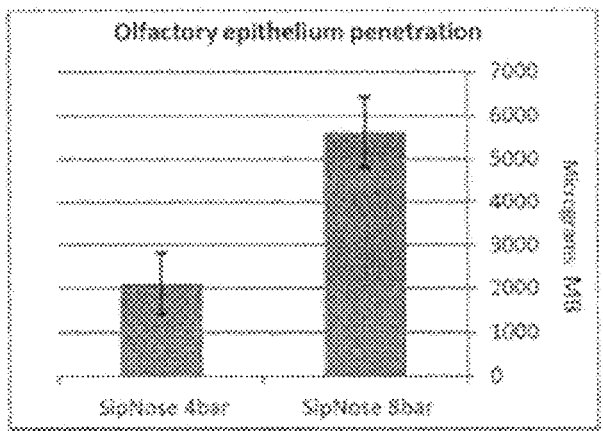
Fig. 32
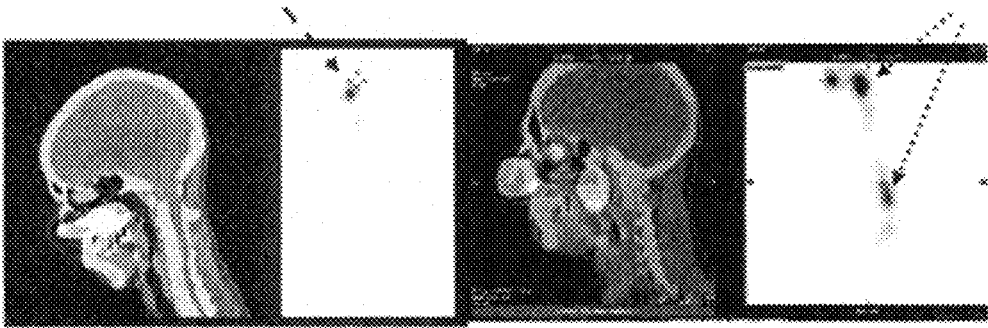
Fig. 33A                                    Fig. 33B

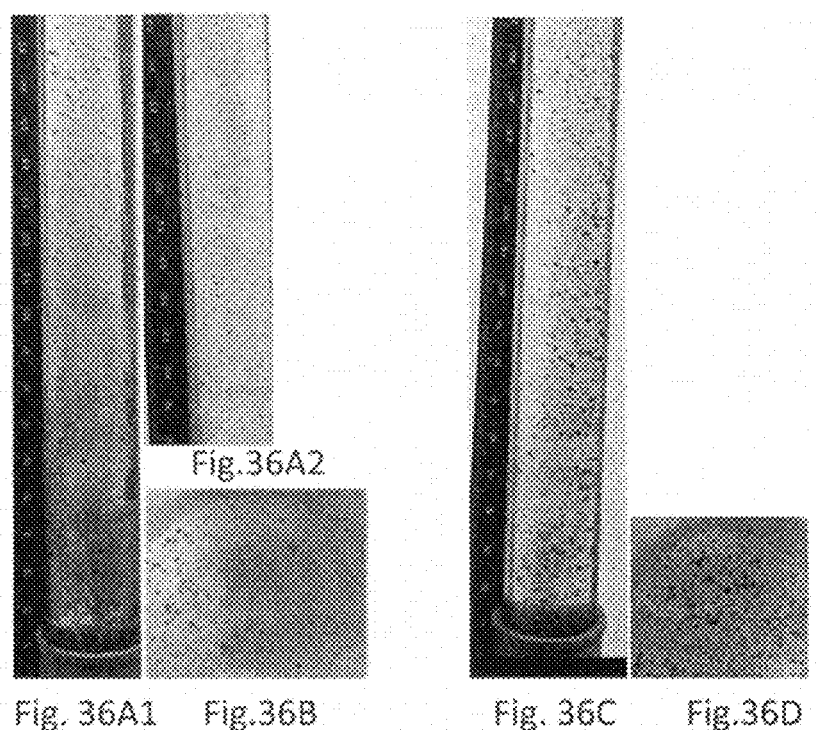
Fig.36A2
Fig. 36A1     Fig.36B     Fig. 36C     Fig.36D

1100

1620, 4

30

DEVICE TO DELIVER A PREDETERMINED AMOUNT OF A SUBSTANCE TO A NATURAL ORIFICE OF THE BODY

CROSS-REFERENCE TO RELATED APPLICATIONS

The present application is a continuation in part of U.S. application Ser. No. 14/433,048 filed on Apr. 2, 2015, which is a national stage of PCT/IL2014/050752 filed on Aug. 21, 2014, which claims priority to German Patent Application No. 2020131057150 filed on Dec. 16, 2013, and to U.S. Provisional Application No. 61/868,614 filed on Aug. 22, 2013 and U.S. Provisional Application No. 61/868,627 filed on Aug. 22, 2013, the entire contents of each of the foregoing being incorporated herein by reference.

FIELD OF THE INVENTION

The present invention generally pertains to a system for delivering a predetermined amount of a substance to a natural orifice of the body.

BACKGROUND OF THE INVENTION

Many devices of the prior art focus on a mechanism to allow better aerosol formation and better dispersion in the nasal cavity. Other mechanisms for better delivery focus on special formulations that include materials and structures to allow better absorption in the target tissue.

Each of these strategies has its advantages and disadvantages. For example, improvements to the delivery device can improve bringing the material to the desired area, but will neglect the need to enhance the absorption of the compound into and through the mucosal layer. On the other hand, improvements to the composition, the formulation or both can improve absorption into and through the mucosal layer, but may well neglect the difficulty of delivering a sufficient amount of the material to the desired tissue.

It is therefore a long felt need to provide a system for efficient delivery of a substance to a target site, in a manner that neglects neither the need to bring sufficient material to the target site, nor the need to ensure adequate absorption into and through the mucosal layer.

SUMMARY OF THE INVENTION

It is an object of the present invention to provide a device with capabilities of improving the transfer of medicament to the predetermined desired location. Furthermore, the present invention provides a device which improves the delivery of medicament through the tissue.

It is another object of the present invention to provide a system for delivering a predetermined amount of a substance or combination of substances into a natural orifice of the body for absorption in a target. Furthermore, the combination of the delivery device and the composition can have either an additive or a synergistic effect, where the additive or synergistic effect of the combination can improve the efficacy of the delivered substance, can improve the safety of the delivered substance, can alter a delay between dispensing and activation, can alter the duration of activation, can improve user compliance and any combination thereof.

It is further an object of the present invention to provide the system, wherein the active agent is selected from a group consisting of a peptide, a protein, an antibody, nucleic acid, a small molecule, a cell, a stem cell, a nanoscale particle, a microscale particle, a purified natural biologic, a synthetic biologic; and any combination thereof.

It is further an object of the present invention to provide the system, wherein at least one said substance comprises a member of a group consisting of a medicament, a carrier, a bulking agent, an inert material, a flavoring material, an odorizing material, an excipient and any combination thereof.

It is further an object of the present invention to provide the system, wherein said substance is selected from a group consisting of a gas, a liquid, a powder, an aerosol, a slurry, a gel, a suspension and any combination thereof.

It is further an object of the present invention to provide the system, wherein the substance comprises a penetration enhancer selected from a group consisting of a micro-emulsion, a nano-emulsion of the following: a surfactant, a part of a surfactant, an oil, a co-surfactant, an aqueous phase and any combination thereof; the penetration enhancer allowing: better absorption in the mucosal tissue, better permeation and absorption in the target cells, better stability of an encapsulated drug, better stability of an active ingredient and any combination thereof.

It is further an object of the present invention to provide the system, wherein the substance comprises a mucoadhesive agent such as, but not limited to, bioadhesive proteins, carbohydrates and mucoadhesive polymers It is another object of the present invention to provide a device for delivering a predetermined amount of at least one substance to a body orifice of a subject, the device comprising: (a) a container (also refers to as capsule) for containing at least one substance; (b) a delivery end for placement in proximity to the orifice, the delivery end being in fluid communication with the container; (c) a valve mechanically connectable to the container, characterized by at least two configurations: (i) an ACTIVE CONFIGURATION in which the valve enables delivery of a predetermined amount of the substance from the container to the body orifice via the delivery end; and, (ii) an INACTIVE CONFIGURATION, in which the valve prevents delivery of the predetermined amount of the substance from the container to the body orifice (d) a trigger mechanism adapted to reconfigure the valve from the ACTIVE CONFIGURATION to the INACTIVE CONFIGURATION, and vice versa; wherein the trigger mechanism is adapted to reconfigure the valve from the INACTIVE CONFIGURATION to the ACTIVE CONFIGURATION for a predetermined period of time in response to activation of the trigger mechanism; and (e) a fluid tight chamber adapted to contain predetermined amount of pressurized gas at a predetermined pressure; wherein the pressurized gas, once the valve is reconfigured from the INACTIVE CONFIGURATION to the ACTIVE CONFIGURATION, is adapted to entrain the substance and deliver the same to the body orifice.

It is another object of the present invention to provide a syringe like device for delivering a predetermined amount of at least one substance to a body orifice of a subject, the device characterized by a main longitudinal axis; the device comprising: (a) a delivery end for placement in proximity to the orifice; (b) a container for containing at least one substance; the container being in fluid communication with the delivery end; (c) a valve mechanically connectable to the container, characterized by at least two configurations: (i) an ACTIVE CONFIGURATION in which the valve enables delivery of predetermined amount of the substance from the container to the body orifice via the delivery end; and, (ii) an INACTIVE CONFIGURATION, in which the valve prevents delivery of the predetermined amount of substance from the container to the body orifice; (d) a trigger mechanism adapted to reconfigure the valve from the ACTIVE CONFIGURATION to the INACTIVE CONFIGURATION, and vice versa; wherein the trigger mechanism is adapted to reconfigure the valve from the INACTIVE CONFIGURATION to the ACTIVE CONFIGURATION for a predetermined period of time in response to activation of the trigger mechanism; (e) a fluid tight chamber adapted to contain predetermined amount of pressurized gas at a predetermined pressure, the fluid-tight chamber in fluid communication with the valve; and (f) a charging mechanism adapted to provide the predetermined amount of pressurized gas, the charging mechanism comprising a lever mechanism adapted to reversibly move a piston by a predetermined amount, a pump and any combination thereof; wherein the pressurized gas, once the valve is reconfigured from the INACTIVE CONFIGURATION to the ACTIVE CONFIGURATION, is adapted to entrain the substance and deliver the same to the body orifice.

It is another object of the present invention to provide the system or the syringe-like device, comprising a nozzle or delivery end.

It is another object of the present invention to provide the system or the syringe-like device, wherein the nozzle or delivery end comprises at least one said extension.

It is another object of the present invention to provide the system or the syringe-like device, wherein at least one said extension is adapted to ensure proper positioning of the delivery end in said nasal passage, said proper positioning selected from a group consisting of: delivery end centralized in a nasal passage, delivery end touching a predetermined portion of a nasal passage, delivery end close to a predetermined portion of a nasal passage, said extension seals an opening of a nasal passage so that material cannot escape therefrom, said extension seals a nasal passage so that substance does not contact undesired portions thereof, said extension seals a nasal passage so that substance remains in a predetermined portion thereof, said extension reduces the discomfort of contact between said delivery end and a nasal passage.

It is another object of the present invention to provide a capsule for containing at least one flowable substance, said capsule having a main longitudinal axis, said capsule comprising at least one compartment, said compartment adapted to contain said at least one flowable substance; wherein, during dispensing of said at least one flowable substance, a carrier gas passing through said capsule entrains said at least one flowable substance contained within said at least one compartment such that said at least one flowable substance has a predetermined distribution within said dispensed mixture.

It is another object of the present invention to provide a method for dispensing a flowable substance, comprising steps of:

a. providing a capsule for containing at least one flowable substance, said capsule having a main longitudinal axis, said capsule comprising at least one compartment, said compartment adapted to contain said at least one flowable sub stance;

b. emplacing said capsule within a delivery device; and c. activating said delivery device, said activation both (a) supplying a carrier gas and (b) opening said capsule, thereby dispensing said flowable substance by entraining said at least one flowable substance in said carrier gas such that said at least one flowable substance has a predetermined distribution within said dispensed mixture.

BRIEF DESCRIPTION OF THE FIGURES

In order to better understand the invention and its implementation in practice, a plurality of embodiments will now be described, by way of non-limiting example only, with reference to the accompanying drawings, wherein FIGS. 1A, 1B, and 1C illustrate capsules of the prior art;

FIG. 2 illustrates delivery sites in the human nasal passages;

FIGS. 3A-3B, 4A, 4B, 4C and 4D, 5A, 5B, 5C and 5D, 6, 7A, 7B, 7C and 7D, 8A, 8B and 8C, 9A, 9B, 9C and 9D, 10A-10B, 11A, 11B, 11C, 11D, 11E and 11F, 12A-12B, 13A, 13B and 13C, 14, 15A-15B and 16A, 16B, 16C and 16D schematically illustrate embodiments of devices to deliver a predetermined amount of a substance to a natural orifice of the body;

FIGS. 17A, 17B and 17C illustrate devices for simultaneously measuring pressure and volume;

FIGS. 18A, 18B, 18C and 18D, 19A, 19B, 19C and 19D and 20A, 20B, 20C and 20D schematically illustrate embodiments of triggering mechanisms;

FIGS. 28A-28B, 29A-29B, 30A-30B, 31A, 31B, 31C and 31D, 32, 33A-33B, 34A, 34B and 34C, 35A, 35B, 35C and 35D, 36A1, 36A2, 36B, 36C and 36D and 37A, 37B, 37C and 37D display experimental results of various tests.

DETAILED DESCRIPTION OF THE PREFERRED EMBODIMENTS

Figure 3:
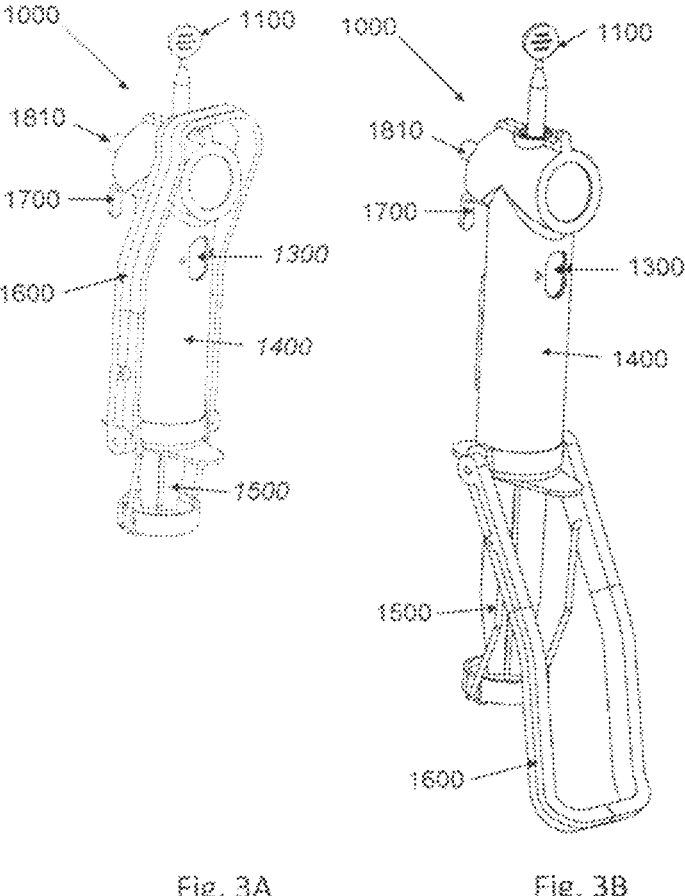
Figure 4:
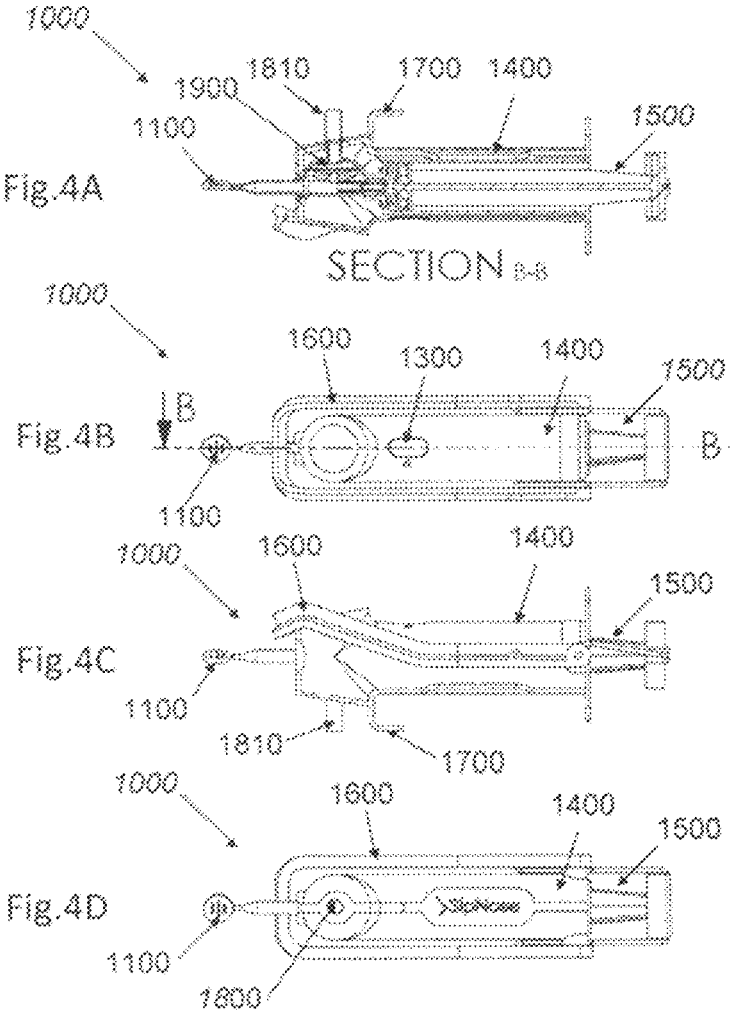
Figure 5:
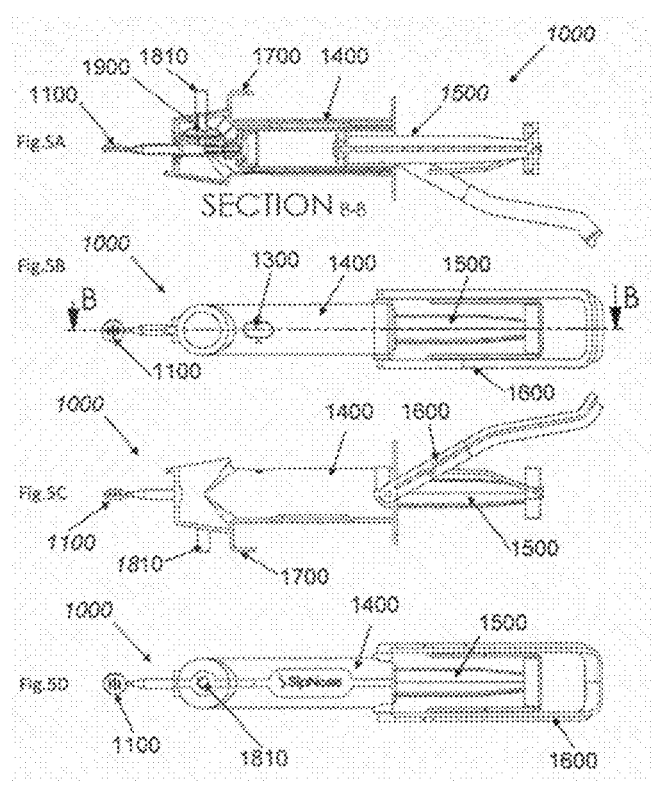

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means delivering a predetermined amount of a substance to a natural orifice of the body.

The term 'capsule' or 'container' hereinafter refers to a container adapted to contain a flowable substance. The term flowable refers hereinafter to any liquid, gas, aerosol, powder and any combination thereof.

The term 'plurality' hereinafter refers to an integer greater than or equal to one.

The term 'olfactory epithelium' hereinafter refers to a specialized epithelial tissue inside the nasal cavity. The olfactory epithelium lies in the upper top portion of the nasal cavity.

The term 'substance' hereinafter refers to any substance capable of flowing. Such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon and xenon. Devices charged by hand will normally use air as the carrier gas.

The term 'channel' hereinafter refers to a passageway allowing passage of a fluid through at least a portion of a mixing mechanism. The channel can be disposed within a portion of the mixing mechanism, forming a closed bore; it can be on an exterior of a portion of the mixing mechanism, forming a groove on the portion of the mixing mechanism, and any combination thereof.

The term 'about' refers hereinafter to a range of 25% below or above the referred value.

The term 'biologic' or 'biologic response modifier' hereinafter refers to material manufactured in or extracted from biological sources such as a genetically engineered protein derived from human genes, or a biologically effective combination of such proteins.

In all of the embodiments of the device shown hereinbelow, identical numbers refer to identical functions.

All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the vagina, the rectum and any combination thereof.

In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells and any combination thereof.

However, it should be emphasized that the device can be provided alone as well as in combination with a capsule.

In some cases the capsule would be provided with a known medicament within the same and in another cases the capsule would be 'filled' with the medicament just before use.

In some embodiments of the present invention, the device operating characteristics and the substance characteristics can be jointly tailored to maximize uptake of the substance at the desired site. In preferred variants of such embodiments, uptake is further enhanced by exploiting synergies between delivery characteristics generated by the device and by the formulation or composition of the delivered material In some embodiments, the substance comprises one or more agents to enhance delivery through the mucosal membrane by means of mucoadhesive agent and/or a permeability enhancer agent and/or a particulate formulation in the nano-particle or macro-particle range, and any combination thereof. In such embodiments, the combination of the device and substance enhance the delivery of the active agent to the target tissue (nasal epithelium and more specifically olfactory epithelium).

A non-limiting example is a composition comprising a drug to be delivered and at least one chemical permeation enhancer (CPE). In a preferred embodiment, the composition contains two or more CPEs which, by using a nasal delivery device, affect in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucus membrane.

In contrast to prior-art nasal delivery devices and technologies, the devices of the present invention can produce a fine aerosol in the nasal cavity or other desired body orifice at the target area and at the location of the target tissue instead of within the device or immediately after exit from the device. Utilizing the pressure as a driving force and the air as a carrier allows the material to be released from the nozzle in a pre-aerosolized state. The properties of the resultant aerosol are typically dependent on the properties of the device and of the medium into which the device is discharged. The properties of the device which affect the aerosol characteristics are the delivery pressure, the volume of the delivery gas, and the characteristics of its orifice.

In some embodiments, the aerosol properties are fairly independent of the delivered substance, in other embodiments, the pressure, volume, orifice characteristics, and delivered substance properties can be co-optimized.

In prior-art devices the aerosol is produced at the immediate exit from the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the orifice, such as the turbinates of the nose.

In contrast, in the present device, the pre-aerosolized mixture of gas and substance exits the device with a significant driving force as a mixture of aerosol and pre-aerolized material (fluid or powder). When the preaerosolized material hits the walls of the nasal passages, it "explodes" into a fine aerosol that is capable of being driven by the pressure deep into the nasal passages to deposit in the desired region.

FIGS. 1A-1C illustrate capsules of prior art intended to deliver medicaments to the nasal passages. FIGS. 1A and 1B comprise frangible capsules containing a single medicament. In use, the use breaks the capsule by pressure on a mechanism comprising part of the delivery device, and mixing of the contents of the capsule and air occurs when the patient inhales. FIG. 1C comprises a vial; the top of the vial is broken to deliver the medication.

In these typical prior art devices, if more than one substance is to be delivered, the substances will mix in the capsule or vial during storage and prior to delivery. Reactions can occur between the various components, limiting storage time and possibly requiring inconvenient storage conditions, such as keeping the capsules in a refrigerator before use.

The pressure to deliver the substance is the pressure of inhalation, which is quite variable, both between patients and between different inhalations by the same patient.

FIG. 2 illustrates locations for deposition of substances entering the nostrils. Typical locations are (a) deposition in the lungs after passage through the lower turbinates (240), thereby enabling transfer of the substance across the walls of the alveoli of the lungs; (b) deposition in the mucous membranes lining the nasal passages, especially the lower (240), and middle (230) turbinates, facilitating transfer of the substance to the blood; and (c) deposition in the olfactory mucous membranes of the upper turbinates (220) facilitating transfer, via the thin ethmoid bone (not shown) to the brain.

FIGS. 3A, 3B, 4A, 4B, 4C, 4D, 5A, 5B, 5C and 5D illustrate an embodiment of the device (1000). FIG. 3A shows the device (1000) in a closed position, while FIG. 3B shows the device (1000) in an open position. The device (1000) comprises a container for the medication (not shown); a delivery end (1100) in fluid communication with the container, the delivery end (1100) placeable in proximity to an orifice, which includes both within the nostril and close to it; a valve (not shown) for controlling the release of the substance from the device via the delivery end (1100); and a trigger mechanism (1810) to activate the valve and cause release of the substance to the body orifice.

The embodiment of FIGS. 3A-5D further comprises a chamber (1400) adapted to contain a predetermined amount of air and to pressurize the air.

In this embodiment, the chamber wall also comprises an indicator window (1300), so that the user has a visual indication that the device is properly charged before triggering and that the device is properly discharged after triggering.

An indicator can provide an indication to the user of at least one of the following (a) that the substance is entrained within the enclosed air; (b) transport of the substance from the container to the nasal passages has been successful; (c) the predetermined amount of pressurized gas is at the predetermined pressure, and any combination thereof.

The indication can be a visual indication such as a change of color, an audible predetermined sound pattern and any combination thereof.

In the embodiment of FIGS. 3A-5D, charging of the device is by means of a lever (1600) and piston (1500). The piston is in slidable, fluid-tight communication with the inner wall of the chamber (1400). The lever is rotatably connected to the chamber (1400) and is connected to the piston (1500) so that rotation of the lever slides the piston (1500) in and out of the chamber (1400).

The device comprises at least one valve. The valve allows entry of air into the chamber (1400) at all times, but air cannot exit the chamber (1400) until the valve is triggered.

To charge the device, the handle (1600) is rotated outward and downward from the position in FIG. 3A to the position in FIG. 3B, thus sliding the piston (1500) partially out of the barrel (1400) and causing air to enter the device. Rotation of the handle (1600) inward and upward from the position of FIG. 3B to the position of FIG. 3A compresses the air in the barrel (1400).

The device is now in the activated configuration.

In the embodiment (1000) of FIGS. 3A-5D, the device is adapted to discharge the substance into a nostril and the triggering mechanism comprises an air-intake activator (1900). The user places the delivery end (1100) in proximity to a nostril and places the air intake nozzle (1810) in the mouth. The user then sucks on the air intake nozzle, which opens a delivery valve (not shown), and activates the device, allowing release of the compressed gas and transitioning the device to the inactivated configuration. The compressed gas entrains the stored substance, thereby delivering the stored substance to the nostril. The device can be activated using suction; however, as will be appreciated hereinbelow, any other activator known in the art is within the scope of the invention (e.g., a mechanical trigger, an electrical trigger, a voice trigger, an air inhalation trigger, a sucking trigger, as disclosed above, and any combination thereof). An exemplary embodiment of a mechanical trigger, disclosed below, is activated by a pressable button.

It should be noted that, in preferred embodiments, the pressurized and predetermined amount of compressed gas is inert and will not react with the substance.

In this embodiment, the device comprises an optional grip handle (1700), which can be seen below the air intake nozzle (1810). It provides the user a better grip on the device.

The embodiments disclosed in FIGS. 3A-16C and 24 are typically configurable into four states: (a) a non-activated state where the valve is in its INACTIVE CONFIGURATION, the chamber contains non-pressurized gas, and the portion of the chamber in fluid connection with the valve is at a minimum, (b) a pre-activated state where the valve is in its INACTIVE CONFIGURATION, the chamber contains non-pressurized gas, and the portion of the chamber in fluid connection with the valve is at a maximum (see FIG. 3B), in this stage the tip to be entered to the body orifice (the delivery end) can be under "vacuum" conditions or not, (c) a loaded configuration where the chamber contains a predetermined amount of pressurized gas and the valve is in its INACTIVE state, and (d) an activated state where the valve is in its ACTIVE state. Typically, the activated state discharges the device, with the mixture of gas and substance entering the body orifice via the delivery end.

The characteristics of the aerosol depend on the delivery pressure, the volume of air delivered and the characteristics of the orifice, namely its size and shape. The delivery pressure and the volume of air delivered depend on the pressure of the gas in the chamber in the loaded state, on the volume of the chamber in the loaded state, and on the characteristics of the fluid connection between the chamber and the delivery orifice. The less change there is in these characteristics during an activation and between activations, the more reliable and the more reproducible the device will be. Therefore, in controlling the characteristics of the fluid connection, the time taken to open the valve needs to be taken into consideration. In devices of the current invention, the valve opening times are both reproducible and short and are not in any way dependent on the user, so that the delivery comprises a short, reproducible, high pressure pulse of the gas.

The non-activated state and the loaded state appear identical; they differ in that, in the loaded state the chamber contains pressurized gas whereas, in the non-activated state, the chamber does not contain pressurized gas.

In some embodiments, intended for use in emergencies, the device is a single-use device with only two states, a loaded state and an activated state. The device is provided in the loaded state; activation of the trigger mechanism discharges the gas and substance.

In other emergency-use embodiments, the device is provided in the pre-activated state. The user transforms the device into the loaded state, pressurizing the gas, and activates the trigger mechanism to discharge the gas and substance.

FIG. 4A shows a cross-section of the embodiment (1000) of FIGS. 3A-3B, while FIGS. 4B, 4C and 4D show, respectively, a front view (FIG. 4B), a side view (FIG. 4C) and a bottom view (FIG. 4D) of the embodiment of the device of FIGS. 3A-3B.

In FIGS. 4A,4B, 4C and 4D, the delivery end (1100) is at the left and the piston (1500) at the right. The handle (1600) is shown in the closed position, with the piston (1500) withdrawn within the barrel (1400) to its fullest extent.

FIG. 4B shows a front view of the embodiment (1000). The indicator window (1300) is visible. The cross-section of FIG. 4A is taken along the line BB shown in FIG. 4B.

The cross-section of FIG. 4A shows the delivery end (1100) at the left, the air intake activator (1900) and the air intake nozzle (1810) which enables triggering of the air intake activator (1900), grip handle (1700), and the piston (1500) fitting snugly and slidably in the barrel (1400).

FIG. 4C shows a side view of the embodiment (1000). The delivery end (1100) is shown at the left. The handle (1600) is shown in the closed position. The air intake nozzle (1810) is at the bottom, as is the grip handle (1700). The piston (1500) is shown at the right, in its fully-retracted position in the barrel (1400).

FIG. 4D shows a bottom view of the embodiment (1000), with delivery end (1100) at the left. The air intake nozzle (1810) is in the front of the view. The handle (1600) is shown in the closed position. The piston (1500) is shown at the right, in its fully-retracted position in the barrel (1400).

FIGS. 5A, 5B, 5C, and 5D shows the embodiment (1000) of FIGS. 3A-3B and 4A, 4B, 4C, and 4D with the handle (1600) in the pre-activated configuration so that the piston (1500) is in its fully-extended position in the barrel (1400), such that predetermined amount of air has entered the barrel (1400) but before the air is compressed by rotation of the handle (1600) and retraction of the piston (1500) into the barrel (1400).

FIG. 5A shows a cross-section of the embodiment (1000) of FIGS. 3A-3B, while FIGS. 5B, 5C, and 5D show, respectively, a front view (FIG. 5B), a side view (FIG. 5C) and a bottom view (FIG. 5D) of the embodiment of the device of FIGS. 3A-3B. The numbers in FIGS. 5A-5D refer to parts identical to those described above in FIGS. 4A-D.

Figure 6:
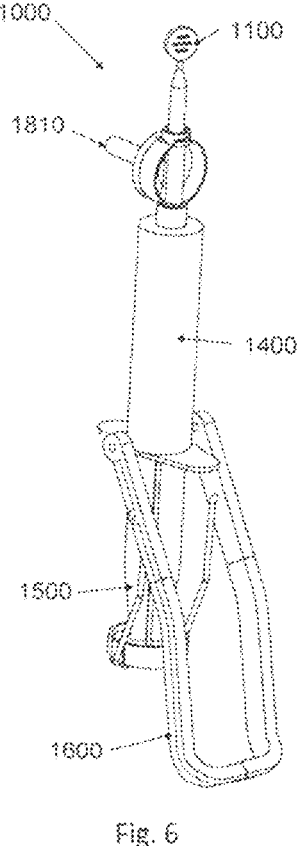
Figures 7A, 7B, 7C, 7D:
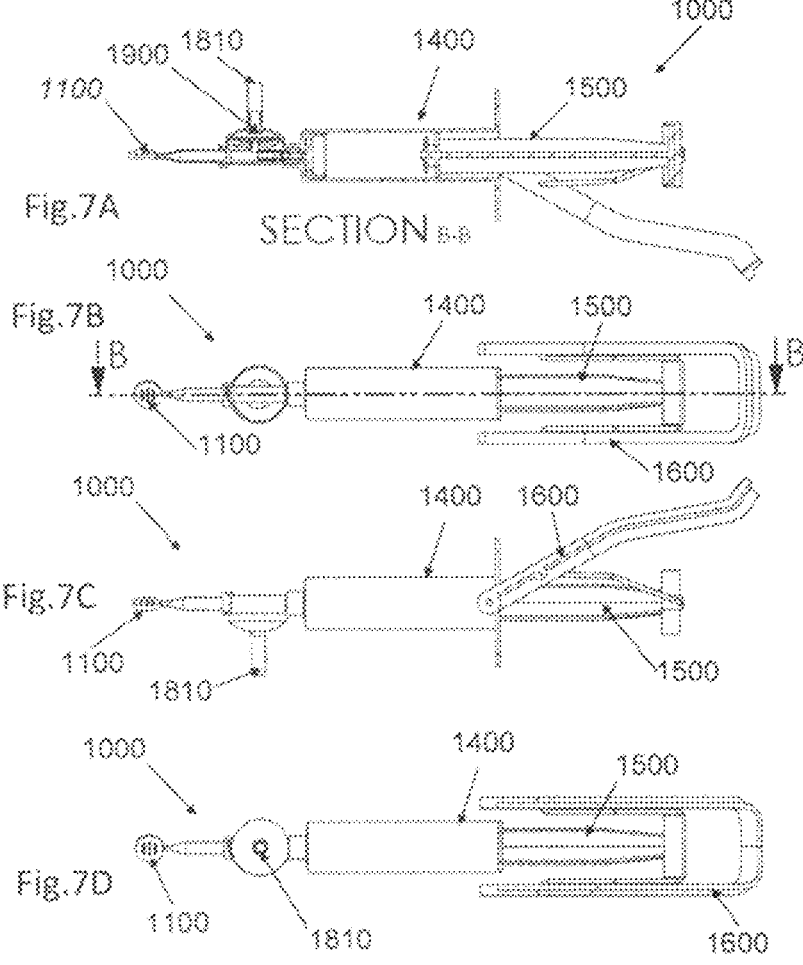

FIGS. 6-7D show another embodiment (1000) of a device with an air-intake activator (1900, not shown). The device of FIGS. 6-7D is identical to the device of FIGS. 3A-5D, except for the shape of the device in the region of the air intake nozzle (1810) and, as in the device of FIGS. 3A-5D, the user places the delivery end (1100) in proximity to a nostril, places the air intake nozzle (1810) in the mouth and sucks on the air intake nozzle to deliver the stored substance to the nostril.

FIGS. 6 and 7D show the embodiment in the open position, as described above for FIGS. 5A-5D.

FIG. 7A shows a cross-section of the embodiment (1000) of FIG. 6, while FIGS. 7B-7D show, respectively, a front view (FIG. 7B), a side view (FIG. 7C) and a bottom view (FIG. 7D) of the embodiment of the device of FIG. 6. The numbers in FIGS. 7A-7D refer to parts identical to those described above in FIGS. 3A-5D.

FIGS. 8A-8C and 10A-10B show an embodiment of the device with a two-lever charging mechanism (1610). The embodiment illustrated in FIGS. 8A-8C includes a stopcock trigger (1820) while, in FIGS. 9A-9D and 10A-10B, the activator is not shown, to illustrate the two-lever charging mechanism (1610) more clearly. The numbers in FIGS. 8-10 refer to parts substantially the same as those described above in FIGS. 3A-5D, except that the handle (1600) has been replaced by the two-lever charging mechanism (1610). A variant of the stopcock trigger (1820) is shown in FIG. 8A-8C, and no activator is shown in FIGS. 9A-9D or 10A-10B.

Figures 9A, 9B, 9C, 9D:
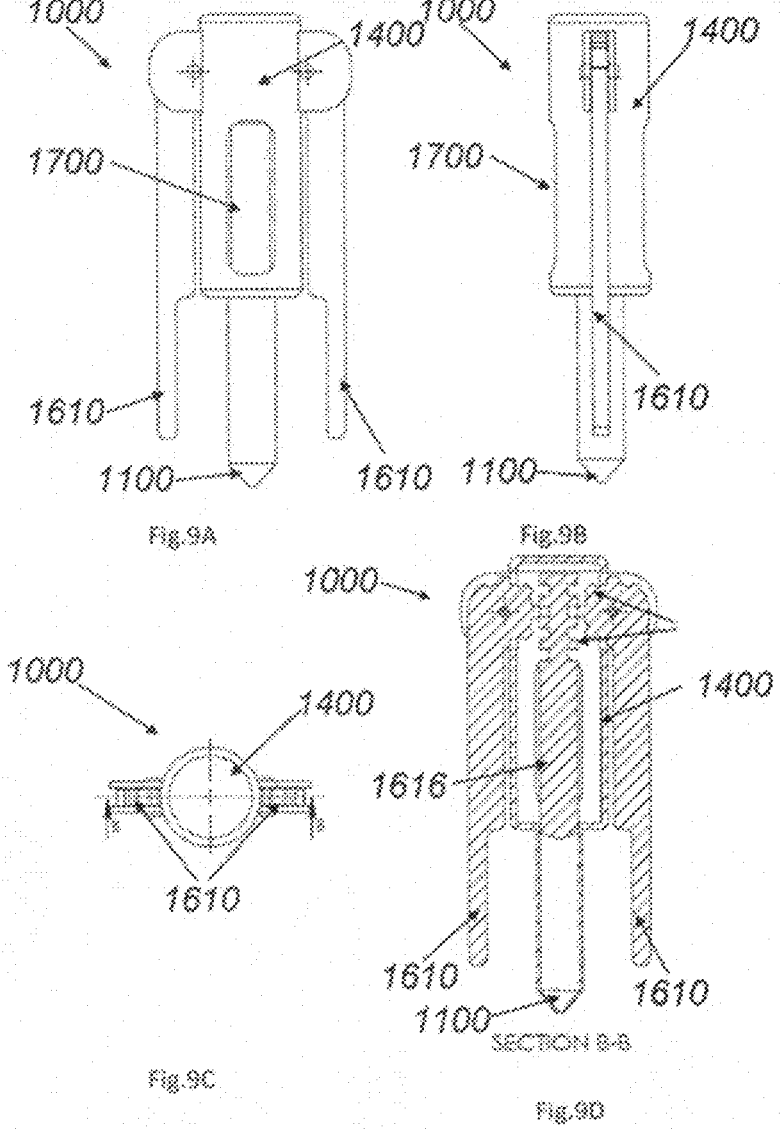

FIGS. 8A and 9A show front views of the device, FIGS. 8B and 9B show side views, while FIG. 8C shows a bottom view and FIG. 9C shows a top view. FIG. 9D shows a cross-section along the line BB in FIG. 9C.

FIG. 10A-10B shows an exploded view of the embodiment of the device shown in FIG. 9A-9D. FIG. 10A shows a front view of the exploded device, while FIG. 10B shows a perspective view of the exploded device.

In reference to FIGS. 8A-8C and 10A-10B, the levers (1610) are rotatably connected to the outer walls of the chamber (1400). In the embodiment shown, the connection is by means of a pin (1402) extending through ears (1404) firmly attached to the sides of the chamber (1400).

The levers are connected by means of a ratchet system (1612) to a plunger (1616) which fits snugly, fluid-tightly and slidably within the barrel (1400).

The levers (1610) have at least two positions, a first, parallel position where the levers (1610) are substantially parallel to the sides of the chamber (1400) and a second, perpendicular position where the levers (1610) are substantially perpendicular to the sides of the chamber (1400).

In the parallel position, the plunger (1616) is extended as far as possible away from the delivery (distal) end (1100) of the device (1000). In the perpendicular position, the plunger (1616) is as close as possible to the delivery (distal) end (1100) of the device (1000).

Dispensing a material from a rechargeable embodiment of the device operating in the manner of the embodiment shown in FIGS. 8A-8C and 10A-10B is a three-step process.

In the first, filling, step, the levers (1610) are placed in their parallel position if they are not already in that position and the device is set to a mode whereby air is able to enter the chamber (1400). One non-limiting example of setting the device to this mode is by opening of a valve (not shown).

In the second, charging, step, the device is set to a mode whereby air is not able to enter or leave the chamber (1400), for non-limiting example, by closing the valve opened in Step 1. The levers (1610) are moved to the perpendicular position (not shown), thereby compressing the gas in the chamber (1400).

In the third, activating, step, the device is activated using any of the activators described herein or known in the art.

In some embodiments operating in the manner of the embodiment shown in FIGS. 8A-8C and 10A-10B, the device is provided in a pre-filled condition, with the handles in the perpendicular position. In such embodiments, the filling step is omitted and dispensing the material is a two-step process comprising steps 2 and 3 above.

In other embodiments, the device is provided without a capsule or with no drug in its capsule and the drug is loaded into the capsule as a preliminary step, as described hereinbelow, before charging and activation of the device.

FIGS. 11A-11F shows another embodiment of a charging mechanism (1620). In the mechanism of FIGS. 11A-11F, charging is by means of a single side lever (1620).

Figures 11A, 11B, 11C, 11D:
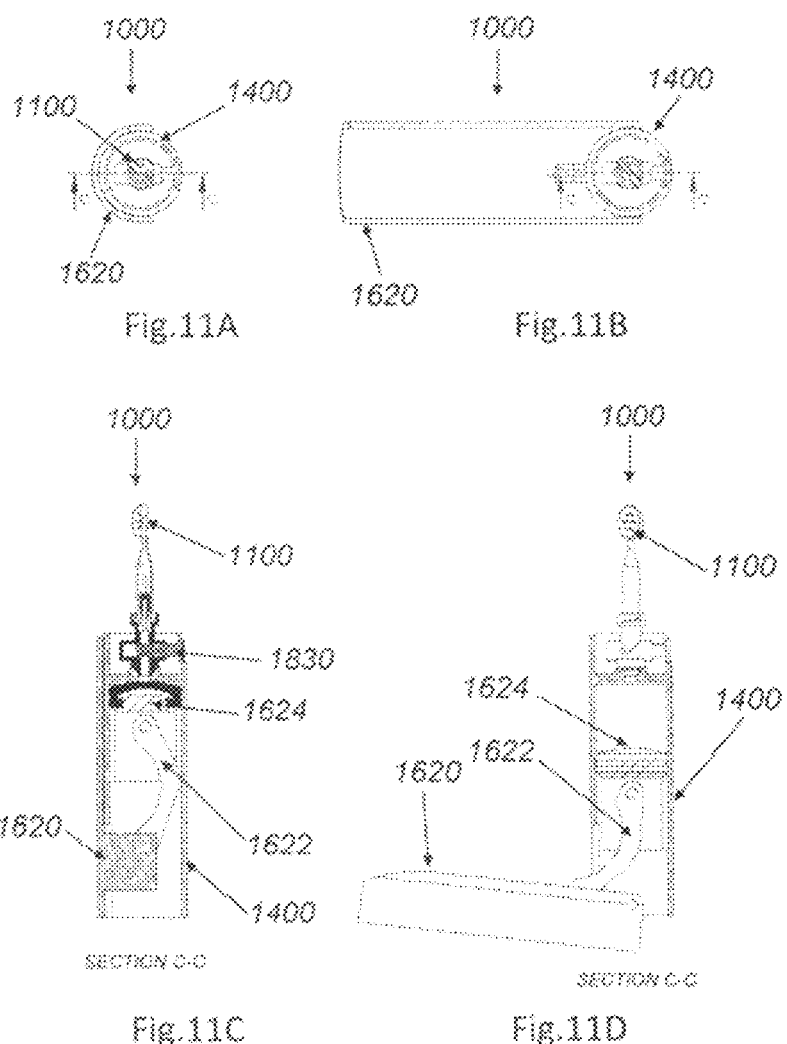
Figures 11E, 11F:
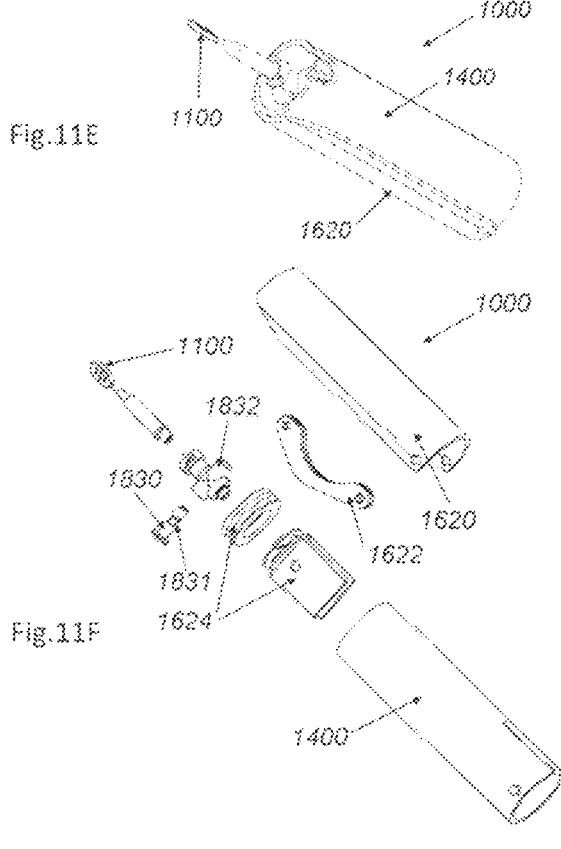

FIGS. 11A and 11C show the device (1000) with the single side lever (1620) in a position substantially parallel to the sides of the chamber (1400), while FIGS. 11B and 11D show the device (1000) with the single side lever (1620) in a position substantially perpendicular to the sides of the chamber (1400). FIG. 11E shows a perspective view of the device (1000) while FIG. 11F shows an exploded view of the device (1000).

FIGS. 11A-11B show a top view of the device (1000), while FIGS. 11C-11D show a cross-section along the lines CC of FIGS. 11A and 11B.

The charging mechanism shown in FIGS. 11A-11F comprises the single lever (1620), which is rotatably connected to the exterior of the chamber (1400) (see FIGS. 11A-11B). The single lever (1620) is also rotatably connected to an arm (1622) (see FIGS. 11C-11D), said arm (1622) being connected to a plunger head (1624) which is in snug, slidable and fluid-tight communication with the chamber (1400).

To charge the mechanism, the single side lever (1620) is rotated from the parallel position (FIGS. 11A, 11C) to the perpendicular position (FIGS. 11B, 11D), pulling the plunger head (1624) away from the delivery end (1100) and filling the chamber (1400) with gas. The handle is then rotated back to the parallel position (FIGS. 11A, 11C), compressing the gas and transforming the device (1000) into the activated configuration. The device can then be activated using a pressable button (1830) or any other activator such as is disclosed herein or is known in the art.

In some embodiments of devices operating in this manner where the handle is substantially parallel to the barrel in the charged position, moving the handle into the charged position, parallel to the barrel, locks the handle and insures that full charging of the device is retained until activation.

It can be seen from the exploded view of the embodiment (FIG. 11F) that depressing the pressable button (1830) causes a gap (1831) to become aligned with the bore of the button housing (1832), thereby allowing compressed gas to escape from the chamber (1400).

Figure 12A:
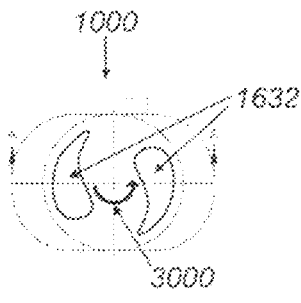
Figures 13A, 13B, 13C:
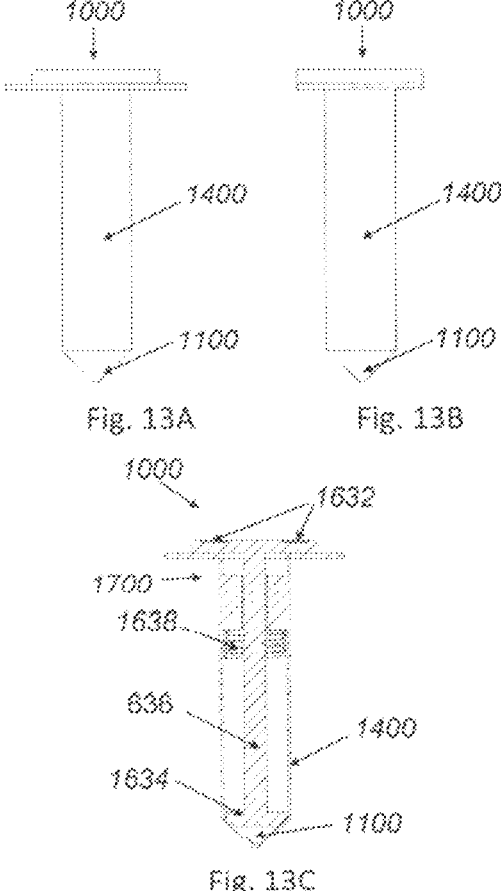

FIGS. 12A 13C show embodiments of devices (1000) where charging is accomplished by rotating the plunger (1636) within the chamber (1400). In these embodiments, the top of the plunger (1636) has finger holes (1632); the user places fingers in the finger holes (1632) to provide the force to charge the device (1000) by rotating the plunger (1636).

Figure 12B:
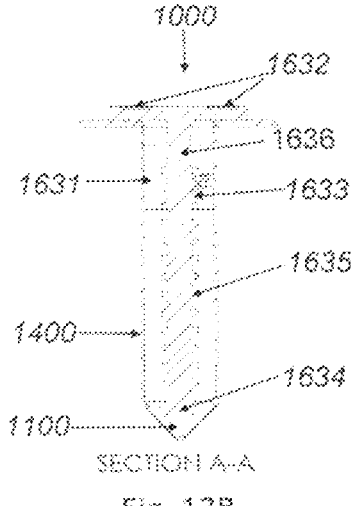

FIG. 12A shows a top view of a rotating plunger device (1000) and FIG. 12B shows a cross-section along the line AA.

In the embodiment of FIG. 12A-12B, to charge the device, the plunger (1636) is rotated clockwise, in the opposite direction from the arrow (3000). This raises the plunger (1636) away from the delivery end (1100), allowing air to enter the chamber (1400). The plunger (1636) is then screwed down (anticlockwise, in the direction of the arrow (3000) to compress the gas and charge the device (1000). Triggering and release of the gas from the delivery end (1100) can be by any activator, such as those disclosed herein or by any activator known in the art.

In further reference to FIG. 12B, the plunger head (1634) is in snug, fluid-tight and slidable communication with the inside of the chamber (1400). The plunger (1636) comprises a screw thread (1635) and passes through a nut (1631) which is in fixed and fluid-tight communication with the inside of the proximal end of the chamber (1400) and which has an internal screw thread (1633) so that rotation of the plunger reversibly screws the plunger (1636) distally or proximally within the chamber (1400).

In the embodiments of FIGS. 13A-13C, lowering of the plunger is by means of a spring (1638). FIG. 13A shows a front view of the device, FIG. 13B shows a side view, and FIG. 13C shows a vertical cross-section.

In some variants of the embodiment of FIGS. 13A-13C, the device is intended as an emergency device and is supplied pre-filled, with the plunger substantially out of the barrel so that the device is full of gas and the spring is compressed. In other variants, to fill the device, the plunger is rotated in a predetermined direction, say, anticlockwise, using the finger holes (1632) to provide a good finger grip (so as to prevent any slippage), thus filling the barrel with gas and compressing the spring. To charge the device, the plunger (1636) is rotated in the opposite predetermined direction, say, clockwise, again using the finger holes (1632) to provide a good grip. This decompresses the spring (1638), moving the plunger (1636) towards the delivery end (1100), compressing the gas and charging the device (1000). When the device is charged, the spring (1638) holds the plunger (1636) in the activated position. Triggering and release of the gas from the delivery end (1100) can be by any activator, such as those disclosed herein or by any activator known in the art.

Figure 14:
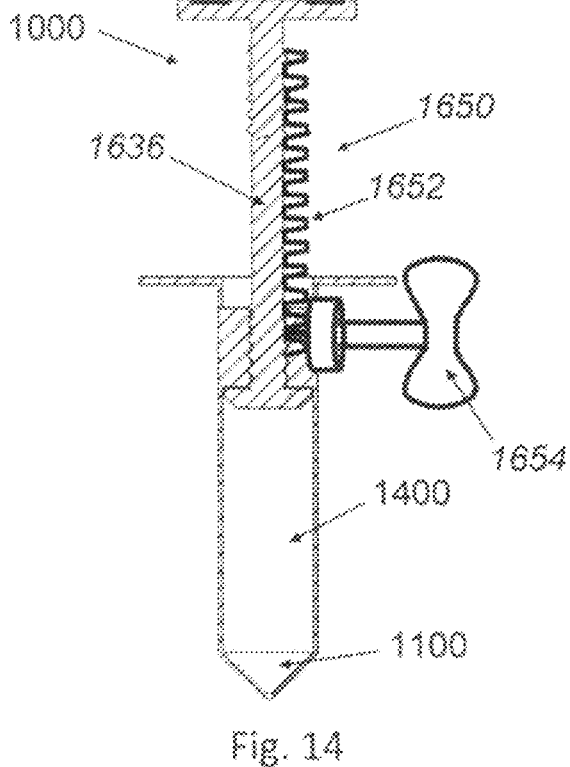

FIG. 14 shows an embodiment of the device (1000) with two-way ratchet mechanism (1650) driven by a key (1654). Turning the key (1654) in one direction (say clockwise) will drive the plunger (1636) upward, away from the delivery end (1100), filling the barrel (1400) with air. Turning the key (1654) in the opposite directions (say, counterclockwise) will drive the plunger (1636) downward, toward the delivery end (1100), compressing the gas and charging the device. Release of the material can be by any means either as described herein or as known in the art. As described hereinabove, the device can be provided pre-filled with gas, requiring only charging before activation, or can be provided in a pre-filled and charged condition, needing only activation.

In some embodiments, a one-way ratchet is used instead of a two-way ratchet (1652). In reusable versions of such embodiments, the plunger (1636) is pulled out (rather than screwed out) to fill the device and screwed down using the key (1654) during charging. In one-use, prefilled devices, a one-way ratchet would be the preferred embodiment, as there is no need to pull out the plunger (1636).

Figures 15A, 15B:
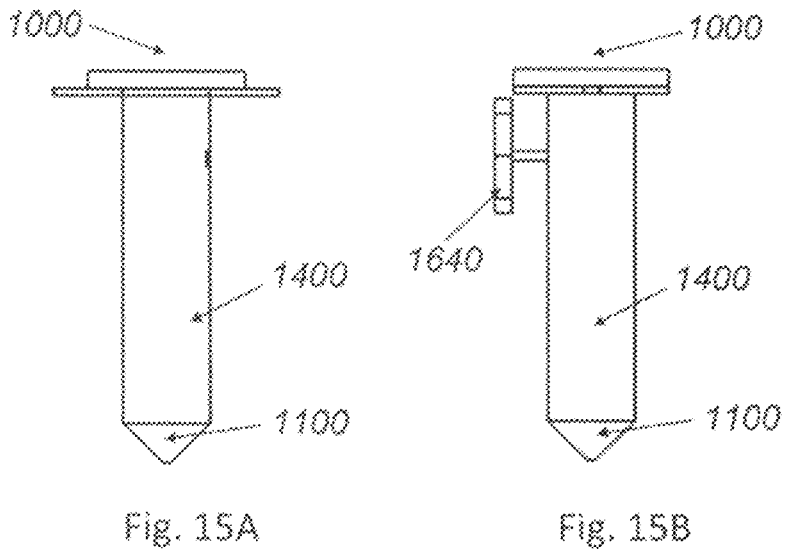

FIGS. 15A-15B show an embodiment of the device (1000) with a side wheel (1640). The side wheel (1640) can drive the plunger via a screw mechanism (1633, 1635, FIG. 12B), a spring mechanism (1638, FIG. 13C), a ratchet (1650, FIG. 14) or any other means known in the art.

Figures 16A, 16B, 16C, 16D:
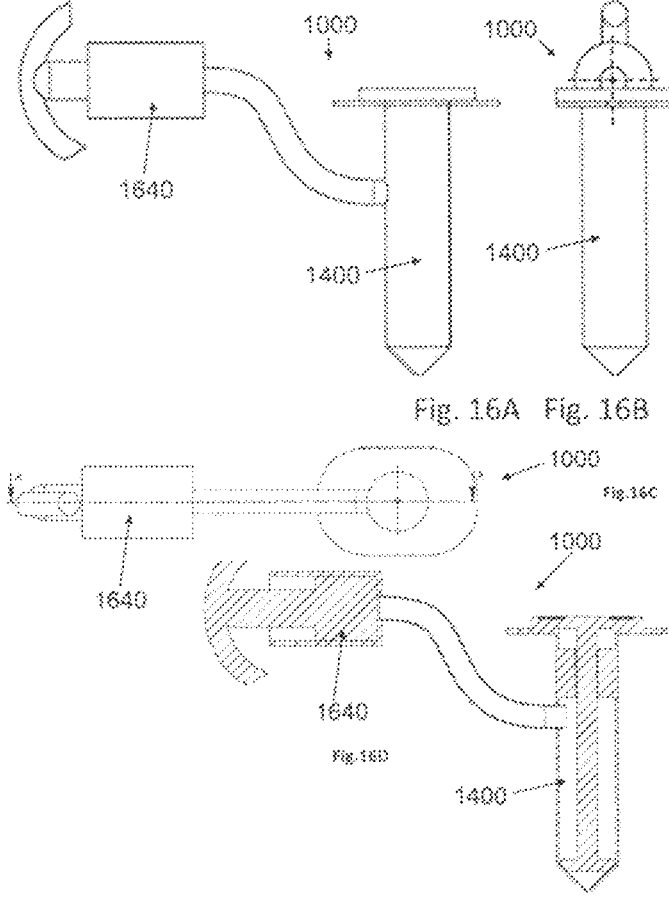

FIGS. 16A-16D show an embodiment of the device (1000) wherein the charging mechanism is a pump (1640). FIG. 16A shows a front view of the device (1000), FIG. 16B shows a side view, FIG. 16C shows a top view, and FIG. 16D shows a cross-section along the line AA.

The pump pumps a predetermined amount of gas into the chamber (1400). Determination of the predetermined amount of gas can be by means of a pressure gauge, a mass flow meter, a scale, or any other means known in the art of delivering a predetermined amount of gas into a predetermined volume.

The gas can be air, nitrogen, oxygen, carbon dioxide, helium, neon, xenon and any combination thereof.

The pump can be a motor-driven pump or a manually-driven pump. The motor power can be provided by conventional electrical mains power, by a battery, by gasoline or other liquid fuel, by solid fuel, by solar power, or by any other power source adapted to drive a pump.

In a manually-driven pump, the pump mechanism can comprise a commercial indiflator (FIGS. 17A-17C), a device combining a pump mechanism and a pressure indicator. Indiflators can controllably produce a high pressure and monitor this pressure. A device comprising an indiflator, a means of storing a deliverable material such one of the capsules disclosed hereinbelow, and a valve at the indiflator's tubing end would enable the user to keep the desired compressed air at the desired pressure for an indefinite time, until the device is activated.

Pump-driven devices can be either pre-filled with air (or a predetermined gas or mixture of gases) or it can be filled by the user utilizing ambient air as compressible gas.

The location of the nozzle or delivery end of the device in the nasal cavity at the time of drug release affects the location of the aerosol in the nasal cavity and the distribution of the drug in the different nasal epithelium layers. These elements affect the drug absorption at the nasal cavity and thus distribution of the drug in the systemic and CNS targets. Therefore, different nozzle shapes and sizes can be used to control the location of introduction of the aerosol into the nasal cavity. Embodiments of nozzle shapes can be seen in the embodiments disclosed herein.

FIGS. 18A-20D show the loading and triggering region of embodiments of devices with mechanical triggering mechanisms, all of which are adapted to open fully, quickly and reproducibly, with the time over which the valve opens being reproducible, independent of how the user may operate the device. For example, in the suction devices described herein, a weak suction will induce the same full opening over the same time period as a strong suction, and, in the mechanical devices disclosed herein a slow activation of the triggering mechanism will induce the same full opening over the same time period as a rapid activation of the triggering mechanism.

FIG. 18A-18D shows an embodiment (1000) of a device adapted to discharge the substance into a nostril, wherein the triggering mechanism, a stopcock trigger, comprises a stopcock activation mechanism, (1820) adapted to provide an all-or-nothing activation mechanism.

Figures 18A, 18B, 18C, 18D:
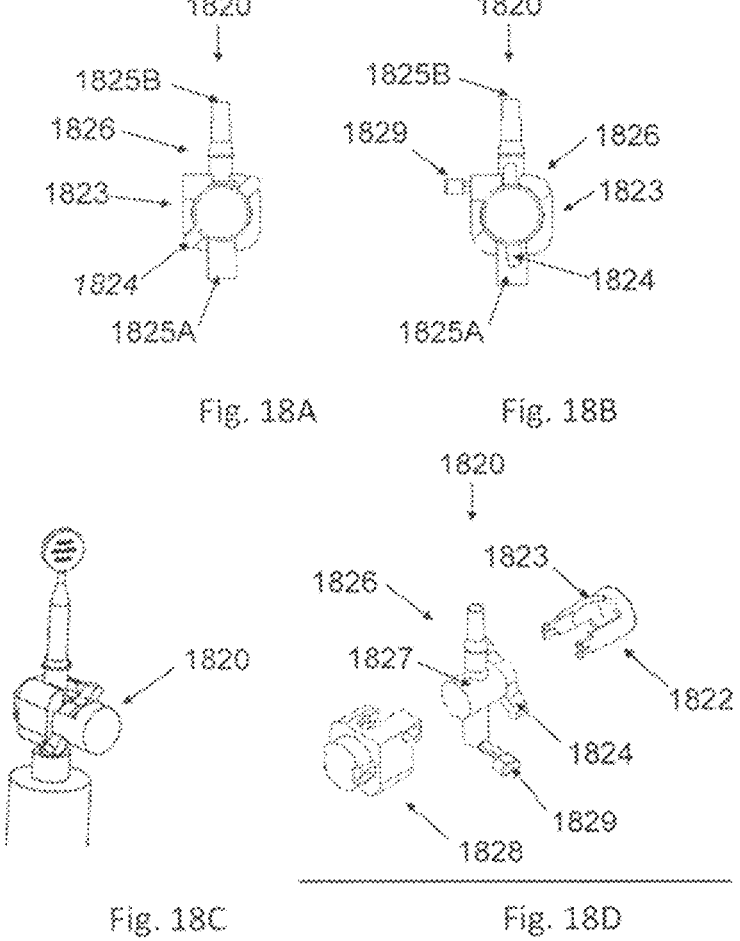

FIG. 18A shows the stopcock trigger (1820) in the closed position, FIG. 18B shows it in the open position, FIG. 18C shows a perspective view of the stopcock trigger (1820) in the open position and FIG. 18D shows an exploded view of the stopcock trigger (1820).

In the embodiment shown, the device is activated by pressing together the two halves of the trigger cover (1822, 1828), thereby rotating the stopcock (1826) from its OFF position (FIG. 18A) to its ON position (FIG. 18B) to release the compressed gas; as described above, the compressed gas then entrains the stored substance, thereby delivering the stored substance to the nostril.

In preferred variants of embodiments with a stopcock trigger (1820), a return mechanism returns the stopcock (1826) to the closed position. The return mechanism can be a spring (not shown), a deactivation pin (1829), any combination thereof, or any other return mechanism known in the art.

In some embodiments, the stopcock (1826) is used without the trigger cover (1822, 1828). In such embodiments, triggering is by manually rotating the stopcock handle (1824) to the ON position (FIG. 18B) and resetting is by manually rotating the stopcock handle (1824) to the OFF position (FIG. 18A).

FIG. 19A-19D shows a device with a bypass trigger, wherein the triggering mechanism comprises a pressable button (1830) which activates a bypass activator (1900, not shown). Activation of the device is by pressing the button (1830), thereby releasing the compressed gas. The compressed gas entrains the stored substance, thereby delivering the stored substance to the nostril.

Figures 19A, 19B, 19C, 19D:
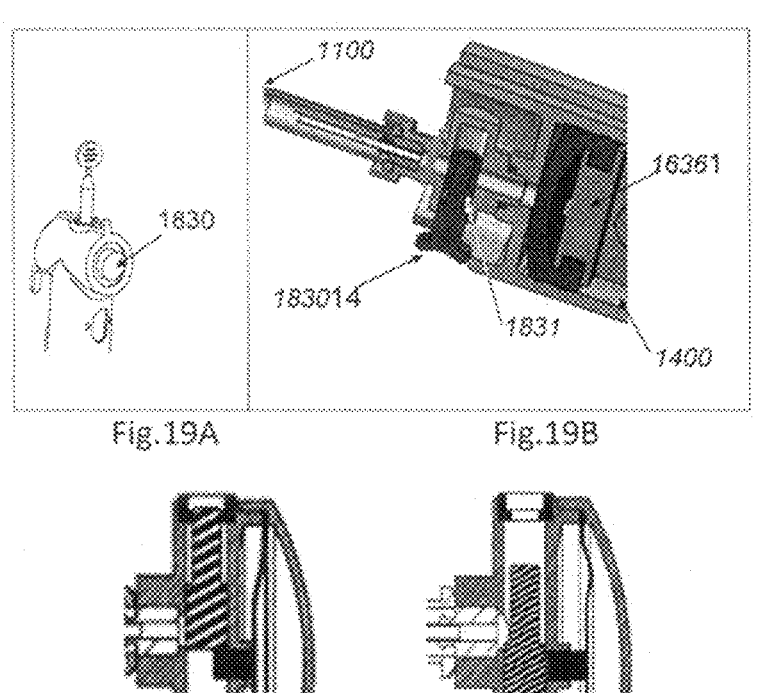

FIG. 19A shows a perspective view of the bypass triggering mechanism while FIG. 19B shows a perspective view of a cross-section of the triggering mechanism. In FIG. 19B, the distal end of the plunger (1636) is at the right, and the delivery end (1100) is at the left. The pressable button (1830) is shown in its closed position; the stem (1833) of the button blocks passage of air between the barrel (1400) and the delivery end (1100). When the button (1830) is depressed, the bypass (1831) becomes aligned with the air passage (1410) between the barrel (1400) and the delivery end (1100), allowing the pressurized gas to escape from the barrel (1400), exit the delivery end (1100), and enter the nasal passage or other body orifice. FIG. 19C shows a cross-section of the activation mechanism in the closed position, while FIG. 19D shows a cross-section of the activation mechanism in the open position.

FIG. 20A-20D shows a preferred embodiment of the loading portion of the device (1000) with a pinch triggering mechanism. FIG. 20A shows a side view of the device, FIG. 20B shows a cross-section, taken along the line AA in FIG. 20A, FIG. 20C shows an exploded view, and FIG. 20D shows a perspective view.

The device comprises a hollow upstream portion (1881) fluid-tightly connected to a hollow downstream portion (1889). In this embodiment, the activation mechanism (1880) comprises a cup-shaped insert (1884) fitting snugly and fluid-tightly within the hollow interior of the device. The outer rim of the insert (1884) is preferably fixed to the outer wall of the activation mechanism (1880), with its inner rim (1885) able to slide on an inner wall (1886), preferably tubular, of the activation mechanism (1880). In the activation mechanism's (1880) closed position, a stop (1882) is firmly held by the inner rim (1885) of the insert.

The inner wall of the activation mechanism (1880) comprises a throughgoing bore (1883). In some variants of this embodiment, a flexible tube (1888) is fluid-tightly fixed to the wall (1886) such that there is flexible tubing in at least the portion of the wall abutting the stop (1882). In other variants of this embodiment, the flexible tube (1888) passes through the bore (1883).

In preferred variants of this embodiment of an activation mechanism, in the closed position, the stop (1882) fits into and sits in a hole in the inner wall (1886). In other variants, the stop (1882) fits into and sits in a depression in the inner wall (1886).

When the activation mechanism (1880) is in the closed position, the flexible tube (1888) is pinched between the stop (1882) and the inner side of the throughgoing bore (1883).

When the activation mechanism (1880) is activated, the insert (1884) slides up along the wall, releasing the stop (1882) so that the pinched region in the flexible tube (1888) is released, thereby releasing the pressurized gas and dispensing the substance.

In the embodiment shown in FIGS. 20A-20D, the activation mechanism can be activated either by sucking on the suction mechanism (1810), creating a partial vacuum above the cup-shaped insert (1884) and pulling it upward, thereby releasing the stop (1882), or by pressing the pressable lever (1870). Pressing the pressable lever (1870) forces it inward so that the ramp portion (1782) of the pressable lever pushes the cup-shaped insert (1884) upward, thereby releasing the stop (1882), releasing the pressurized gas and dispensing the substance.

In some embodiments, flexible filling material such as, but not limited to, flexible tubing, can be placed within the region of the device (not shown) containing the substance to be delivered in order to reduce dead space within the device. Reducing dead space will not affect the characteristics of the aerosol formed after release, but it will decrease pressure loss and increase air speed within the device, thereby substantially reducing residual substance remaining within the device after completion of activation, either within the capsule or adhering to the interior walls of the device, e.g., within the nozzle. It is well known in the art that residual material within a delivery device can be released on subsequent uses of the device and that the amount of such residual material released during a given use of a device is extremely variable. Therefore, minimizing residual substance within the device will increase the accuracy and reproducibility of delivery, thereby increasing increase its repeatability and reliability, both by maximizing the fraction of the substance actually delivered from the current capsule and by minimizing the amount of residual substance on the walls of the device.

It should be noted that the capsules (disclosed hereinbelow) are designed so as to avoid residual volume within the capsule itself, since, even in the case of a single dose or disposable capsule there are safety issues involved in disposing of capsules containing residual amounts of hazardous drugs or other hazardous component in the composition.

Other trigger mechanisms include, but are not limited to, a releasable catch, a pressable button a detactable predetermined sound pattern, a detectable predetermined light pattern, a moveable lever, a slider moveable from a first position to a second position, a rotatable knob is rotated, a releasable latch adapted and any combination thereof.

The predetermined sound pattern can be: a constant-pitch sound, a varying-pitch sound, a constant volume sound, a varying volume sound and any combination thereof.

The predetermined light pattern can be: a constant-color light, a varying-color light, a constant brightness light, a varying brightness light and any combination thereof.

In some embodiments, the device comprises a unidirectional valve such that gas can flow from the charging mechanism to the delivery end, but is unable to flow in the reverse direction.

In some embodiments, a substance to be dispensed (which can comprise any number of materials) can be stored within a capsule, either as the substance to be dispensed or as a precursor or precursors, with the capsule placeable within the device, as described hereinbelow. In such embodiments, the capsule is ruptured during activation, either all at once or in stages, thereby dispensing the substance.

In other embodiments, a substance, prepared in a conventional matter, is introducible into a holding chamber within the device and, on activation of the device, the substance is dispensed. Embodiments of this kind are primarily intended for use as emergency dispensing devices, since any flowable substance can be introduced into the holding chamber and since the holding chamber, which has no facilities for separating precursors or for providing an inert atmosphere in the chamber, is not intended for long-term storage of substances.

In some embodiments, the capsule chamber in which the capsule can be placed can also function as a holding chamber, so that the substance can be dispensed either from the capsule or directly from the holding chamber.

In other embodiments, an insert can be placed within the capsule chamber, with the interior of the insert being a holding chamber.

Figures 21A, 21B, 21C:
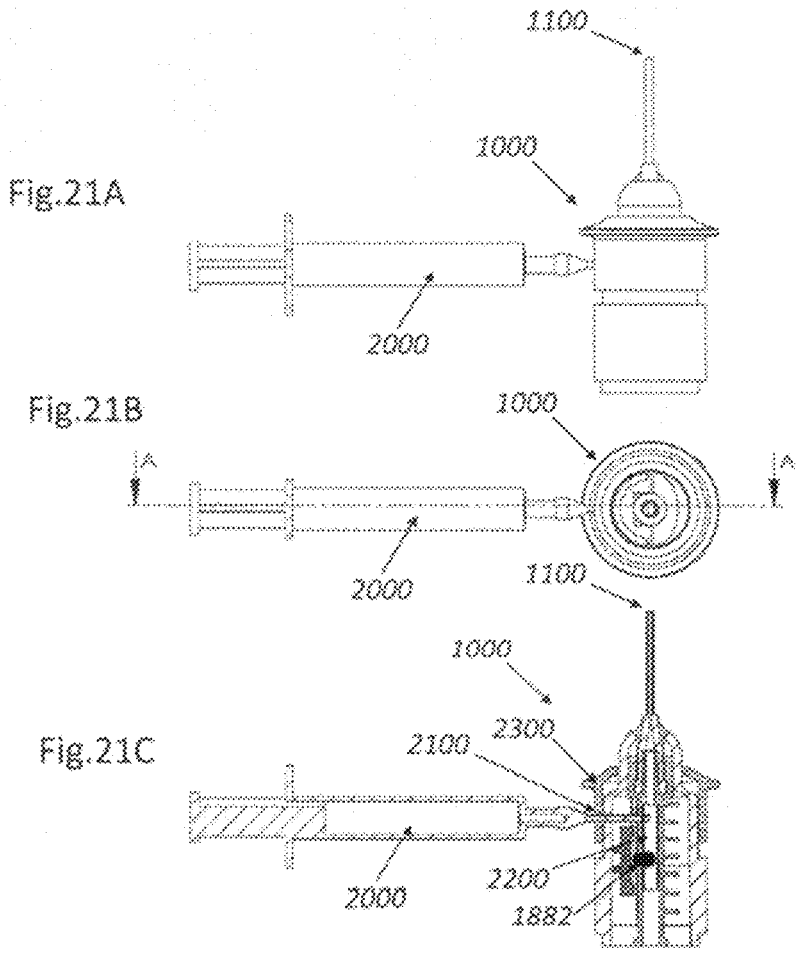
FIGS. 21A, 21B and 21C schematically illustrate an embodiment of the loading mechanism portion of a device to deliver a predetermined amount of a substance to a natural orifice of the body.

An embodiment of the activation mechanism of such an emergency-type dispensing device (1000) is shown in FIGS. 21A-21C. The charging mechanism is not shown. FIG. 21A shows a side view of the embodiment, FIG. 21B shows a top view of the embodiment, and FIG. 21C shows a cross-section, taken along the line AA in FIG. 21B.

In this embodiment, the means of loading the substance into the device is a loader, such as a syringe (2000). The syringe (2000) can be placed in the injection port (2100, FIG. 21C) and the syringe plunger depressed so that the flowable substance enters a dispensing chamber (2200) within the device (1000). Before, during or after injection of the substance into the chamber, the device can be charged, in any manner described herein, using any activation mechanism described herein or known in the art.

In some embodiments, the syringe is left in the injection port. In other embodiments, a cover (2300) is provided for the injection port, so that, after loading the substance into the chamber, the injection port can be sealed by means of the cover. As shown in the embodiment of FIG. 21C, the cover (2300) can slide longitudinally onto and off the injection port (2100), In other embodiments, it can rotate or spiral around the device to cover or uncover the injection port (2100), it can rotate around a hinge on the body of the device so that it flips onto and off the injection port (2100), or any other method of sealing the port can be used. In the embodiment as shown, in the open position, the syringe goes through a hole in the cover in order to reach the chamber. Any combination of the above embodiments can be used in a cover.

In the embodiment shown, a pinch triggering mechanism is used, as shown hereinabove in FIGS. 20A-20D, although any of the other activation mechanisms described herein or any conventional valve known in the art can be used.

Figures 22A, 22B, 22C, 22D:
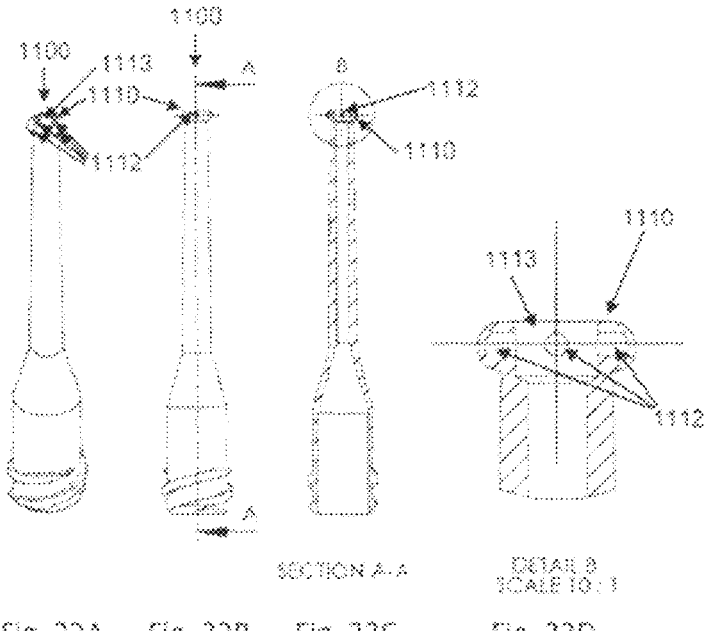
FIGS. 22A, 22B, 22C and 22D and 23A, 23B, 23C, 23D, 23E, 23F, 23G and 23H schematically illustrate embodiments of nozzles or delivery ends.

In reference to FIGS. 22A-23H, two embodiments of nozzles (1100) are shown. In both FIGS. 22A-22D and FIGS. 23A-23H, the nozzle (1100) has a tip extension (1110) with a larger diameter than the nozzle, the tip extension substantially surrounding the distal end of the nozzle (1100). In the exemplary embodiment of both FIGS. 22A-22D and FIGS. 23A-23H, the tip extension (1110) has holes (1112) in it to allow substance to exit laterally from the extension, and the tip (1110) has at least one hole (1113) in its distal end to allow substance to exit longitudinally from the nozzle (1100). FIGS. 22A-22D shows an embodiment of a nozzle (1100) with a tip extension (1110). FIG. 22A shows a perspective view of the nozzle (1100) from the distal end, while FIG. 22B shows a side view. FIG. 22C shows a cross-section of the nozzle along the line AA in FIG. 22A, while FIG. 22D shows an enlarged view of the circled region B at the tip of the nozzle in FIG. 22C, showing the tip of the nozzle and the tip extension in more detail. The holes (1112) in the tip extension (1110) and the hole (1113) in the tip can be clearly seen. In some embodiments, the nozzle (1110) has only lateral holes (1112), so that no substance escapes from the distal end of the nozzle (1110).

Figures 23A, 23B, 23C, 23D, 23E, 23F, 23G, 23H:
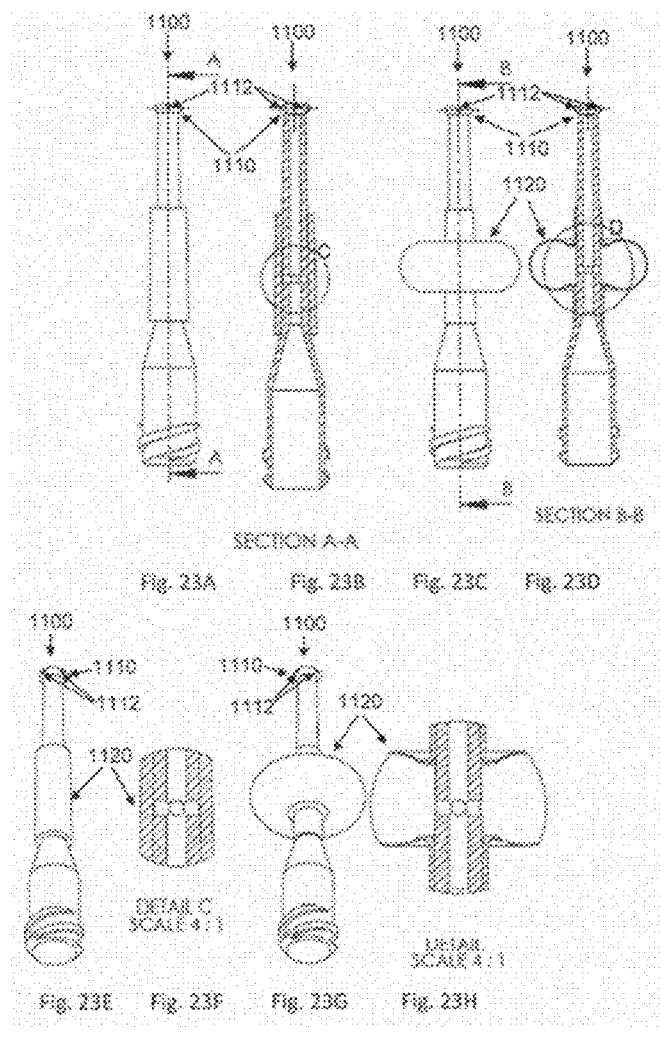

In order to prevent material from escaping from the nasal passages or entering undesired areas in the nasal cavity, in some embodiments, the nozzle comprises a medial extension, an expandable portion (1120). FIGS. 23A-23H shows an embodiment of a nozzle with a tip extension (1110) and an expandable portion (1120). FIGS. 23E and 23G show perspective views of the nozzle from the proximal end, while FIG. 23A and FIG. 23C show side views of the nozzle (1100). FIGS. 23B and 23D show cross-sections of the nozzle (1100) along the lines AA in FIG. 23A and BB in FIG. 23C, respectively. FIG. 23F shows an enlarged view of the circled region C in the center of the nozzle in FIG. 23B, while FIG. 23H shows an enlarged view of the circled region D in the center of the nozzle in FIG. 23D.

FIGS. 23A, 23B, 23E and 23F show the nozzle with unexpanded expandable portion, while FIGS. 23C, 23D, 23G and 23H show the nozzle with expanded expandable portion.

In the exemplary embodiments of FIGS. 22A-23H, the tip extension and the expanded medial extension are substantially toroidal; in other embodiments, they can be substantially spherical, substantially ovoid, substantially ellipsoidal, substantially the frustum of a cone (preferably with a rounded distal edge), substantially conic (preferably with a rounded distal edge) and any combination thereof.

The nozzle tip and the tip extension (1110) have a number of holes (1112, 1113) which fluidly connect the bore of the nozzle (1100) to the exterior of the device, allowing material to exit from the interior of the device. In the exemplary embodiments shown, there is a hole (1113) (FIGS. 22A and 22C; not shown in FIGS. 23A-23H) in the distal end of the nozzle and four holes (1112) in the tip extension (1100). Both the extension and the distal end of the nozzle can have more or fewer holes and, in some embodiments, one or the other can have no holes. The holes (1112) can be regularly spaced around the periphery of the extension, the holes (1112) can be irregularly spaced around the periphery, the holes (1112) can be concentrated in a predetermined part of the periphery, and any combination thereof. Similarly, the holes in the distal end of the tip can be regularly or irregularly spaced in the tip.

In some embodiments, the extension (1110) can be padded, can comprise soft material, can comprise flexible material and any combination thereof.

Extensions, both tip extensions and medial extensions, can have a number of functions. A non-limiting list of such functions is (1) ensuring proper positioning of the nozzle (1100) in the nasal passages, where the proper position can be the nozzle (1100) centralized in the nasal passages, the nozzle (1100) touching a predetermined portion of the nasal passages, or the nozzle (1100) closer to a predetermined portion of the nasal passages, (2) sealing the nasal passages so that material can not escape therefrom, (3) sealing the nasal passage so that substance does not contact undesired portions thereof, (4) sealing the nasal passage so that substance remains in a predetermined region of the nasal passage, (5) reducing the discomfort of contact between the nozzle and the nasal passages, especially in embodiments where the extension is intended to seal against the walls of the nasal passages, by providing a soft and/or flexible contact region and any combination thereof. Proper positioning can be for the purpose of improving delivery of a substance to a predetermined area, preventing clogging of the holes by nasal secretions, preventing clogging of the holes by contact with the nasal passages, mucosa and any combination thereof.

Nozzle extensions, both those that are expanded during the activation procedure and those that have a predetermined shape and do not expand, can either (1) be attached to the nozzle in a way that they are removed from the nasal cavity with the nozzle tip itself, or (2) have the option of being releasable from the nozzle tip so that they stay in the nasal cavity until they are pulled out by the user or by a caregiver, or any combination thereof. In embodiments where at least one nozzle extension remains in a nasal cavity, preferably, the nozzle extension or extensions are removed after a predetermined time, preferably a short time.

In some embodiments, the holes (1112) in the nozzle (1100) do not lie substantially in a plane perpendicular to the main longitudinal axis of the nozzle (1100). In such embodiments, the holes (1112) can lie along a line parallel to the main longitudinal axis of the nozzle (1100), along a line forming a spiral around the nozzle (1100), irregularly in the distal portion of the nozzle (1100), regularly spaced in the distal portion of the nozzle (1100), and any combination thereof.

Therefore, dispersion of the drug can be substantially from a ring perpendicular to the main longitudinal axis of the nozzle (1100) (holes (1112) around the edge of the extension (1110)), from a circle perpendicular to the main longitudinal axis of the nozzle (1100) (holes (1113) in the distal tip of the nozzle (1100)), from a line (holes (1112) parallel to the main longitudinal axis of the nozzle (1100) or in a spiral around the main longitudinal axis of the nozzle (1100)), or from at least part of the surface of a volume extending along the side of the nozzle (1100).

In some embodiments, the size of the tip extension (1110) is selected so that the extension (1110) is in contact with the nasal passages substantially along its entire circumference. In such embodiments, material exiting holes (1113) in the distal tip of the nozzle (1100) or holes (1112) on the distal face of the extension (1110) cannot reach regions proximal to the extension (1110) and will reach only regions deeper in the nasal passages than the extension (1110). In such embodiments, the substance will reach the upper parts of the nasal passages and the lungs.

Material exiting from holes (1112) in locations where the extension (1110) is in contact with the nasal passages will deposit directly on the walls of the nasal passages. In such embodiments, deposition is in a very narrow band; the location of the band can be tailored for the material of interest.

Material exiting holes (1112) proximal to the region of the extension (1110) in contact with the walls of the nasal passages will be unable to reach locations distal to the region of the extension (1110) in contact with the walls of the nasal passages and will therefore deposit in the lower parts of the nasal passages.

Returning to FIGS. 23A-23H, in this embodiment, the expandable portion (1120) surrounds the nozzle (1100). In other embodiments, the expandable portion (1120) can partially surround the nozzle (1100). A single expandable portion (1120) or a plurality of expandable portions (1120) can be used. An expandable portion can be on the surface of the nozzle or it can be stored within the nozzle, popping out when it expands. An expandable portion can have a predetermined shape when expanded. The shape of the outward-facing part of an expandable portion can be part of the surface of a spheroid, can be part of a cylinder, a part of a cone, or can conform to the shape of a predetermined portion of a nasal passage. Such shaping can help ensure that, on inflation, the expandable portion or portions gently guide the nozzle so that it rests in the position with respect to the nasal passages or in the correct portion of the nasal passages. It can also reduce the user's discomfort when the device is in place or, if detachable from the device, it can seal the nasal passage for a time, before being removed by the user or a caretaker.

The expandable portion (1120) is preferably inflated after insertion of the device into the nasal passage. Inflation can be before or at the time of activation of the device.

In embodiments where delivery is to a nostril, delivery of the substance can be improved by inducing sniffing in the user.

Sniffing (short, sharp breaths through the nose, for example, when smelling something) is highly correlated with soft palate (Velum) position. Sniffs are rapidly modulated in an odorant-dependent fashion by a dedicated olfactomotor system, and affect the position of the soft palate at the posterior end of the nasal cavity. When sniffing through the nose, the palate is in its upper position to cause separation between the nasal cavity and the oral cavity.

In addition to conscious control, sniffing may be reflexively elicited by chemicals, functioning as either irritants or odors in the nose. Overall sniff duration and pattern can be modulated in real time to enhance olfactory perception. When the olfactory system encounters a concentrated odorant, sniff vigor is reduced and sniff time is reduced; when it encounters a diluted odorant, sniff vigor is increased and duration lengthened. Odorant pleasantness also affects sniffing; sniff vigor and duration increase when smelling a pleasant odor and decrease when smelling an unpleasant odor.

In preferred embodiments, the device disclosed herein can release odorant into the nasal cavity of the user in order to reflexively elicit sniffing. The odorant can be a single odorant or a mixture of odorants and can comprise compounds from different chemical families, for non-limiting example:

Esters: Geranyl Acetate, Ethyl Acetate, Benzyl Acetate, Octyl Acetate.
   Linear Terpens: Geraniol, Citral, Citronella, Nerolidol.
   Cyclic Terpens: Terpineol, Thuj one.
   Aromatic: Eugenol, Vanillin, Anisole, Thymol.
   Amines: Indole.
   Also aromatic compounds of Alcohols, Aldehydes, Esters, Ketones, Lactones, Thiols.

In preferred embodiments, the substance is contained within a capsule. The capsule can have a single compartment or it can be multi-compartment. The capsule can contain a broad range of drugs and materials. The aromatic compound can be stored in the nozzle, or the nozzle or a portion thereof can be impregnated with aromatic compound, so as to trigger the closing of the velum when the nozzle tip is being placed in the nasal cavity. The delivery can be for local effect, to the systemic circulation, to the central nerve system (CNS), to the brain, preferably via the olfactory epithelium, to the spinal cord and associated nerves, and any combination thereof.

As described hereinabove, the drugs and materials to be delivered can be, but are not limited to, pharmaceuticals, natural compounds, biologics, hormones, peptides, proteins, viruses, cells, stem cells and any combination thereof.

The stored substance or substances can be stored as a liquid, an aerosol, a powder, a slurry, a suspension, or a gel, if thin enough. The substance or substances can be stored either with or without a carrier; the carrier can be a liquid, a gas or a powder.

The substance as delivered can comprise a powder, a mixture of liquid and powder, a mixture of gas and powder, a mixture of powders, a liquid, a mixture of liquid and gas, a mixture of liquids, a gas, or a mixture of gases.

The stored substance or substances can be packaged to minimize degradation, for example, by packaging it in vacuum or under an inert atmosphere. Preferably, capsules are single-use so that a single, controllable dose can be delivered with each use of the device. Capsules can be placed in the container of the device, or the container can comprise the capsule.

Use of an inert gas for the carrier for delivery of the medication obviates the possibility of interactions between the user and the delivery carrier; allergies to carriers, especially in medications used for chronic illnesses, are a growing problem. Furthermore, the delivery carrier is in contact with the medicament for no more than a few seconds and more commonly for no more than a few milliseconds, thereby minimizing degradation of the medicament due to interactions with the delivery carrier.

Examples of drugs and materials deliverable using the device are given hereinbelow. All examples listed below are exemplary and are not limiting.

Deliverable drugs and materials include: treatments for allergic rhinitis; treatments for osteoporosis; vaccinations and immunizations; sexual dysfunction drugs; treatments for B12 deficiency; smoking cessation; treatment of gynecological problems; treatment of other women's health issues; general anesthetics; local anesthetics; opioid analgesics; agonist-antagonists and antagonists; antitussives; drugs used in the treatment of motor disorders; antiepileptics; drugs used in affective disorders; antipsychotics (neuroleptics); sedative-hypnotics, anxiolytics, and centrally acting muscle relaxants; treatments for anxiety disorders; skeletal muscle relaxants; treatments for Parkinson's disease; treatments for Alzheimer's disease; treatment for pain and anti migraine treatment.

Medicaments for treatment of allergic rhinitis include: steroids, including corticosteroids, Flonase, Patanase, Beconase, Anihistamine, Astelin, Otrivin, Livostin, Theramax, Avamys, Lufeel, Sinofresh, Nasonex, Nasocort and Veramyst.

Medicaments for treatment of osteporosis include: Miacalcin, Fortical and Stadol.

Medicaments for vaccinations and immunizations include: LAVIN, and influenza vaccines including FluMist.

Medicaments for smoking cessation include: NasalFent.

Other medicaments which can be delivered include: calcitonin and parathyroid hormone.

Neurotransmitters and neuromodulators that can be delivered include: acetylcholine (ACH), Anticholinergic drugs, adenosine triphosphate (ATP), aspartate (Asp), beta-amyloid, beta-endorphin, bradykinin, dopamine (DA), L-DOPA, Carbio-Dopa, epinephrine, dynorphins, endomorphins, enkephalins, 5-hydroxytryptamine (5-HT), Sumatriptan, Imitrex, Migranal, Zolmitriptan, Zomig, Gamma-aminobutyric acid (GABA), glutamate (glu), glycine, histamine, leptin, nerve growth factor and other growth factors), nor-epinephrine, nitric oxide, and Substance P.

General anesthetics which can be delivered include: alfentanil, desflurane, enflurane, etomidate, fentanyl, halothane, isoflurane, ketamine, methohexital, methoxyflurane, midazolam, lorazepam, diazepam morphine, nitrous oxide ($N_2O$), propofol, sevoflurane, Sufentanil, Sublimase, and thiopental.

Local anesthetics which can be delivered include: benzocaine, bupivacaine, cocaine, lidocaine, prilocaine, procaine, ropivacaine, and tetracaine.

Opioid analgesics, agonist-antagonists, and antitussives which can be delivered include: agonists, codeine, diphenoxylate, fentanyl, heroin and other opiods, hydrocodone, l-alpha-acetyl-methadol, levomethadyl acetate, loperamide, meperidine, methadone, morphine, oxycodone, d-propoxyphene, combinations of opioids plus acetaminophen and asa, and tramadol.

Agonist/antagonists and antagonists which can be delivered include: buprenorphine, butorphanol, nalbuphine, nalorphine, naloxone, naltrexone, nalmefene, pentazocine, codeine, dextromethorphan, and hydrocodone.

Drugs used in the treatment of Parkinson's disease and motor disorders which can be delivered include: amantadine, apomorphin, baclofen, benzodiazepines, benztropine, bromocriptine, carbidopa, cyclobenzaprine, dantrolene, dopamine, entacapone, haloperidol, L-DOPA, pergolide, pramiprexole, ropinerole, selegiline (deprenyl), trihexyphenidyl, rasagiline, azilect, selegiline, ladostigil, rotigotine, neupro, mono amine oxidase inhibitor, and COMT inhibitor.

Antiepileptics which can be delivered include: acetazolamide, carbamazepine, clonazepam, diazepam, ethosuximide, felbamate, gabapentin, Lamotrigine, lorazepam, phenobarbital, phenytoin, primidone, tiagabine, topiramate, valproic acid, Vigabatrin and Midazolam.

Drugs used in affective disorders which can be delivered include: antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate and valproic acid.

Antipsychotics (neuroleptics) which can be delivered include: chlorpromazine (CPZ), clozapine, fluphenazine, haloperidol, olanzapine, quetiapine, risperidone, sertindole, thioridazine, thiothixene and ziprasidone.

Sedative-hypnotics, anxiolytics, and centrally acting muscle relaxants which can be delivered include: alprazolam, chloral hydrate, diphenhydramine, flumazenil, flurazepam, hydroxyzine, lorazepam, oxazepam, phenobarbital, temazepam, triazolam, zaleplon and zolpidem.

Anxiety disorders and skeletal muscle relaxants which can be delivered include: alprazolam, chlorazepate, chlordiazepoxide, diazepam, flumazenil (antagonist), lorazepam, and oxazepam.

Treatments for Alzheimer's disease which can be delivered include: donepezil, galantamine, rivastigmine, Tacrine, Detemir, Novolin, Humulin, Insulin, insulin like hormone, an insulin analog such as NPH Insulin, Lispro, Aspart, Detemir Insulin, Glulisin, Glargin Insulin, Insulin degludec, BDNF, GDNF, MIBG, anti cancer agents, anti cancer drugs, dopamine agonist and dopamine antagonist.

Other drugs which can be delivered include: amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, Pentobarbital, neuroprotective compounds, neuroprotective peptides, neuroprotective factors, davunetide, anti schizophrenic drugs, anti depression drugs, comtan, Entacopone, anti ADHD agents, anti ADHD drugs such as Methylphenidrate (ritalin), and anti-autism and anti-autism symptoms drugs.

Other materials that can be delivered include: both purified natural and synthetic biologics, peptides, proteins, antibodies, cells including stem-cells, parts of cells, nanoparticles and microparticles. The nanoparticles and microparticles can comprise drugs; they can be carriers for drugs, cells or parts of cells; and any combination thereof.

In preferred embodiments, the substance comprises permeation enhancers to improve penetration of the active components of the substance through the mucosal membranes.

In some formulations, the formulation can comprise polymeric microparticles comprising at least one active agent and a permeation enhancer, where the active agent is selected from a group consisting of a peptide, a protein, an antibody, nucleic acid, small molecules, cells and any combination thereof.

A great number of penetration enhancers are known in the literature.

One such penetration enhancer is Hyaluronic acid (also referred to as HA or hyaluronan), which is a polysaccharide that occurs naturally in the body. Due to its exceptional water-binding, visco-elastic and biological properties, HA can improve the attributes, such as, but not limited to, the absorption characteristics, of existing formulations and can also add new attributes to existing formulations. Inclusion of HA can be advantageous when developing new formulations.

When used for drug delivery and targeting, HA can provide clear advantages over traditional polymeric substances such as synthetic polymers such as, but not limited to, poly(ethylene glycol), poly(lactic acid), poly(glycolic acid), poly Acrylic Acid and Poly-(N-isopropylacrylamide), or other biopolymers such as chitosan and alginate.

HA's benefits in the drug delivery area include, but are not limited to:

Flexibility when designing controlled drug release profiles;

More stable drug formulations;

Effective drug targeting via accumulation at the targeted site and receptor-mediated uptake;

Enhancement of bioavailability and biocompatibility of drugs; and

Reduction of drug cytotoxicity in healthy tissues polymeric microspheres polymeric controlled release preparation a mucoadhesive agent.

Other penetration enhancers include, but are not limited to the following:

A group containing: a fatty acid, a medium chain glyceride, surfactant, steroidal detergent, an acyl carnitine, Lauroyl-DL-carnitine, an alkanoyl choline, an N-acetylated amino acid, esters, salts, bile salts, sodium salts, nitrogen-containing rings, and derivatives. The enhancer can be an anionic, cationic, zwitterionic, nonionic or combination of both. Anionic can be but not limit to: sodium lauryl sulfate, sodium decyl sulfate, sodium octyl sulfate, N-lauryl sarcosinate, sodium carparate. Cationic can be but not limit to: Cetyltrimethyl ammonium bromide, decyltrimethyl ammonium bromide, benzyldimethyl dodecyl ammonium chloride, myristyltimethyl ammonio chloride, deodecyl pridinium chloride. Zwitterionic can be but not limit to: decyldimethyl ammonio propane sulfonate, palmityldimethyl ammonio propane sulfonate. Fatty acid including but not limit to: butyric, caproic, caprylic, pelargonic, capric, lauric, myristic, palmitic, stearic, arachidic, oleic, linoleic, linolinic acid, their salts, derivatives and any combinations or glyceride, monoglyceride, a diglyceride, or triglyceride of those fatty acids. Bile acids or salts, including conjugated or un-conjugated bile acids, such as but not limited to: cholate, deoxycholate, tauro-cholate, glycocholate, taurodexycho-late, ursodeoxycholate, tauroursodeoxycholate, chenode-oxycholate and their derivatives and salts and combinations. Permeation enhancer as comprises a metal chelator, such as EDTA, EGTA, a surfactant, such as sodium dodecyl sulfate, polyethylene ethers or esters, polyethylene glycol-12 lauryl ether, salicylate polysorbate 80, nonylphenoxypolyoxyeth-ylene, dioctyl sodium sulfosuccinate, saponin, palmitoyl carnitine, lauroyl-l-carnitine, dodecyl maltoside, acyl carni-tines, alkanoyl cjolline and combinations. Other include but not limited, 3-nitrobenzoate, zoonula occulden toxin, fatty acid ester of lactic acid salts, glycyrrhizic acid salt, hydroxyl beta-cyclodextrin, N-acetylated amino acids such as sodium N-[8-(2-hydroxybenzoyl)amino]caprylate and chitosan, salts and derivatives and any combinations.

Other enhancers include: formulations of water in oil, formulations of oil in water; emulsions, double emulsions, micro-emulsions, nano-emulsions, water in oil emulsions, oil in water emulsions; steroidal detergent, an acylse; to allow better absorption in the mucosal tissue, better perme-ation and absorption in the target cells, better stability of the encapsulated drug/active ingredient.

Some embodiments comprise, either alone or in combi-nation with a penetration enhancer, a mucoadhesive agent such as, but not limited to, bioadhesive proteins, carbohy-drates and mucoadhesive polymers In the capsule of the present invention, the device com-prises at least one compartment, and preferably a plurality of compartments, each containing a flowable substance. The delivery device is designed to rupture the compartments such that the flowable substances are mixed with a carrier, preferably air, and delivered to a predetermined deposition site, typically, but not exclusively, in the nasal passages.

Medicaments may be supplied as liquids, as powders, or as aerosols. In the preferred embodiment, the medicament is supplied in a single-dose capsule. In other embodiments, the medicament is supplied in a multi-dose capsule means, the multi-dose capsule adapted to provide a single dose per activation.

In preferred embodiments, the flowable-substance cap-sule has a plurality of compartments. A compartment can contain at least one medicament, at least one medicament precursor, carrier gas, compressed gas, and any combination thereof.

The different compartments can contain different medi-caments, with the plurality of medicaments delivered to the nostril or other delivery site in a single dose. In this manner, a plurality of medicaments may be supplied to the nostril in a single injection, with interactions occurring between the medicaments at most during the short time between activa-tion of the device and the delivery of the substances and their deposition at the target site.

In some embodiments, interactions between components are unwanted. In such embodiments, a sequential release will utilize the short time period between release of the components and their absorption in the body to prevent such unwanted interactions and/or reactions.

In other embodiments, mixing and/or reactions are desired. In such embodiments, the reactions can occur all at once, by rupturing all of the compartments at the same time and mixing/interacting the components, either in the aerosol or in at least one mixing chamber. In other embodiments, a component can be added by needle insertion at a desired time before use, either into an empty compartment or into an occupied compartment (so that a desired reaction can occur). In other embodiments, the compartment walls rupture in a predetermined order, so that mixing/interaction occurs in stages, in a predetermined order. Mixing/interaction can occur in a compartment or compartments, in a mixing chamber, in the air passages of the device, in the aerosol, in the nasal (or other) passages of the body, and any combi-nation thereof.

As a non-limiting example, a medicament can comprise four components, stored in four compartments of a capsule. Prior to activation, a fifth component is injected into com-partment 1. After a predetermined time, the device is acti-vated and the walls between compartment 1 and compart-ment 2 are broken, allowing mixing of 5/1 and 2. This followed by rupture of the walls surrounding component 3, which then mixes with 5/1/2 and reacts with 2. The last walls to rupture are those surrounding compartment 4; material 4 remains in a separate part of the aerosol and deposits on the nasal passages after deposition of 5/1/2/3.

In another example, precursor A mixes with precursor B to form intermediate C, and, subsequently, intermediate C mixes with precursor D to form final product E.

Mixing or reactions or release of components from dif-ferent compartments can occur simultaneously, in different linked compartments, or they can occur sequentially, as in the example above. Any combination of sequential and simultaneous reactions and/or mixing and/or release can be used. Components can arrive at the deposition site simulta-neously, either mixed or unmixed, sequentially, and any combination thereof.

It should be noted that there can be a predetermined delay of some fractions of a second between rupturing of walls of different compartments, in order to, for non-limiting example, allow complete mixing of one set of components or allow a reaction between one set of components to go to completion before the next mixing/reaction starts or the delivery starts.

In some embodiments, the device or, preferably, the capsule, comprises a mixing mechanism or mixing chamber, so that, as described above, components of the composition can mix and/or react during the activation process, enabling components to be stored separately and/or to be stored as stable precursors, but to deliver a predetermined treatment comprising at least one medicament to a predetermined delivery site. An embodiment of a mixing mechanism in a mixing chamber is disclosed hereinbelow (see FIG. 26, below).

Figure 24:
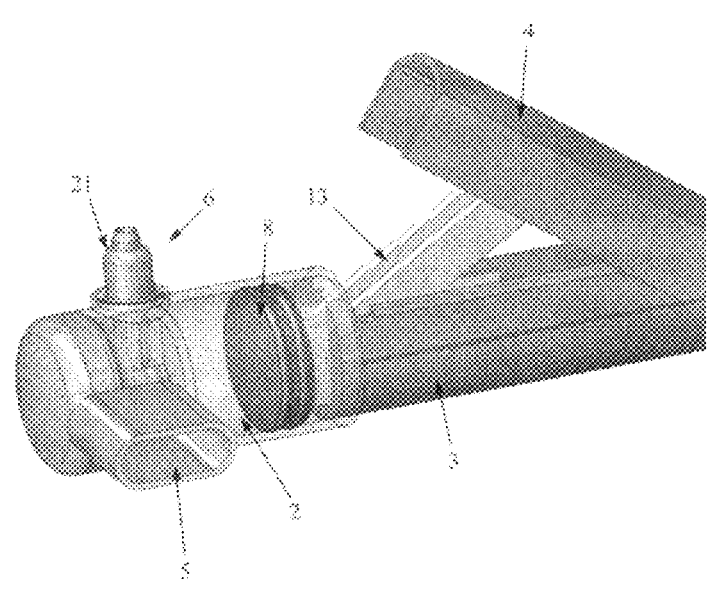
FIG. 24 schematically illustrates an embodiment of a device to deliver a predetermined amount of a substance to a natural orifice of the body.

An exemplary and non-limiting embodiment of part of a delivery device is illustrated in FIG. 24. In this embodiment, the nosepiece (6), the capsule (21) and the mouthpiece (5) are removable, and the handle (4) pivots about the lower end of the proximal end (3). In this embodiment, the piston driver (13) does not comprise a hinge, enabling it to be manufactured as a single piece.

In FIG. 24, the handle (4) is illustrated in the open position (i.e., the extended position).

In some embodiments, the capsule comprises a nosepiece (6) and at least one medicine compartment (21) as a single unit, which is removable and replaceable. In some embodi-ments, this a single-use unit, where the medicine compart-ment (21) is not refillable, the unit being discarded after use. In other embodiments, the device (21) comprises a cartridge of medicine capsules, with means to replace an exhausted capsule with an unused one. In some variants of this embodiment, the cartridge can be replaced. In other variants, the cartridge is single-use, the nosepiece unit (6) being discarded when the cartridge is exhausted. In yet other embodiments, the nosepiece (6) and capsule (21) form two units, enabling replacement of either the nosepiece (6) or capsule (21), as appropriate.

The capsule can be single-use, comprising at least one of a substance, a carrier, a compressed gas, a propellant, and any combination thereof. Similarly, a multi-dose cartridge can comprise multiple capsules, each capsule comprising at least one of a substance, a carrier, a compressed gas, a propellant, and any combination thereof.

The capsule can be single-compartment or can comprise at least two compartments. In some embodiments, at least one compartment contains a propellant such as compressed air (air compartment). In such embodiments, charging is enabled by causing the compressed air to flow from the at least one compressed air compartment into a compressed air chamber in the device, said compressed air chamber fluidly connected to an air channel (not shown). An illustrative example of a method of causing the compressed air to flow from at least one compressed air compartment into the compressed air chamber in the device comprises a port on the enclosure such that, when the flowable substance chamber is mounted to the enclosure, the port is enabled to fluidly connect the at least one compressed air compartment to the compressed air chamber. Retracting the handle (4) or placement of the capsule in its capsule retainer position causes a piercing means to pierce a wall of the at least one compartment of the capsule, causing the air to flow from the at least one compressed air compartment into the at least one flowable substance chamber of the capsule. Many other methods of causing the compressed air to flow from the at least one compressed air compartment through the other compartments and to the deposition site will be obvious to persons with ordinary skill in the art.

In any of the devices described herein, an indicator element can be used to indicate to the user that the device has been charged to the desired pressure, to the desired volume and any combination thereof.

In any of the devices described herein, active feedback with a correction element can be used to indicate to the user whether the desired volume, pressure and any combination thereof has been reached, or to ensure that the desired volume, pressure and any combination thereof have been reached and any combination thereof.

In preferred embodiments, there is a positive means of ensuring that the device is properly charged before activation. In some embodiments, proper charging is ensured by having the direction of handle movement opposite to the power produced by the pressurizing action, thus enabling the finalization of the charging of the device. In other embodiments, the user pulls a string tight to finalize the charging action of the device. In yet other embodiments, the device comprises a magnet which creates a magnetic field between the piston and the end point of charging or at another position predetermined position. This magnetic field contributes to the finalization of the charging action. An electrical field could act in a manner similar to the magnetic field.

FIGS. 25A-25E show exemplary embodiments of multi-compartment capsules.

In multi-compartment capsules, walls divide the capsule into compartments. The compartments can have approximately the same volume or different volumes, and the same thickness or different thicknesses; if circular, they can have the same diameter or different diameters. They can have the same area at the end faces, or different areas.

The compartments, taken together, can form a large fraction of the volume of the capsule, or they can form a small fraction of the volume of the capsule.

Compartment walls can be equally spaced, either angularly or linearly, or they can be unequally spaced. Spacings can be arbitrary, they can be regular, they can follow a pattern, and any combination thereof.

Compartments can be near the edge of the capsule or at other positions within the capsule.

Before use, the compartments are preferably hermetically sealed to prevent mixing of the substances contained therein.

Compartment walls can be substantially similar in shape to the capsule walls (for non-limiting example, lenticular walls within a lenticular capsule) or at least one of the compartments' walls' shape differs from the shape of the cross-section of the capsule. (For non-limiting example, a lenticular wall within a circular capsule.)

Compartment walls can be non-frangible or frangible. Frangible walls permit mixing or reaction of the contents of adjacent compartments before the substances leave the compartments.

Compartments can, but need not, have a frangible membrane at at least one end.

Any compartments can contain one substance or a mixture of substances; any two compartments can contain the same substance or mixture thereof, or different substances or mixtures thereof.

The material of any combination of capsule walls and compartment walls can be rigid, semi-flexible, flexible and any combination thereof. Flexible or semi-flexible compartment or capsule walls can reduce dead space—regions of low gas flow—in the air path during activation.

Figures 25A, 25B, 25C, 25D:
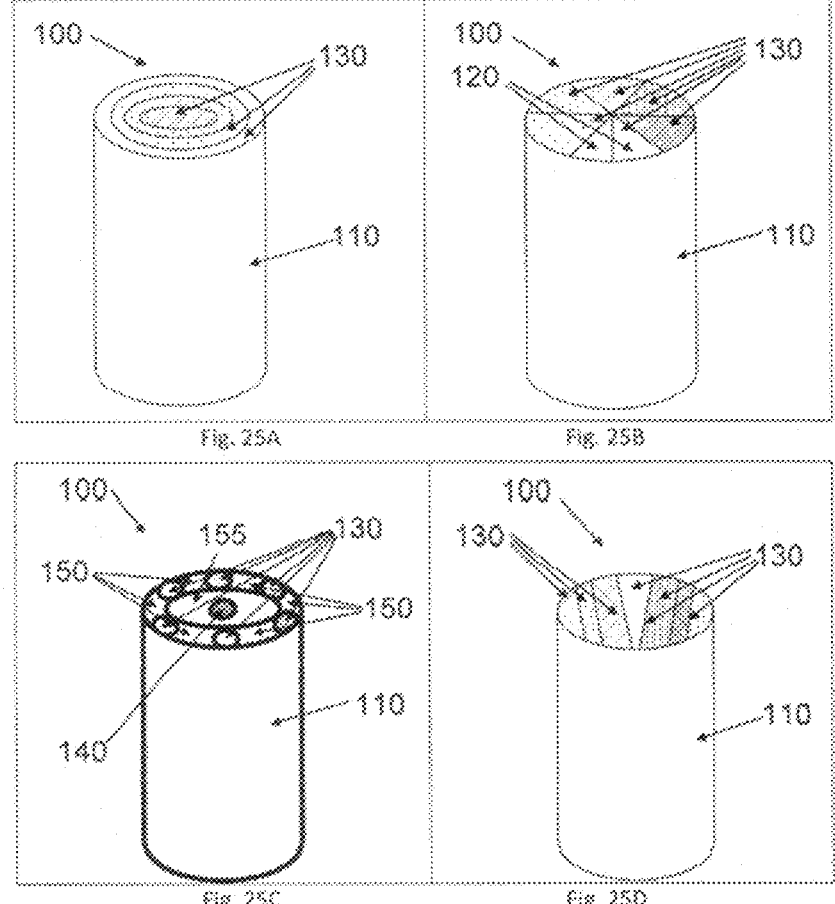
FIGS. 25A, 25B, 25C, 25D and 25E schematically illustrate embodiments of containers (also refers as capsules) to contain the substance.

In the embodiment shown in FIG. 25A, the compartments (130) are coaxially disposed within the outer tegument (110), with the compartments nested within one another. The central compartment forms a cylinder and the remaining compartments, three in the exemplary embodiment of FIG. 25A, each forming an annulus of a cylinder. Nested compartments need not be coaxial.

In the embodiment schematically illustrated in FIG. 25B, the capsule (100) comprises an outer tegument (110) enclosing n angularly disposed compartments (130) separated by walls (120), where n is less than about 10. In the embodiment shown in FIG. 25B, n is e.g., six.

In the embodiment schematically illustrated in FIG. 25C, the capsule (100) comprises an outer tegument (110) enclosing six angularly disposed cylindrical compartments near the edge of the capsule (130), a central compartment (140), and auxiliary compartments (150, 155), for a total of 14 compartments.

In practice, the embodiment illustrated in FIG. 25C will have no more than about 20 compartments.

In some embodiments, there is no central compartment (140).

In the exemplary embodiment shown, the auxiliary compartments are hollow, containing a substance. In other embodiments, at least one of the auxiliary compartments (150, 155) is comprised of solid material, thereby forming part of the structure of the capsule.

In preferred embodiments, the central compartment (140) and the central auxiliary compartment (155) are solid, forming a solid central core for the structure. The remaining compartments (130, 150) comprise substance, where, in preferred embodiments, the compartments (130) contain a substance such as a medicament and the auxiliary compartments (150) contain a propellant, preferably compressed gas.

In the exemplary embodiment shown in FIG. 25D, the compartments (130) form slices within the outer tegument (110). In the exemplary embodiment of FIG. 25D, some of the slices have parallel sides, while the central slice is wedge-shaped; in other embodiments, all of slices have substantially parallel sides. In yet other embodiments, a plurality of slices are wedge-shaped. Slice-type capsules can have up to about 10 compartments.

Figure 25E:
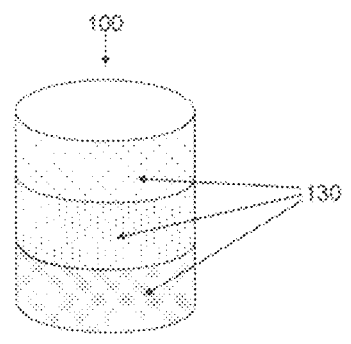

In the exemplary embodiment shown in FIG. 25E, the compartments (130) are arranged longitudinally, with the walls between the segments being frangible. Any number of such compartments can be used and the lengths of the compartments can differ.

These embodiments are merely exemplary; any combination of the above arrangements can be used.

In the exemplary embodiments shown, the walls separating the compartments are planar. In other embodiments, the walls can form a curve, either regular or irregularly shaped.

The main longitudinal axis of at least one of the compartments can be parallel to the main longitudinal axis of the capsule, it can be spirally disposed it can be at an angle to the main longitudinal axis of the capsule, and any combination thereof.

The main longitudinal axes of the compartments can be straight, they can form regular curve, they can form irregular curves, and any combination thereof. For any pair of compartments, the main longitudinal axes can be the same or they can be different.

In most embodiments, at least part of the upstream closure surface (not shown) and the downstream closure surface (not shown) of the capsule are frangible or otherwise removable, such that, when broken or otherwise removed, the medications can be delivered to the desired deposition site. In a variant of these embodiments, different portions at least one closure surface have different breaking strengths, such that the different portions can be broken at different times during delivery of the medication, enabling either differential mixing of medical formulations in different compartments or differential delivery of the medications in at least two of the compartments.

In some embodiments, at least part of the side surface of the capsule is frangible, enabling yet another mixing path or delivery path.

Capsules can be cylindrical with circular cross-section, as shown, cylindrical with oval, elliptical, lenticular, or polygonal cross-section, with the polygon having at least three sides and not more than about 20 sides. The polygon can be a regular or irregular.

Capsules can be spherical, elliptical, ovoid, pillow-shaped, football-shaped, stellate and any combination thereof. Capsules can form regular or irregular shapes.

Compartments can have substantially constant cross-section through the device or the cross-section can vary in area, in shape, or in any combination thereof.

Figure 26:
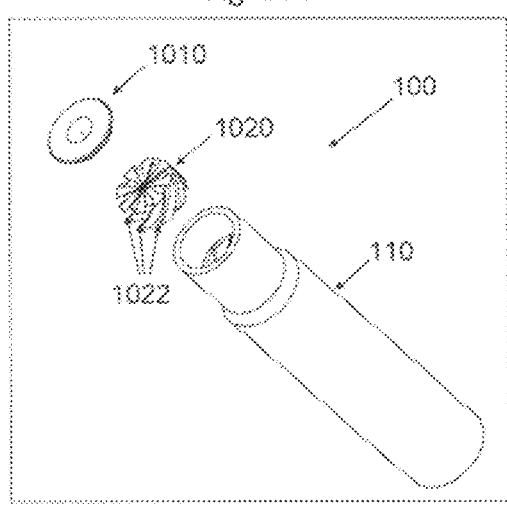
FIG. 26 schematically illustrates a mixing chamber in a capsule.

FIG. 26 shows a schematic of an exploded view of an embodiment of a mixing chamber in a capsule, the part of a capsule adapted to mix components in a composition. In this exemplary embodiment, the tegument (110) of the capsule and the upstream closure surface (1010) of the capsule are shown. Also shown is a mixing mechanism (1020), in this case, a single-section mechanism. The substance compartments are not shown.

In this exemplary embodiment, the mixing mechanism (1020) comprises spirally-disposed air channels (1022) at the periphery of the mixing mechanism (1020). The central part of the mixing mechanism (1020) is solid, forcing the carrier gas and the substances to pass through the channels (1022). By narrowing the channel through which the gas passes and by changing the direction of the gas flow, mixing of the substances is enhanced. The mixing mechanism (1020) fits within the tegument (110) of the capsule (100) and mixing occurs within the capsule (100).

In some embodiments, the capsule comprises two units, one comprising at least one substance and one comprising the mixing mechanism, such that the substances exit the compartments and are then mixed in the mixing mechanism.

In other embodiments, the mixing mechanism (1020) comprises channels disposed throughout its cross-section.

Channels can be arbitrarily arranged across a cross-section, regularly arranged across a cross-section, or irregularly arranged across a cross-section.

Channels can be linearly disposed, parallel to the main longitudinal axis of the capsule; or linear and disposed at an angle to the main longitudinal axis of the capsule.

The main longitudinal axis of at least one channel can be curved with respect to the main longitudinal axis of the mixing mechanism, with respect to an axis perpendicular to the main longitudinal axes, or any combination thereof.

Any combination of the above channel shapes can be used.

The shape of a channel cross-section can be substantially the same along the length of the channel, the shape can change along the length of the channel, the size of the cross-section can change along the length of the channel, and any combination thereof.

Shapes of the cross-sections of the channels can vary in the same manner along the length of the channel, or they can vary in different manners.

Shapes of the cross-sections of the channels can be the same for all the channels, or the shapes of the cross-sections of at least two channels can be different.

Sizes of the cross-sections of the channels can vary in the same manner along the length of the channel, or they can vary in different manners.

Sizes of the cross-sections of the channels can be the same for all the channels, or the sizes of the cross-sections of at least two channels can be different.

In some embodiments, the mixing mechanism (1020) comprises a plurality of longitudinal sections, with the sections having fluidly connected channels, but the channels are differently disposed longitudinally. For non-limiting example, a two-section device can have spirally disposed channels with left-handed spirals in the first section and right-handed spirals in the second section.

In some embodiments, there are different numbers of channels in the two sections. In other embodiments, there are the same number of channels in the two sections.

In other multi-section mixing mechanisms (1020), sections comprising channels are fluidly connected by substantially channel-free regions.

Mixing mechanisms can comprise between 1 and 10 regions. Individual regions can have any of the channel dispositions described hereinabove.

In some embodiments, mixing can be done by an integral mixing mechanism, either a single-section or a multi-section device. In other embodiments, mixing can be done by disposing a plurality of single-section mechanisms end-to-end, either abutting each other or with spacers to provide channel-free regions.

During the process of mixing, the first and second flowable substances can be mechanically mixed with each other and with the air, they can be reacted with each other, and any combination thereof.

In some embodiments, reaction of at least one flowable substance can be enhanced by a catalyst deposited on or part of the walls of the mixing region.

Criteria of the capsule can be adjusted to include: ensuring that a single dose of the substance is delivered in its entirety, ensuring that the single dose contains the predetermined amount of the substance, ensuring that the dose is delivered to the desired region of the nose, and ensuring that delivery of the dose causes the minimum possible discomfort to the patient. Any combination of these criteria can be adjusted to enhance performance for each particular combination giving rise to a different embodiment of the capsule.

The capsule can also be adapted for ease of insertion into a delivery device, for ease of removal from a delivery device, for stability of the contents during storage, for resistance of the capsule materials to environmental degradation, for resistance to undesired fracture, for reliability of use, for completeness of mixing, for completeness of reaction, and any combination thereof.

In some embodiments, the capsule comprises a filter adapted to remove from the air at least one selected from a group consisting of particles, particulates, bacteria, viruses, moisture, and undesired gases before the air contacts the user. Such a filter, by preventing unpleasant odors or tastes from reaching the user and by preventing particles or particulates from reaching the user, can make the experience of using the device much more pleasant for the user and much safer. By removing bacteria and viruses, infection of the user can be prevented.

In some embodiments, the capsule contains only a single dose of the substance, the capsule being replaced after each use. In other embodiments, the capsule contains multiple doses of the substance, preferably packed separately, so that the dose is fresh for each use.

It should be emphasized that any embodiment of the present invention and any variant thereof can be used for both for humans (medical use) and animals. Thus, any of the devices as disclosed above and any variant thereof can be used for veterinary applications as well as (human) medical applications.

During dispensing of the substance, the gas passing through the capsule entrains the substances contained within the compartments such that the substances have a predetermined distribution within the dispensed mixture, where the predetermined distribution can be a homogeneous distribution or a heterogeneous distribution. Heterogeneous distributions can be: an arbitrary distribution, a distribution in which the density of the at least one substance within the mixture follows a predetermined pattern, and any combination thereof.

According to another embodiment of the present invention, movement of air into the chamber during transformation of the device into said pre-activated state creates a vacuum in the region near or in the capsule.

In some embodiments the substance is a composition which can contain at least one drug, at least one chemical permeation enhancer, and any combination thereof. The composition can be a gel, a solution, a cream, a spray, a powder, a tablet and any combination thereof.

In preferred variants of this embodiment, chemical penetration enhancers, mucoadhesive agents, and any combination thereof increase the rate of absorption of at least one of the drugs in the formulation at the site of delivery, relative to rate of absorption of that drug at the site in a composition lacking the chemical permeation enhancers.

The characteristics of the formulation and/or of the chemical penetration enhancers are chosen so that the chemical permeation enhancers are unable to cause either necrosis or specific inflammation at the site of delivery and are further unable to cause symptoms associated with unwanted side effects.

In some variants of these embodiments, a chemical permeation enhancer or a combination of enhancers is adapted to deliver drugs into epithelial cells. The chemical permeation enhancer for delivery into epithelial cells can be a zwitterionic surfactant, palmityldimethyl ammonio propane sulfonate (PPS) or a structural analog thereof, a nonionic surfactant, polysorbate 20, polysorbate 40, polysorbate 60, or polysorbate 80 and any combination thereof.

The site of delivery of the chemical permeation enhancer for delivery into epithelial cells can be a mucosal layer selected from a group consisting of mucosa of body orifices and mainly the nasal cavity mucosa.

In some variants of these embodiments, a chemical mucoadhesive element is tailored to allow better target tissue deposition and adherence to allow better delivery with slow release characteristics for prolonged tissue exposure to the active ingredient.

Example 1

An embodiment of a pressurized air carrier for providing controlled drug delivery to the nasal cavity.

Other embodiments can be used for delivery to the ear, mouth, throat and rectum.

In this embodiment of the device, the following parameters were variable, over the ranges given:

Pressure, between about 1 bar and about 20 bar

Air volume, between about 1 cc and about 50 cc

Time between charging and activation, more than 0.1 sec

Another important consideration, not investigated in this example, is the location of the nozzle in the body orifice, for non-limiting example, the depth of insertion of the nozzle in the nasal cavity.

In practice, at least one of: the pressure, air volume and time between charging and activation can be selected based on the characteristics of the compound, drug or medicament such as, but not limited to, the volume, density, viscosity, state of matter, drug formulation, and any combination thereof. The compound can be a liquid, a powder or any combination thereof.

Pressure, air volume, time between charging and activation, and location in the orifice interact with the characteristics of the delivered substance; all of the above contribute to the final distribution of aerosolized matter in the nasal cavity, or, in other words, the pattern of deposition of the aerosolized matter in the nasal cavity following discharge of the matter from a device with given predetermined parameters.

Other criteria which can be adjusted to enhance performance include, but are not limited to, droplet size, droplet size distribution, droplet size as a function of time, and droplet size distribution as a function of time.

The material as delivered is then a predetermined volume of the selected medicament in a predetermined form within a carrier comprising a predetermined volume of air, with the volume of air delivered at a predetermined pressure.

Tests showing the effect of changing pressure, air volume and time between charging and activation are given below. Deposition was measured in models that mimicked at least one aspect of the human nasal cavity (structure, friction, air flow, surface area or surface mucosa).

Model 1

A 36 cm long plastic tube with an inner diameter of 0.6 cm was used as a model for nasal friction and air resistance in the nasal cavity. The length of the aerosol distribution was measured, as well as the characteristics of the aerosol distribution.

2 mg/ml Methylene Blue in saline was used. The dye distribution pattern in the tube and the amount of dye that reached the end of the tube were observed.

Figure 27:
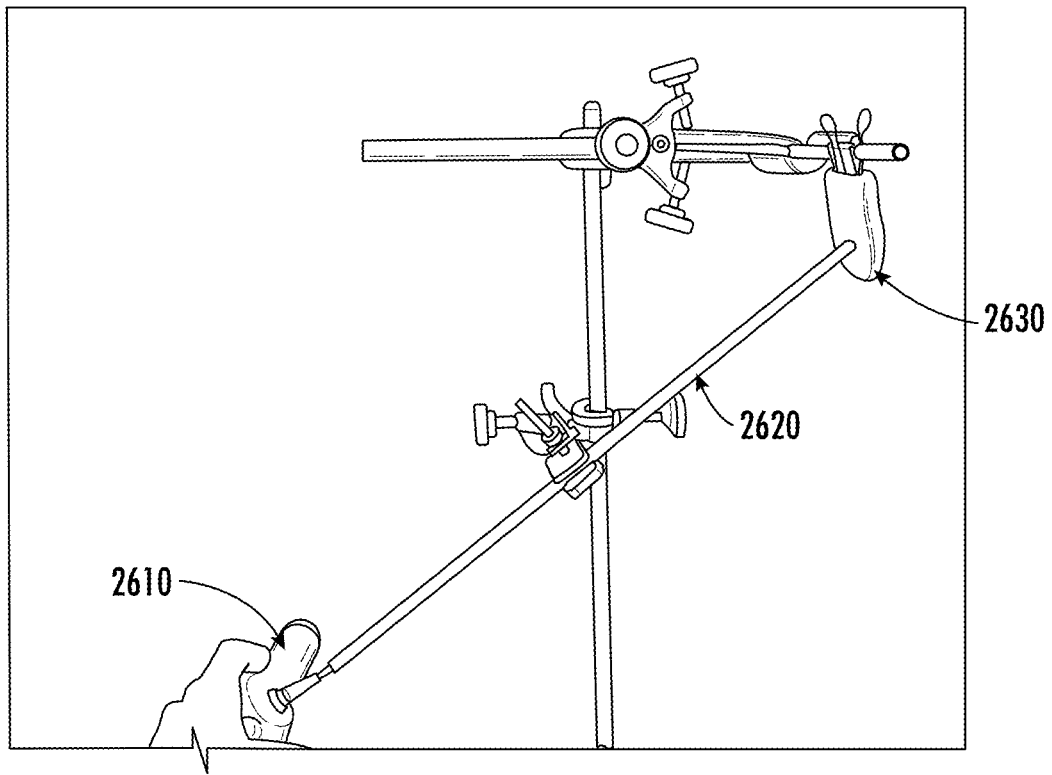
FIG. 27 illustrates a test setup for testing embodiments of the device.

In reference to FIG. 27, a test setup is shown, showing a delivery device (2610), the plastic tube (2620), and an absorbent pad (2630) to capture material that has passed entirely through the tube.

In reference to FIGS. 28A-28B, a pressure of 4 bar and a liquid volume of 100 microliters were used for the tests. An air volume of 18 cc was used for the two results shown in FIG. 28A, while an air volume of 10 cc was used for the two results shown in FIG. 28B.

Delivery of the liquid dye through the end of the tube (2620), as determined by its deposition on the absorbent (2630), was more efficient for the air volume of 18 cc, as shown by the stronger color (showing more deposited material) and more-even distribution in FIG. 28A as compared to FIG. 28B.

Figure 29A:
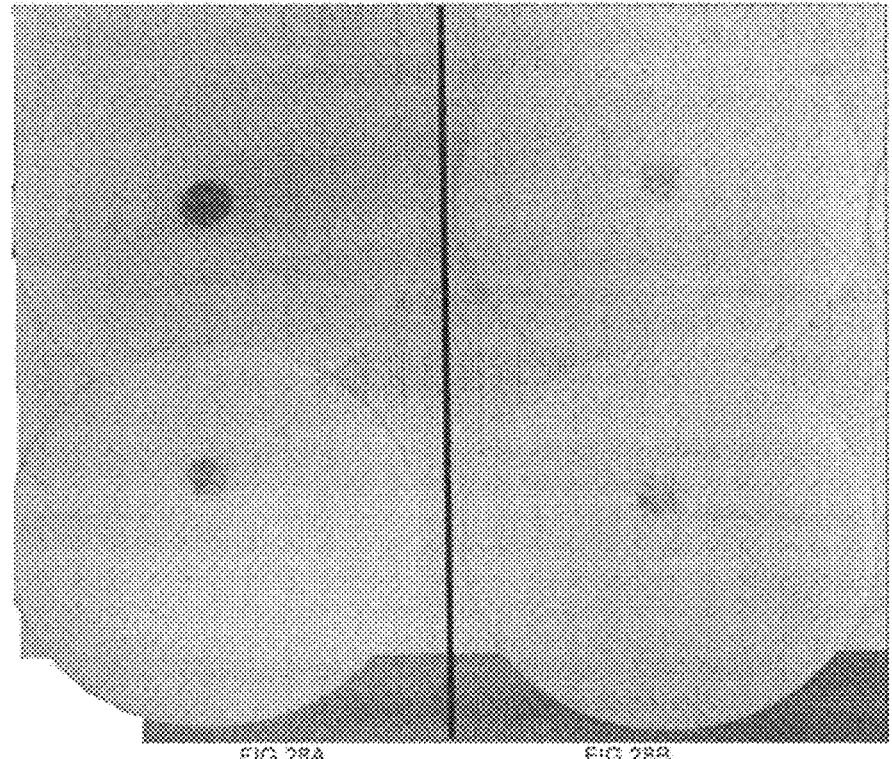
Figure 29B:
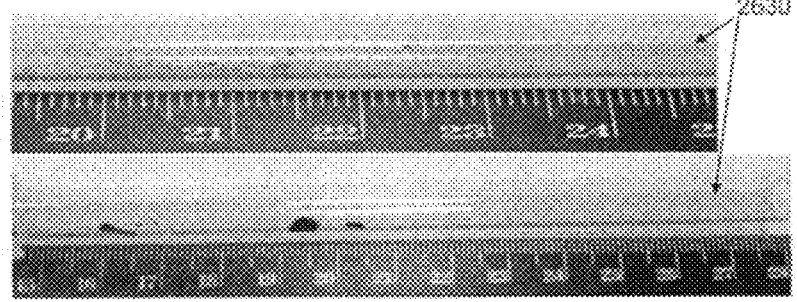

In reference to FIGS. 29A-29B, the deposition characteristics on the inner tube surface were much better for the 18 cc air volume (FIG. 29A) than for the 10 cc volume (FIG. 29B), with deposition of aerosol on the inner tube surface being much more homogeneous, being delivered over a longer distance and having much smaller droplets with the 18 cc air volume (FIG. 29A) than with the 10 cc air volume (FIG. 29B).

In reference to FIGS. 30A-30B, a pressure of 2 bar and a liquid volume of 100 microliters were used for the tests. An air volume of 14 cc was used for the two results shown in FIG. 30A, while an air volume of 5 cc was used for the two results shown in FIG. 30B.

Similarly to the results for FIGS. 28A-28B, delivery of the liquid dye through the end of the tube (2620), as determined by its deposition on the absorbent (2630), was more efficient for the air volume of 14 cc, as shown by the stronger color (showing more deposited material) and more-even distribution in FIG. 30A as compared to FIG. 30B.

In reference to FIG. 31A-31D, an air volume of 20 cc, a pressure of 7 bar and a liquid dye volume of 100 μl was used for the tests. In these tests, the device was charged; a time of 0.5 min (FIG. 31A), 5 min (FIG. 31B), 50 min (FIG. 31C), and 150 min (FIG. 31D) was allowed to elapse; and the device was activated. As can be seen from FIG. 31A-31D, the elapsed time between charging the device and its activation has virtually no influence on the results, indicating that the device can remain in the charged state for a prolonged period prior to activation and drug release.

Model 2

A nasal cast model was used to provide a more realistic comparison to the average human nasal cavity. Material dispersion and penetration into the nasal cavity layers was found to be dependent on the pressure and air volume and the form and characteristics of the material deposited.

FIG. 32 shows the effect of pressure (with other parameters held constant) on deposition of a powder. More than 2½ times as much powder reached the olfactory epithelium with the 8 bar pressure, compared to the 4 bar pressure.

Model 3

The effects of air volume and air pressure on the distribution of 99mTC-DTPA aerosol in the nasal cavity and nasopharynx were examined using SPECT-CT for two human volunteers.

In both cases, the deposited material comprised 300 microliters of DTPA; 1.75 mc (milli Ciri) and the air volume was 20 ml. A pressure of 6 bar was used for the results shown in FIG. 33A, while a pressure of 4 bar was used for the results shown in FIG. 33B.

In FIG. 33A, the aerosol is localized in the nasal cavity at the respiratory and olfactory epitheliums (dashed arrow) and did not reach the Nasopharynx and did not enter the GI tract. In FIG. 33B, with a lower pressure, the aerosol is localized in the nasal cavity at the respiratory and olfactory epitheliums and also moved down into the Nasopharynx (upper dotted arrow) and into the GI tract (lower dotted arrow).

The pressure affected the distribution and thus the absorption of the aerosolized drug in the human body.

As shown hereinabove, the location and distribution of deposition of a desired substance and the characteristics of the substance on deposition are controllable by controlling parameters such as pressure, air volume, substance volume and nozzle shape.

Example 2

In contrast to prior-art nasal delivery devices and technologies, the devices of the present invention can produce a fine aerosol in the nasal cavity or other desired body orifice at the target area and at the location of the target tissue instead of within the device or immediately after exit from the device. Utilizing the pressure as a driving force and the air as a carrier allows the material to be released from the nozzle as a combination of material in a pre-aerosolized state and an aerosol. The properties of the resultant aerosol are typically dependent on the properties of the device and of the medium into which the device is discharged. The properties of the device which affect the aerosol characteristics are the delivery pressure, the volume of the delivery gas, and the characteristics of the delivery orifice.

In some embodiments, the aerosol properties are fairly independent of the delivered substance, in other embodiments, the pressure, volume, orifice characteristics and delivered substance properties can be co-optimized.

In prior-art devices the aerosol is produced at the exit to the device. Typically, the aerosol comprises a wide dispersion of particle sizes, a wide "fan" of aerosol and a low driving force. Therefore, the large droplets typically deposit very close to the exit from the device; smaller droplets tend to quickly contact the walls of the passage, so that deposition is typically predominantly close to the exit from the device, with little of the substance reaching desired sites deeper in the orifice, such as the turbinates of the nose, In contrast, in the present device, the pre-aerosolized mixture of gas and substance exits the device with a significant driving force, when the preaerosolized fluid hits the walls of the nasal passages, it "explodes" into a fine aerosol that is capable of being driven by the pressure deep into the nasal passages to deposit in the desired region.

Figures 34A, 34B, 34C, 35A, 35B, 35C, 35D:
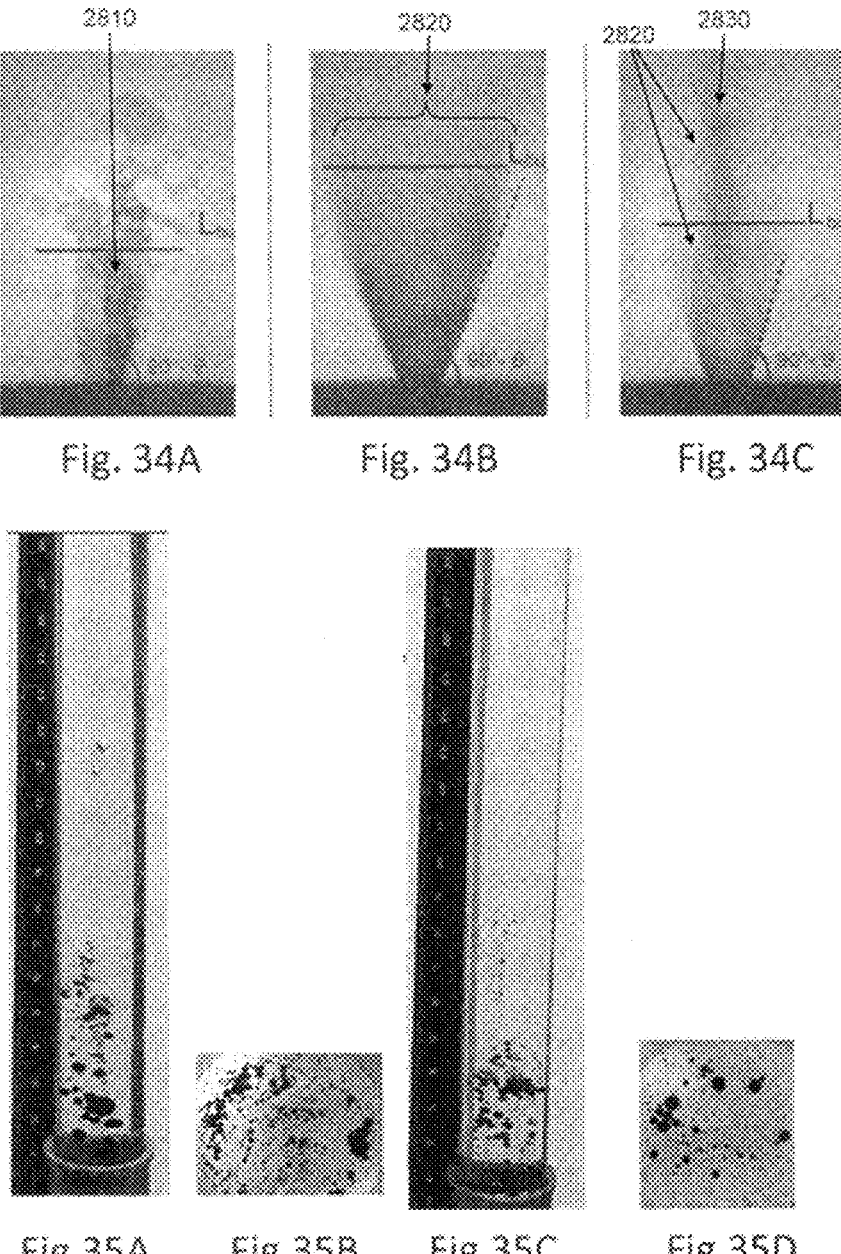

The following example will illustrate a typical aerosol dispersions. FIGS. 34A-34C shows typical aerosol dispersions. FIG. 34A shows a distribution of the dispensed material commonly seen in the prior art. In FIG. 34A, the distribution is narrow (θ is small; 90-θ is large) and asymmetrical; the distribution of material in space (2810) is very uneven and there is a wide dispersion of droplet sizes, including large droplets that commonly deposit in undesired places. FIG. 34B shows a fine mist produced from the device orifice (2820) with an even distribution of material in space, and a relatively narrow dispersion of droplet sizes, while FIG. 34C shows an aerosol with a thread-like stream (2830) which sheds an even fine aerosol (2820) to its surroundings. The aerosol of FIG. 34C is typical of the aerosols generated by the present invention for deposition in the upper portions of the nasal passages.

Example 3

In all known other mechanisms of creating aerosols, an orifice is placed at the end of a nozzle and the inner diameter of the device's nozzle and, especially, its orifice, is the main parameter that influences aerosol formation and the aerosol's characteristics. In contrast, in the present invention, no orifice is needed. More than that, putting a conventional orifice at the end of the nozzle will actually limit the pressure and the forces reaching the liquid or powder being dispensed, and thus will reduce the ability to create the desired fine aerosol at the target site. Thus, the large diameter tubing that can be used in the present invention, about an order of magnitude larger than the diameter of commonly-used tubes and orifices, results in the desired fine aerosol, carried efficiently into the nasal cavity with droplet diameters on the order of 0.1-50 micrometer.

In the present invention, the aerosol is created as a result of the nasal cavity resistance and is influenced by the air volume-pressure parameters of the device rather than primarily by the orifice diameter.

In order to model nasal friction and air resistance and as a model for aerosol formation in the nasal cavity, a 36 cm long glass tube with an inner diameter of 2 cm, filled with oil up to 22 cm of its length, was used.

Theoretical analysis has indicated that 5 cm of tube is equivalent to about 0.1-0.5 cm of the nasal passages; therefore the 22 cm. tube would approximately simulate the full depth of a nasal passage.

The test material was 200 microliter of Methylene Blue liquid solution.

The liquid solution was discharged from a device into the base of the tube and pictures and videos were taken in order to be able to follow the process of aerosol formation. The length of the deposition region, the aerosol distribution and the diameter of the aerosol droplets were determined as a function of time.

FIGS. 35A-35D show the effect of orifice size on droplet size (FIGS. 35B, 35D) and droplet distribution (FIGS. 35A, 35C) in a conventional device.

The Methylene blue solution was injected into the tube using a syringe. FIGS. 35A-35B show droplet distribution and size for a larger needle (21G; approx. 0.5 mm) and FIGS. 35C-35D show droplet distribution and size for a smaller needle (25G; approx. 0.2 mm). The larger diameter needle (FIGS. 35A-35B) creates larger droplets than the smaller diameter needle (FIGS. 35C-35D).

In contrast, FIGS. 36A1-36D and 37A-37D show that the opposite is true if the technique of the present invention is used, where the aerosol is created by means of a pressurized gas.

In reference to FIG. 36, FIGS. 36A1-36D show the effect of orifice size on droplet size (FIGS. 36B, 36D) and droplet distribution (FIGS. 36A1, 36A2, 36C) in a device of the present invention. FIG. 36A1 shows the distribution in the lower part of the tube, while FIG. 36A2 shows the distribution in the upper part of the tube.

In FIGS. 36A-36D, the device of the present invention is charged to 7 bar pressure and 20 ml of Methylene Blue solution is discharged through an orifice into the base of the tube. FIGS. 36A-36B show droplet distribution and size for a larger needle (21G; approx. 0.5 mm) and FIGS. 36C-36D show droplet distribution and size for a smaller needle (25G; approx. 0.2 mm). In this case, the larger nozzle (FIGS. 36A, 36B) has smaller diameter droplets, a more homogeneous aerosol and a distribution that extends much further up the tube than the smaller diameter nozzle (FIGS. 36C, 36D).

In reference to FIG. 37, FIGS. 37A-37D show the effect of orifice size on droplet size (FIGS. 37B, 37D) and droplet distribution (FIGS. 37A, 37C) in a device of the present invention.

Figures 37A, 37B, 37C, 37D:
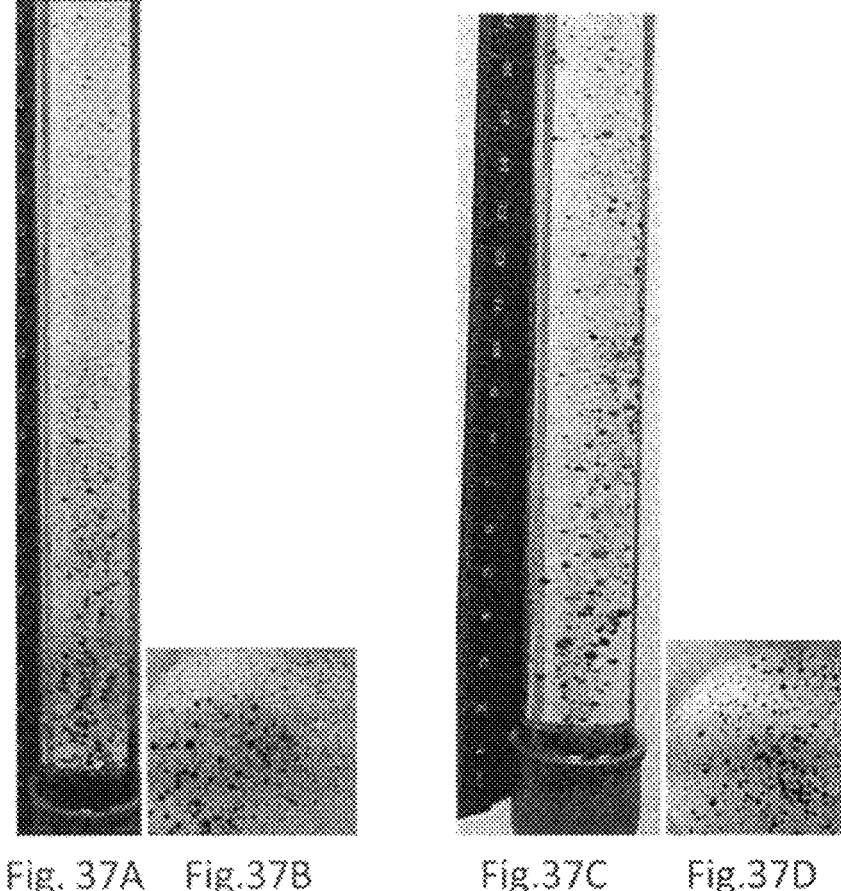

In FIGS. 37A-37D, the device of the present invention is charged to 4 bar pressure and 18 ml of Methylene Blue solution is discharged through an orifice into the base of the tube. FIGS. 37A-37B show droplet distribution and size for a larger needle (21G; approx. 0.5 mm) and FIGS. 37C-37D show droplet distribution and size for a smaller needle (25G; approx. 0.2 mm). In this case, the larger nozzle (FIGS. 37A, 37B) has smaller diameter droplets and a more homogeneous aerosol than the smaller diameter nozzle (FIGS. 37C, 37D).

Figure 38A:
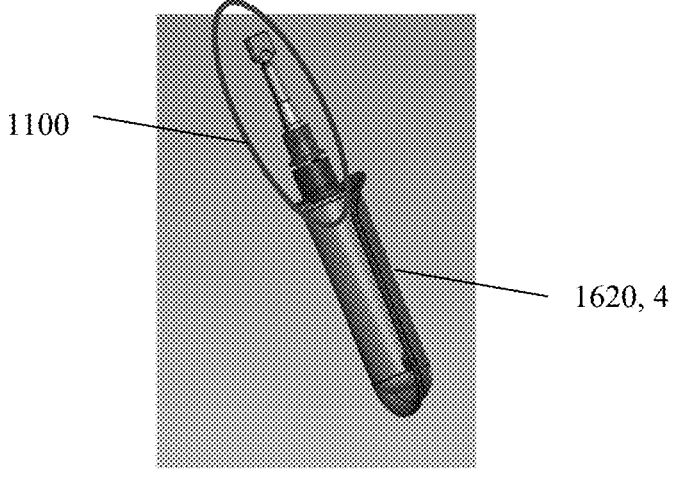
FIGS. 38a, 38b and 38c illustrate another embodiment of the present invention in which a multi-use device is utilized.
Figure 38B:
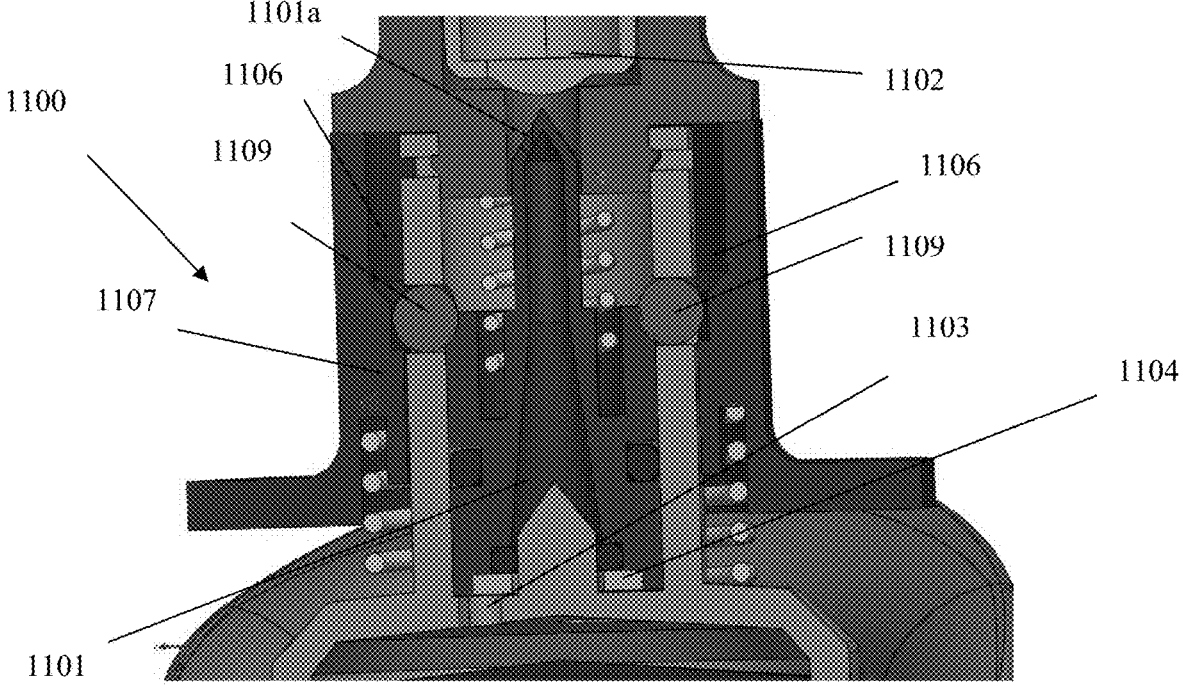
Figure 38C:
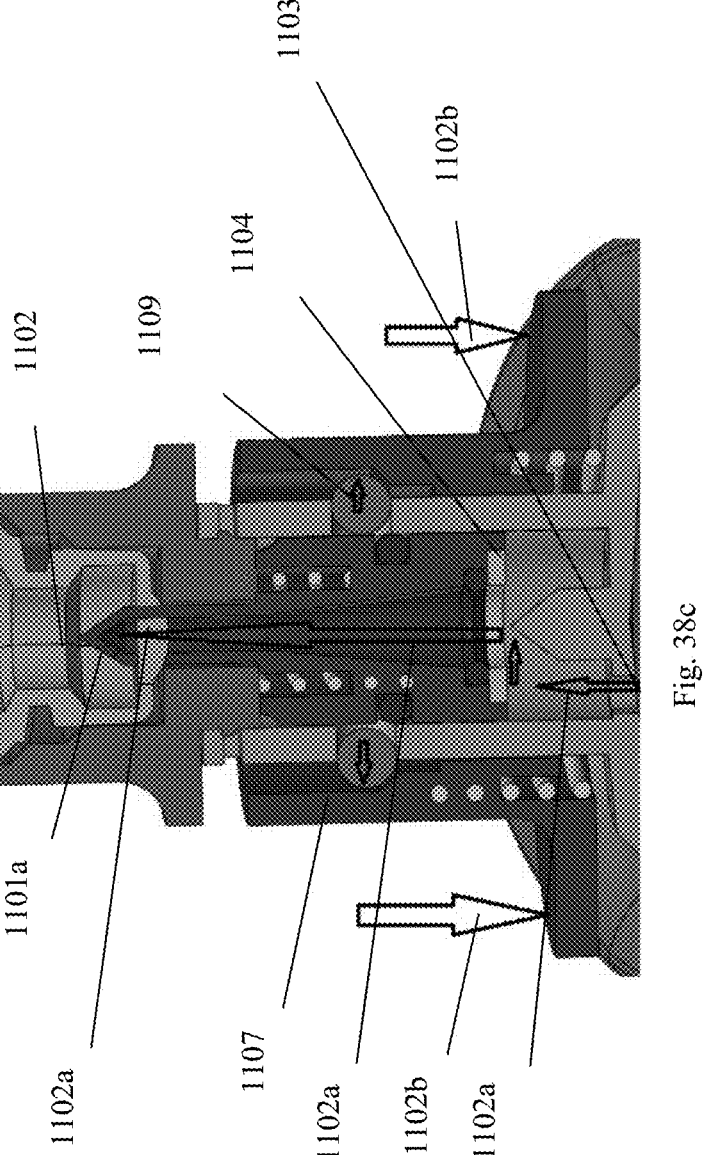

A comparison of FIGS. 36A1-36D and 37A-37D shows that the higher volume-higher pressure combination (20 ml, 7 bar) has smaller diameter droplets with a greater homogeneity and a distribution that extends much further up the tube than the lower volume-lower pressure combination (18 cc, 4 bar). Reference is now made to FIGS. 38*a*-38*c* which illustrate another embodiment of the present invention, in which a multi-use device is utilized.

According to this embodiment, the delivery end (nozzle or nosepiece) 1100 comprises two parts: (a) hollow piercing means 1101 (a piercer, a penetrator); and, (b) capsule (e.g., a blow-fill-seal) 1102 containing the medicament to be delivered.

It should be noted that the hollow piercing means 1101 comprises a sharp end, adapted to pierce the capsule 1102. Said sharp end comprises at least one opening 1101*a* (through which the pressurized gas will enter into the capsule 1102).

The bottom most part of the piercing means 1101 is in physical contact with the upper most part of the chamber and enables (along with at least one o-ring, as will be disclosed hereinafter) the sealing of the chamber.

The piercing means 1101 is in physical contact with at least one element (e.g., spherical element 1109) acting as a stopper to limit movement, which prevents the piercing means 1101 from being displaced.

It should be noted that according to this embodiment, the delivery end (nozzle or nosepiece) 1100 has an expanded area 1106 (into which the spherical element 1109 will be displaced, once the device is activated, as will be disclosed hereinafter).

As described above, the handle 4 (or the single side lever 1620) is rotated from the parallel position (FIGS. 11A, 11C) to the perpendicular position (FIGS. 11B, 11D), the same pulls the plunger head away from the delivery end (1100) and filling the chamber (1400) with gas. The handle is then rotated back to the parallel position (FIGS. 11A, 11C), compressing the gas and transforming the device (1000) into the activated configuration. The device can then be activated and release the compressed and pressurized gas (along with the medicament) to the nasal cavity.

Thus, after the handle (4) is rotated back to the parallel position (to compress the gas inside the chamber), the pressure rises inside said chamber. In this position the device is ready to be activated.

According to this embodiment, the chamber comprises at least one opening 1103 in its upper most part and at least one o-ring 1104 sealing the same.

Activating the device is performed by pressing activation button 1107 downwardly (see FIG. 38c). Once pressed, the spherical element 1109 is moved to a position in the expanded area 1106, thus allowing the piercing means 1101 (namely, needle) to pierce capsule (e.g., a blow-fill-seal) 1102.

In parallel, when the device is activated, the o-ring 1104 sealing the at least one opening 1103 is moved, thus, allowing the pressurized gas being held in the chamber to exit the same, enter into the hollow the piercing means 1101 and exit into the capsule 1102, entraining the medicament (held therewithin) and therefrom to the nasal cavity.

Reference is now made to FIG. 38c illustrating the flow of air 1102a (once the device is activated (pressing the activation button 1107 downwardly, see arrows 1102b).

Figure 39A:
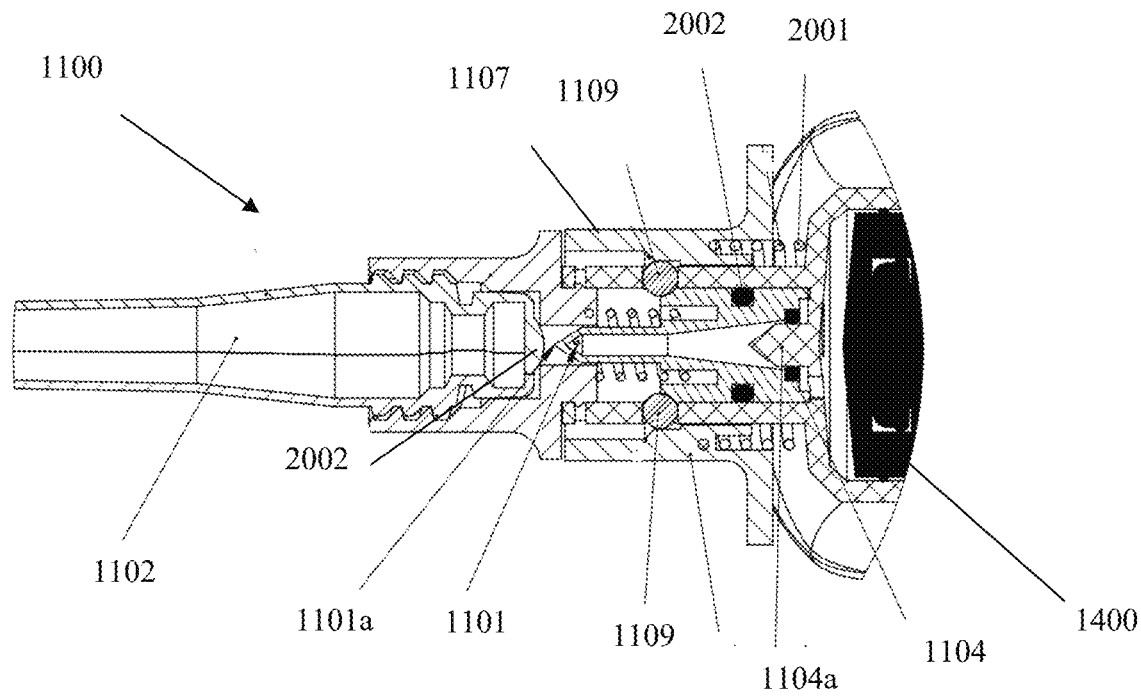
FIGS. 39a-39b illustrate another embodiment of the present invention in which a multi-use device is utilized.
Figure 39B:
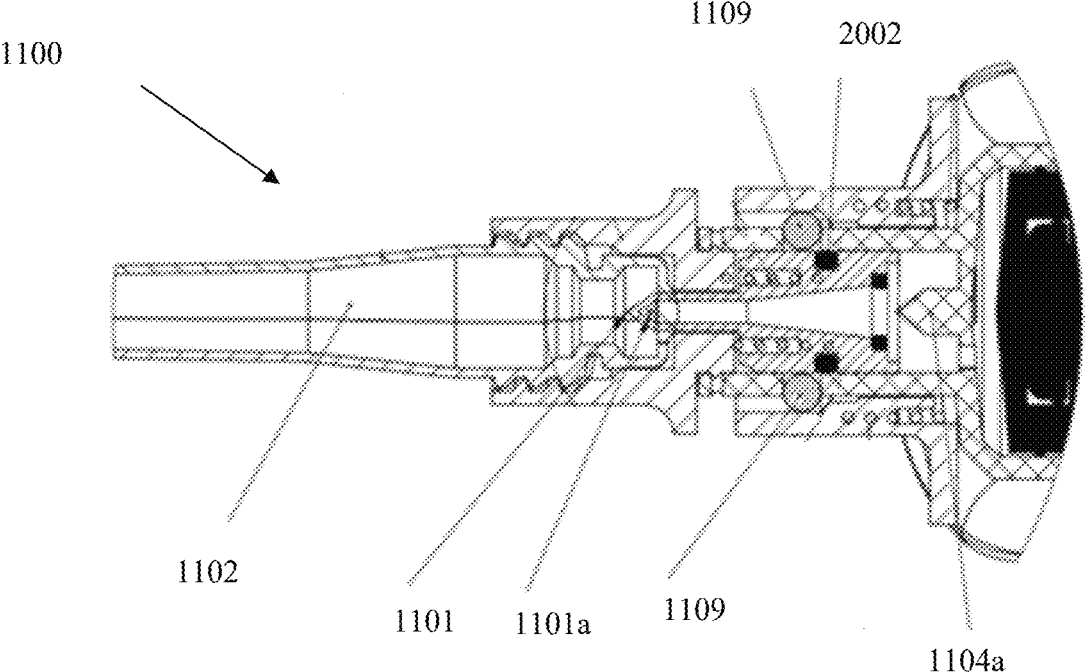

Reference is now made to FIGS. 39a-39b, which illustrate another embodiment of the multi-use device.

According to this embodiment, the delivery end (nozzle or nosepiece) 1100 comprises two parts: (a) hollow piercing means 1101; and, (b) capsule (e.g., a blow-fill-seal) 1102 containing the medicament to be delivered.

It should be noted that the hollow piercing means 1101 comprises a sharp end 1101a adapted to pierce the capsule 1102. Said sharp end comprises at least one opening 1101a (throughout which the pressurized gas will enter into the capsule 1102).

The bottom most part of the piercing means 1101 is in physical contact with the upper most part 1104a of the pressurized air chamber and enables (along with at least one o-ring 1104, as will be disclosed hereinafter) the sealing of the same.

It should be noted that although part 1104a is shaped with a sharp end, the same is not mandatory.

The piercing means 1101 is in physical contact with at least one element (e.g., spherical element 1109) which prevents the piercing means 1101 from being displaced and piercing the capsule 1102 (e.g., the BFS).

It should be noted that according to this embodiment, the delivery end (nozzle or nosepiece) 1100 has an expanded area 1106 (into which the spherical element 1109 will be displaced, once the device is activated, as will be disclosed hereinafter).

As described above, the handle 4 (or the single side lever 1620) is rotated from the parallel position (FIGS. 11A, 11C) to the perpendicular position (FIGS. 11B, 11D), the same pulls the plunger head away from the delivery end (1100) and filling the chamber (1400) with gas. The handle is then rotated back to the parallel position (FIGS. 11A, 11C), compressing the gas and transforming the device (1000) into the activated configuration. The device can then be activated and release the compressed and pressurized gas (along with the medicament) to the nasal cavity.

Thus, after the handle (4) is rotated back to the parallel position (to compress the gas inside the chamber), the pressure rises inside said chamber. In this position the device is ready to be activated.

Reference is now made to FIG. 39b illustrating the activation of the device. Activating the device is performed by pressing activation button (an activator, an actuator) 1107 downwardly (see FIG. 39b) by the air of spring 2001. Once pressed, the spherical element 1109 is moved to a position in the expanded area 1106, thus allowing the piercing means 1101 (namely, needle) to pierce capsule (e.g., a blow-fill-seal) 1102.

In parallel, when the device is activated, the o-ring 1104 sealing the at least one opening 1103 is moved, thus, allowing the pressurized gas being held in the chamber to exit the same, enter into the hollow the piercing means 1101 and exit from 1101a into the capsule 1102, entraining the medicament (held therewithin) and therefrom to the nasal cavity.

It should be noted that according to one embodiment of the present invention, a second O-ring, 2002, is provided. O-ring 2002 prevents any pressurized air from the compressed gas chamber 1400 to escape through the sideways and ensure all air will flow to the opening 1001a of the piercing means 1101 to capsule 1102.

Figures 40A, 40B:
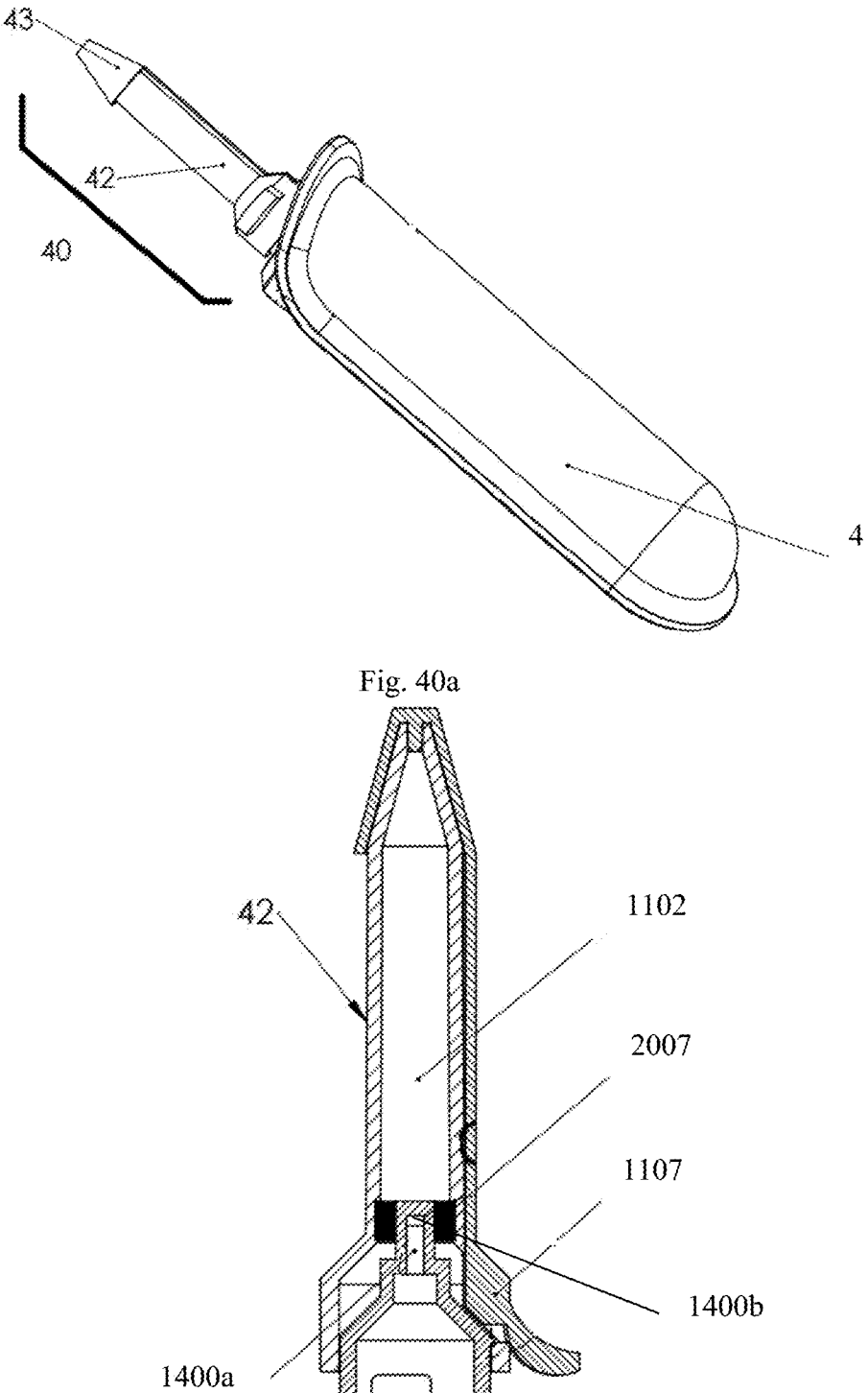
FIGS. 40a, 40b and 40c illustrate another embodiment of the present invention in which a multi-use device is utilized.
Figure 40C:
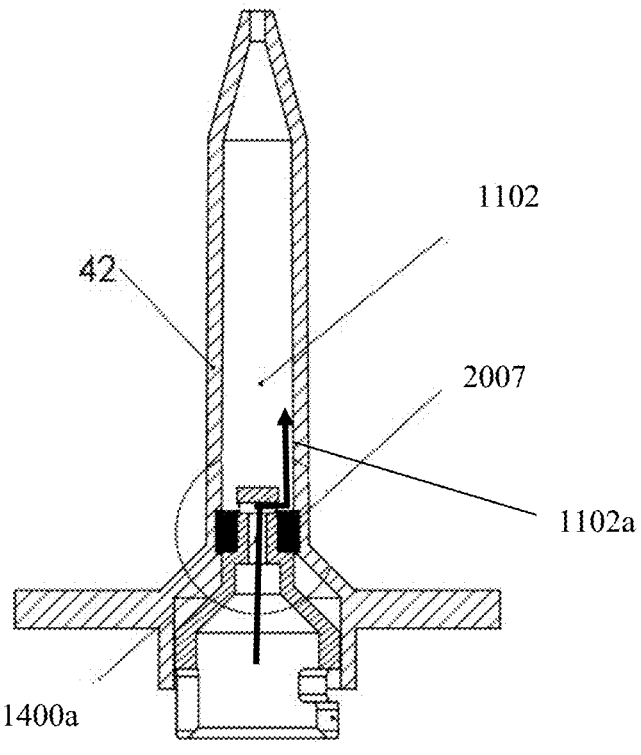

Reference is now made to FIGS. 40a-40c which illustrate another embodiment of the multi-use device, which utilize a luer lock valve.

Reference is now made to FIG. 40a which illustrates the multi-use device, the handle 4 as well as the delivery end (the nosepiece) 40. The delivery end 40 comprises the nosepiece 43 (insertable into the nasal cavity) and the capsule position 42. Nosepiece 43 comprises at least one opening throughout which the drug enclosed within capsule 42 is dispensed into the nasal cavity.

Reference is now made to FIGS. 40b-40c, illustrating only the upper part of the device, the delivery end 40. At least one groove 1401 is provided at the bottom most part of the delivery end which facilitates the coupling thereof to the compressed gas chamber 1400 (not shown in the Figs.).

According to this embodiment, a luer lock valve 1400a is integrated. The luer lock valve 1400a is in communication with the compressed gas chamber 1400 and activation thereof is enabled by activation handle 4. Also illustrated in the Fig. is a safety cover 1107, covering the nosepiece 43, adapted to prevent any accidental activation of the device. Only after safety cover 1107 is removed, the device is operable and can be activated.

Reference is now made to FIG. 40b, illustrating the luer lock valve 1400a prior to activation, thus, preventing the compressed air to exit the compressed gas chamber 1400 and entering the capsule 1102.

As can be appreciated by one of ordinary skills in the art, the luer lock valve comprises stem of a male luer 1400a having at least one opening 1400b at the end thereof. O-ring 2007 ensures the air-tight closure of said opening 1400b of the luer lock 1400a.

Figure 41A:
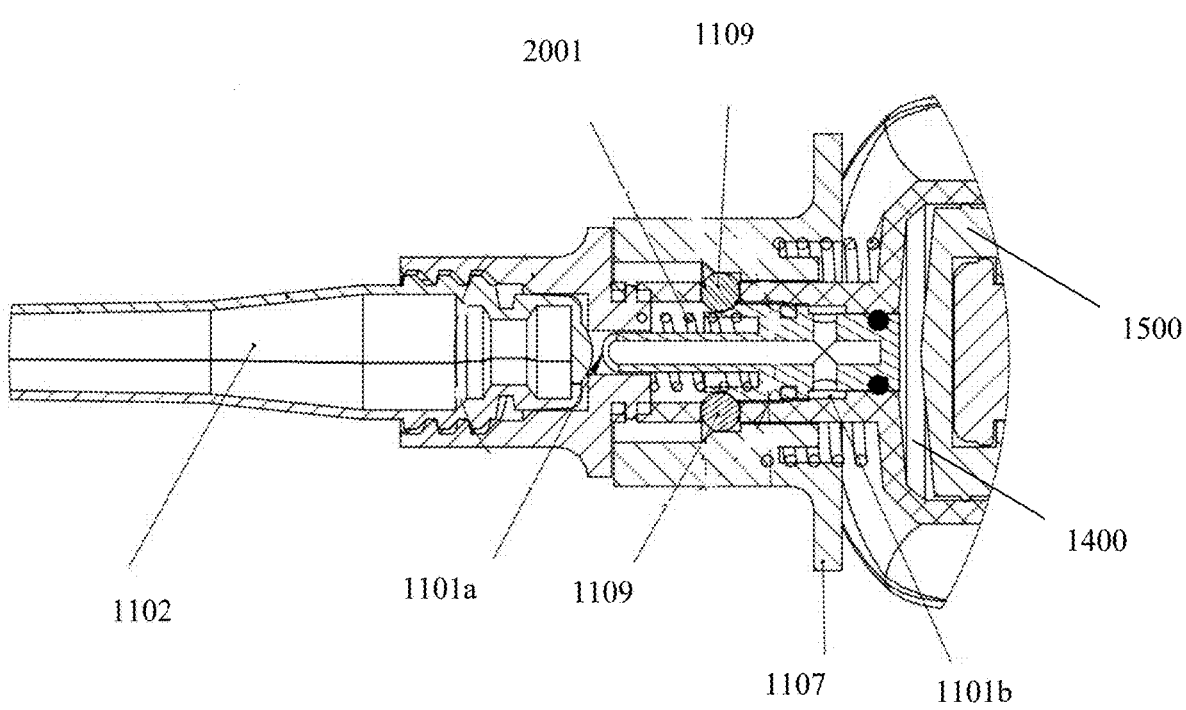
FIGS. 41a, 41b, 41c and 41d illustrate another embodiment of the present invention in which a multi-use device is utilized.
Figure 41B:
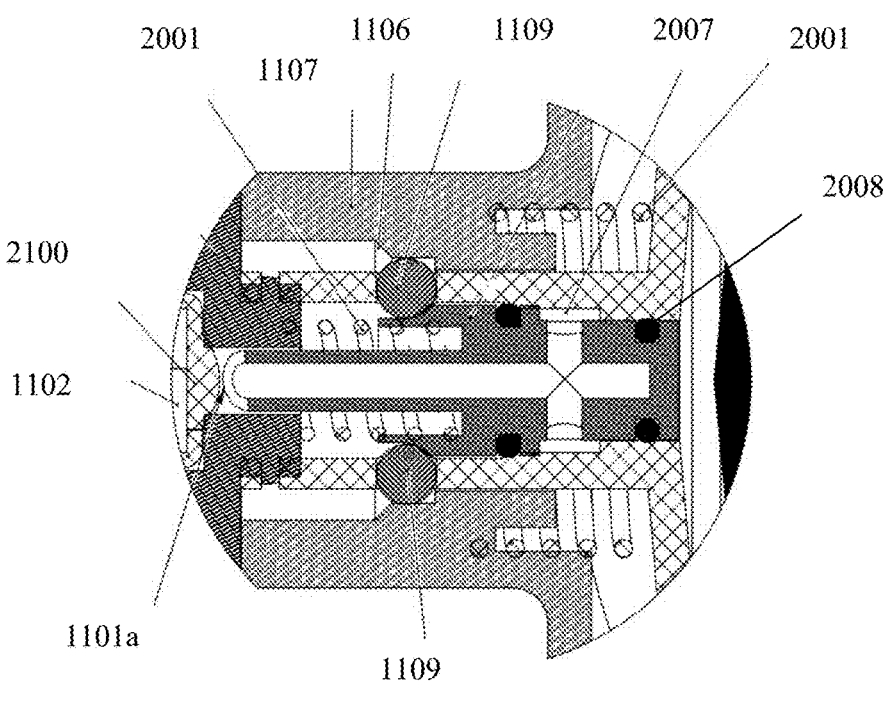
Figures 41C, 41D:
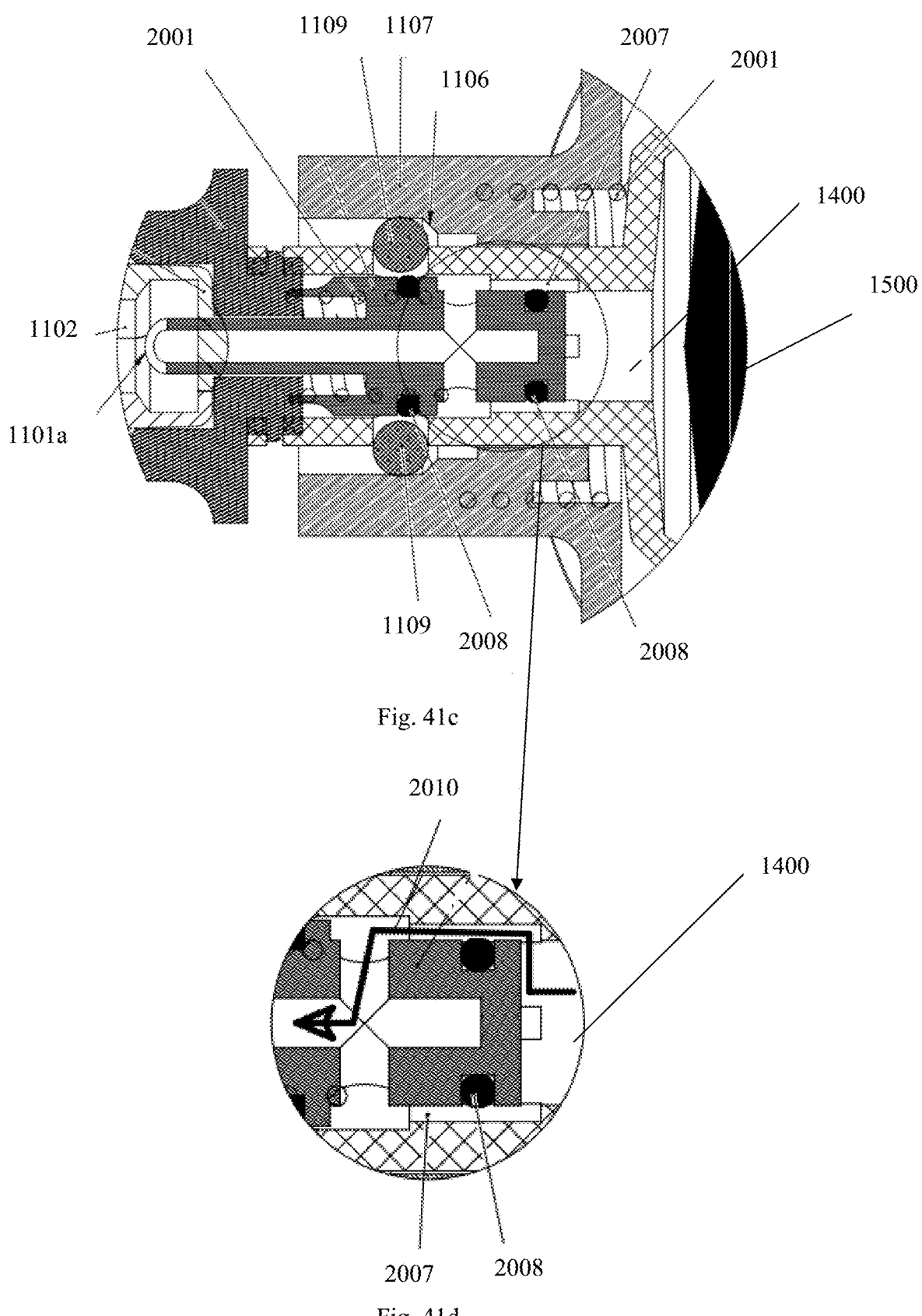

Reference is now made to FIG. 40c illustrating the device post activation (i.e., after air has been compressed into the compressed gas chamber 1400 by means of handle 4), thus, enabling the compressed air to exit the compressed gas chamber 1400 and enter the capsule 1102. The air traveling path is illustrated in arrow 1102a. Reference is now made to FIGS. 41a-41c which illustrate another embodiment of the multi-use device.

According to this embodiment, the piercing element (piercer) 1101 comprises two ends; upper most end 1101a, adapted to pierce the capsule 1102 (e.g., BFS) and bottom most end 1101b, being in fluid communication with the compressed gas chamber 1400 by means of at least one tube 2007.

Prior to activation said side tube is sealed by means of at least one o-ring 2008 (see FIGS. 41a-41b).

Reference is now made to FIGS. 41*c*-41*d* illustrating the device post activation, where FIG. 31*d* illustrates a closer view of the same.

As can be seen in the Figs. once the device is activated (activation handle 1107 is pressed towards the compressed gas chamber), spherical elements 1109 are moved to the extended area 1106, enabling the move of o-ring 2008 upwardly, and uncovering at least a portion of tube 2007 to be in fluid communication with the compressed gas chamber 1400.

The air flow from the compressed gas chamber 1400 into the piercing element 1101 is illustrated in arrow 2010 in FIG. 41*d*.

Figure 42A:
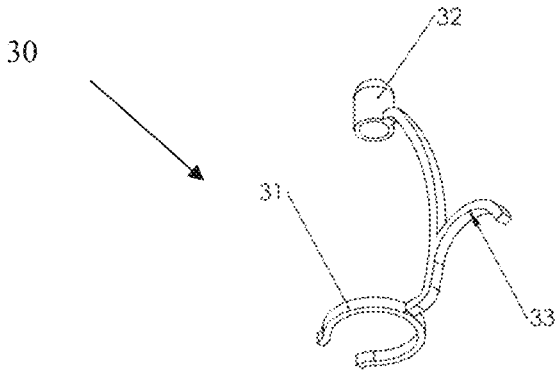
FIGS. 42a-42b illustrate another embodiment of the present invention in which a safe lock is utilized.
Figure 42B:
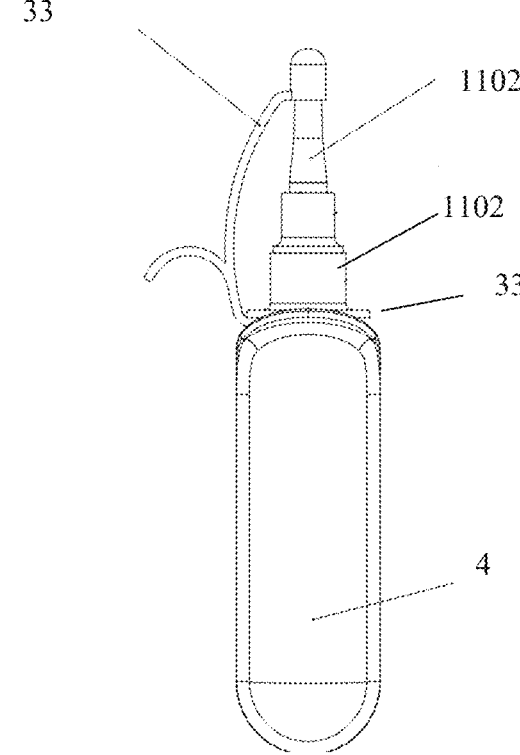

Reference is now made to FIGS. 42*a*-42*b*, illustrating another embodiment of the preset invention in which a safe lock 30 is provided.

The safe lock 30 is provided so as to prevent accidental activation of the device.

The safe lock comprises a nose cover 32 (place on top of the nosepiece), a handle 33 enabling the easy removal of the safe lock and a body part 31 adapted to be placed just below the activation handle 1107. Thus, the safe lock prevents the same from being pulled downwardly (towards the compressed gas container 1400) and, thus, accidentally activating the device.

Although certain embodiments have been illustrated and described herein, it will be appreciated by those of ordinary skill in the art that a wide variety of alternative or equivalent embodiments or implementations, calculated to achieve the same or similar purposes, may be substituted for the embodiments illustrated and described herein without departing from the scope of the present invention. Those of skill in the art will readily appreciate that embodiments in accordance with the present invention may be implemented in a very wide variety of ways. This application is intended to cover any and all adaptations and/or variations of the embodiments discussed herein.

The terms and expressions which have been employed in the foregoing specification are used therein as terms of description and not of limitation, and there is no intention, in the use of such terms and expressions, to exclude equivalents of the features shown and/or described or portions thereof, it being recognized that the scope of the invention is defined and limited only by the claims that follow.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

The invention claimed is:

1. A multi-use device for delivering a predetermined amount of at least one substance to a body orifice of a subject, said device characterized by a main longitudinal axis; said device comprising:

a. a container for containing said at least one substance;

b. a delivery end for placement in proximity to said orifice, said delivery end being in fluid communication with said container;

c. a valve mechanically connectable to said container, characterized by at least two configurations: (i) an ACTIVE CONFIGURATION in which said valve enables delivery of predetermined amount of said substance from said container to said body orifice via said delivery end; and, (ii) an INACTIVE CONFIGURATION, in which said valve prevents delivery of said predetermined amount of said substance from said container to said body orifice;

d. a fluid tight chamber adapted to contain predetermined amount of pressurized gas at a predetermined pressure; and e. at least one hollow piercing needle in communication with said valve, said fluid tight chamber and said container; said hollow piercing needle comprises at least one sharp end, adapted to pierce said container; said at least one hollow piercing needle comprising at least one opening, the at least one hollow piercing needle being disposed to contact and be positionally limited by a movable spherical element disposed within the delivery end, the spherical element being disposed radially outward from the at least one hollow piercing needle, and wherein displacement of the spherical element from a first area to a second area within the delivery end facilitates piercing by the at least one hollow piercing needle of said container, the second area being larger than the first area;

wherein once said valve is reconfigured from said INACTIVE CONFIGURATION to said ACTIVE CONFIGURATION, said at least one hollow piercing needle pierces said container;

further wherein said valve is structured such that pressurized gas, once said valve is reconfigured from said INACTIVE CONFIGURATION to said ACTIVE CONFIGURATION, exits said fluid tight chamber, enter said hollow piercing needle and therefrom, through said at least one opening, into said container and entrain said substance and deliver the same via said delivery end to a predetermined site of delivery within said body orifice.

2. The device of claim 1, additionally comprising a charger adapted to reversibly move a piston within said fluid tight chamber by a predetermined amount, said movement of said piston adapted to pressurize said gas.

3. The device of claim 2, wherein said charger comprises a member of a group consisting of: a handle rotatable about an axis perpendicular to said main longitudinal axis; two levers, wherein the levers are configured to be counter-rotating in a plane comprising said levers and said main longitudinal axis; a single side lever rotatable about an axis perpendicular to said main longitudinal axis; a rotable plunger rotatable about said main longitudinal axis and movable along said main longitudinal axis by a screw mechanism; a rotatable plunger rotatable about said main longitudinal axis and movable along said main longitudinal axis by a spring mechanism; a rotatable wheel rotatable about an axis perpendicular to said main longitudinal axis and adapted to move said plunger along said main longitudinal axis by a screw mechanism, a ratchet mechanism adapted to cause movement of a plunger along said main longitudinal axis, and any combination thereof.

4. The device of claim 2, additionally comprising a mouthpiece connected to said charger; further wherein at least one of the following is being held true (a) said mouthpiece is connected to an activation mechanism; further wherein, upon activation, said activation mechanism is configured to entrain said substance within said pressurized and predetermined amount of compressed gas and to deliver the same to said nasal passages; (b) said activation is by means of application of suction to the same through said mouthpiece; (c) said mouthpiece is adapted such that suction on said mouthpiece ensures closure of the mouth; (d) said closure of said mouth increases suction on said gas entering said nostril from said device; and combination thereof.

5. The device of claim 4, wherein said activation mechanism comprises a triggering means adapted to initiate delivery of said substance to said orifice, said means selected from a group consisting of: a luer lock valve, a releasable catch, a pressable button, a detectable predetermined sound pattern, a detectable predetermined light pattern, a moveable lever, a slider moveable from a first position to a second position, a rotatable knob, a releasable latch and any combination thereof; further wherein at least one of the following is being held true: (a) said predetermined sound pattern is selected from a group consisting of: a constant-pitch sound, a varying-pitch sound, a constant volume sound, a varying volume sound and any combination thereof; (b) said predetermined light pattern is selected from a group consisting of: a constant-color light, a varying-color light, a constant brightness light, a varying brightness light and any combination thereof; and any combination thereof.

6. The device of claim 2, wherein at least one of the following is being held true (a) juxtaposition of said delivery end with said orifice can be in a manner selected from a group consisting of sealingly emplaced within said orifice, sealingly emplaced against the opening of said orifice, loosely emplaced within said orifice, loosely emplaced against the opening of said orifice, emplaced against a portion of said orifice and any combination thereof; (b) said charger comprises a filter, said filter adapted to remove from the gas at least one selected from a group consisting of particulates, bacteria, viruses, moisture, and undesired particles; (c) said device comprises a unidirectional valve such that gas is enabled to flow from said charger to said delivery end, but is unable to flow in the reverse direction; (d) additionally comprising indicating means adapted to provide an indication to the user if at least one of the following is being held true (i) said entrainment of said substance within said enclosed air; (ii) transport of the same from said container to said nasal passages has been successful; or (iii) said predetermined amount pressurized gas is at said predetermined pressure; further wherein said indication is visible by means of a change of color, audible by means of a predetermined sound pattern and any combination thereof; (e) said pressurized and predetermined amount of compressed gas is inert and will not react with said substance; (f) said device can be configured into at least two states: (i) a loaded state wherein said chamber contains said predetermined amount of pressurized gas and said valve is in said INACTIVE configuration, and (ii) an activated state wherein said valve is in said ACTIVE configuration; and any combination thereof.

7. The device of claim 1, wherein said container is selected from a group consisting of a pierceable container, a blow-fill-seal and a form-fill-seal and any combination thereof.

8. The device of claim 1, wherein said container is a capsule having a main longitudinal axis, said capsule comprising at least one compartment, said at least one compartment adapted to contain said at least one substance.

9. The device of claim 8, wherein during dispensing of said at least one substance, said gas passing through said capsule entrains said at least one substance contained within said at least one compartment such that said at least one substance has a predetermined distribution within a resulting dispensed mixture, the mixture comprising the at least one substance and the gas; further wherein said predetermined distribution comprises an aerosol; further wherein characteristics of said aerosol selected from a group consisting of: particle size, particle shape, particle distribution, and any combination thereof, are determinable from characteristics of said device selected from a group consisting of: a predetermined volume of said gas, a predetermined pressure of said gas, a predetermined size of an orifice of said delivery end, and any combination thereof.

10. The device of claim 8, wherein at least one of the following is being held true (a) the shape of said capsule is selected from a group consisting of: cylindrical, spherical, elliptical, ovoid, pillow-shaped, football-shaped, stellate and any combination thereof; (b) the disposition of the main longitudinal axis of at least one of said at least one compartment is selected from a group consisting of: parallel to the main longitudinal axis of the capsule, spirally disposed with respect to the main longitudinal axis of the capsule, an angle to the main longitudinal axis of the capsule, and any combination thereof; and any combination thereof.

11. The device of claim 10, wherein at least one of the following is being held true (a) said capsule has cross-section selected from a group consisting of: circular, oval, elliptical, lenticular, regular polygonal having has n sides, n is an integer greater than 2, irregular polygonal and any combination thereof; (b) at least one of the shape and size of the cross-section of said capsule is selected from a group consisting of: substantially constant along said capsule's main longitudinal axis, changes along said capsule's main longitudinal axis, and any combination thereof.

12. The device of claim 10, additionally comprising at least one mixing mechanism adapted to perform at least one of a group consisting of: entrain said at least one substance into said gas, mix said at least one substance, react said at least one substance, and any combination thereof.

13. The device of claim 12, wherein said mixing mechanism comprises at least one fluid channel in fluid communication with said at least one compartment, said fluid channel is disposed in said mixing mechanism in a manner selected from a group consisting of: spirally, with the axis of said spiral substantially parallel to said main longitudinal axis of said container; linearly, with the line substantially parallel to the main longitudinal axis of said container; linearly, with the line at an angle to the main longitudinal axis of said container; with the center of the cross-section of said channel forming a curve; and any combination thereof.

14. The device of claim 12, wherein said mixing mechanism comprises a plurality of mixing regions in fluid communication with each other, said plurality of mixing regions being disposed longitudinally along said main longitudinal axis of said container, each said mixing region of the plurality of mixing regions comprising at least one fluid channel.

15. The device of claim 14, wherein at least one of the following is true:
   a. in at least one of said plurality of mixing regions, said at least one fluid channel has a diameter substantially equal to the diameter of the interior of said container;
   b. said at least one fluid channel is disposed in said corresponding mixing region in a manner selected from a group consisting of: spirally, with the axis of said spiral substantially parallel to said main longitudinal axis of said container; linearly, with the line substantially parallel to the main longitudinal axis of said container; linearly, with the line at an angle to the main longitudinal axis of said container; with the center of the cross-section of said channel forming a curve; and any combination thereof; and c. the disposition of said at least one fluid channels selected from a group consisting of: the same in at least two mixing regions, differs in at least two mixing regions, and any combination thereof.

16. The device of claim 12, wherein said mixing mechanism is at least partially within said container.

17. The device of claim 12, wherein at least one of the following is being held true (a) said container is placeable in fluid connection with said device; (b) said substance is selected from a group consisting of a gas, a liquid, a powder, an aerosol, a slurry, a gel, a suspension and any combination thereof; (c) said container is either a capsule removably containable within said delivery device or is comprised within said delivery device; (d) either said container contains a single dose of said at least one substance or a plurality of said containers comprise a cartridge, said containers being independently openable, each of said independently-openable containers comprising a member of a group selected from (i) a single dose of said at least one substance, (ii) multiple doses of said at least one substance, (iii) different substances, (iv) carrier, (v) gas and (vi) any combination thereof; and any combination thereof; (e) said device further comprising a filter, said filter upstream of said at least one substance, said filter adapted to remove from the carrier gas at least one selected from a group consisting of particulates, bacteria, viruses, moisture, and undesired particles; (f) said at least one compartment and said mixing mechanism comprise separable units; (g) at least one said substance is stored under either an inert atmosphere or under vacuum to prevent reactions during storage; and any combination thereof.

18. The device of claim 17, wherein said at least one compartment comprises at least two compartments separated by a frangible membrane; further wherein at least one of the following is being held true: (a) said container is adapted such that rupture of said frangible membrane enables at least one of mixing and reaction of at least two of said substances; (b) said at least one of mixing and reaction of said at least two of said substances occurs in an order selected from a group consisting of sequentially, simultaneously, and any combination thereof; (c) components of said substance can arrive at a deposition site simultaneously, sequentially, and any combination thereof; and any combination thereof.

19. The device of claim 1, wherein said gas comprises air, nitrogen, oxygen, carbon dioxide, helium, neon and xenon and any combination thereof.

20. The device of claim 1, wherein said container comprises a port fluidly connectable to the exterior of said device, said port adapted to such that a substance is insertable into said chamber via said port.

21. The device of claim 20, wherein said device comprises a port cover adapted to provide an air-tight closure for said port, said port cover slidable along said device, rotatable around said device, rotatable around a hinge on the exterior of said device and any combination thereof.

22. The device of claim 1, wherein said at least one substance is selected from a group consisting of: a composition, a gas, an inert gas, and any combination thereof; further wherein at least one of the following is being held true: (a) said composition comprises a member of a group consisting of: a drug, a medicament, a chemical permeation enhancer, a mucoadhesive agent, a purified natural biologic, a synthetic biologic, a carrier, a filler, a bulking agent, an inert material, a flavoring material, an odorizing material, an excipient and any combination thereof; (b) said mucoadhesive agent is selected from a group consisting of: a bioadhesive protein, a carbohydrate, a mucoadhesive polymer and any combination thereof; (c) said medicament is selected from a group consisting of saline, natural substances, medicaments for treatments for allergic rhinitis, medicaments for treatments for osteoporosis, vaccinations and immunizations, sexual dysfunction drugs, medicaments for treatments for B12 deficiency, medicaments for smoking cessation, medicaments for treatment of gynecological problems, medicaments for treatment of other women's health issues, medicaments for general anesthetics, local anesthetics, opioid analgesics, agonist-antagonists and antagonists, antitussives, medicaments for treatment of motor disorders, antiepileptics, antipsychotics (neuroleptics), sedative-hypnotics, anxiolytics, and centrally acting muscle relaxants, medicaments for treatments for anxiety disorders, skeletal muscle relaxants, medicaments for treatments for Parkinson's disease, medicaments for treatments for Alzheimer's disease, medicaments for treatment of allergic rhinitis, steroids, corticosteroids, Flonase, Patanase, Beconase, Antihistamine, Astelin, Otrivin, Livostin, Theramax, Avamys, Lufeel, Sinofresh, Nasonex, Nasocort, Veramyst, medicaments for treatment of osteoporosis, Miacalcin, Fortical and Stadol, medicaments for vaccinations and immunizations, LAVIN, and influenza vaccines including FluMist, NasalFent, Calcitonin, parathyroid hormone, Neurotransmitters and neuromodulators, acetylcholine (ACH), Anticholinergic drugs, adenosine triphosphate (ATP), aspartate (Asp), beta-amyloid, beta-endorphin, bradykinin, dopamine (DA), L-DOPA, Carbio-Dopa, epinephrine, dynorphins, endomorphins, enkephalins, 5-hydroxytryptamine (5-HT), Sumatriptan, Imitrex, Migranal, Zolmitriptan, Zomig, Gamma-aminobutyric acid (GABA), glutamate (glu), glycine, histamine, leptin, nerve growth factor and other growth factors, norepinephrine, nitric oxide, Substance P, alfentanil, desflurane, enflurane, etomidate, fentanyl, halothane, isoflurane, ketamine, methohexital, methoxyflurane, midazolam, morphine, nitrous oxide (N2O), propofol, sevoflurane, Sufentanil, Sublimase, thiopental, benzocaine, bupivacaine, cocaine, lidocaine, prilocaine, procaine, ropivacaine, tetracaine, Opioid analgesics, agonist-antagonists, and antitussives, agonists, codeine, diphenoxylate, fentanyl, heroin and other opiods, hydrocodone, 1-alpha-acetyl-methadol, levomethadyl acetate, loperamide, meperidine, methadone, morphine, oxycodone, d-propoxyphene, combinations of opioids plus acetaminophen and asa, and tramadol, agonist/antagonists and antagonists, buprenorphine, butorphanol, nalbuphine, nalorphine, naloxone, naltrexone, nalmefene, pentazocine, codeine, dextromethorphan, and hydrocodone, medicaments for treatment of Parkinson's disease and motor disorders, amantadine, apomorphin, baclofen, benzodiazepines, benztropine, bromocriptine, carbidopa, cyclobenzaprine, dantrolene, dopamine, entacapone, haloperidol, pergolide, pramiprexole, ropinerole, selegiline (deprenyl), trihexyphenidyl, rasagiline, azilect, selegiline, ladostigil, rotigotine, neupro, mono amine oxidase inhibitor, COMT inhibitor, antiepileptics, acetazolamide, carbamazepine, clonazepam, diazepam, ethosuximide, felbamate, gabapentin, Lamotrigine, lorazepam, phenobarbital, phenytoin, primidone, tiagabine, topiramate, valproic acid, Vigabatrin, Midazolam, antidepressants, amitriptyline, bupropion, citalopram, clomipramine, desipramine, fluoxetine, fluvoxamine, imipramine, nortriptyline, paroxetine, phenelzine, sertraline, trazodone, tranylcypromine, venlafaxine, antimanic drugs, carbamazepine, lithium carbonate valproic acid, antipsychotics (neuroleptics), chlorpromazine (CPZ), clozapine, fluphenazine, haloperidol, olanzapine, quetiapine, risperidone, sertindole, thioridazine, thiothixene, ziprasidone, sedative-hypnotics, anxiolytics, and centrally acting muscle relaxants, alprazolam, chloral hydrate, diphenhydramine, flumazenil, flurazepam, hydroxyzine, lorazepam, oxazepam, phenobarbital, temazepam, triazolam, zaleplon, zolpidem, anxiety disorders and skeletal muscle relaxants, alprazolam, chlorazepate, chlordiazepoxide, diazepam, flumazenil (antagonist), amphetamine, caffeine, ephedrine, methamphetamine, methylphenidate, phentermine, sibutramine, disulfiram, ethanol, methanol, naltrexone, atropine, scopolamine, ketamine, lysergic acid diethylamide (LSD), MDMA (methylene dioxy-methyl amphetamine), mescaline, phencyclidine (PCP), donabinol, marijuana/THC, organic solvents, nicotine, Pentobarbital, neuroprotective compounds, neuroprotective peptides, neuroprotective factors, davunetide, anti schizophrenic drugs, anti depression drugs, comtan, Entacopone, anti ADHD agents, and anti ADHD drugs as Methylphenidate (ritalin), anti-autism and anti-autism symptoms drugs, medicaments for treatment of Alzheimer's disease, donepezil, galantamine, rivastigmine, Tacrine, insulin, NPH Insulin, Lispro, Aspart, Detemir Insulin, Glulisin, Glargin Insulin, Insulin degludec, Detemir, Novolin, Humulin, insulin, insulin like hormone, BDNF, GDNF, MIBG, anti cancer agents, anti cancer drugs, dopamine agonist, dopamine antagonist, a peptide, a protein, an antibody, nucleic acid, a small molecule, a cell, part of a cell, a stem cell, a nanoparticle, a microparticle, a nanoscale particle, a microscale particle, a purified natural biologic, a synthetic biologic and any combination thereof; (d) a penetration enhancer selected from a group consisting of: Hyaluronic acid, a fatty acid, a medium chain glyceride, a surfactant, a steroidal detergent, an acyl carnitine, Lauroyl-DL-carnitine, an alkanoyl choline, an N-acetylated amino acid, an ester, a sodium salt, a nitrogen-containing ring, a derivative of a nitrogen-containing ring, sodium lauryl sulfate, sodium decyl sulfate, sodium octyl sulfate, N-lauryl sarcosinate, sodium carparate, Cetyltrimethyl ammonium bromide, decyltrimethyl ammonium bromide, benzyldimethyl dodecyl ammonium chloride, myristyltimethyl ammonio chloride, deodecyl pridinium chloride, decyldimethyl ammonio propane sulfonate, palmityldimethyl ammonio propane sulfonate, butyric acid, caproic acid, caprylic acid, pelargonic acid, capric acid, lauric acid, myristic acid, palmitic acid, stearic acid, arachidic acid, oleic acid, linoleic acid, linolinic acid, a butyric acid salt, a caproic acid salt, a caprylic acid salt, a pelargonic acid salt, a capric acid salt, a lauric acid salt, a myristic acid salt, a palmitic acid salt, a stearic acid salt, an arachidic acid salt, an oleic acid salt, a linoleic acid salt, a linolinic acid salt, a butyric acid derivative, a caproic acid derivative, a caprylic acid derivative, a pelargonic acid derivative, a capric acid derivative, a lauric acid derivative, a myristic acid derivative, a palmitic acid derivative, a stearic acid derivative, an arachidic acid derivative, an oleic acid derivative, a linoleic acid derivative, a linolinic acid derivative, a butyric glyceride, a caproic glyceride, a caprylic glyceride, a pelargonic glyceride, a capric glyceride, a lauric glyceride, a myristic glyceride, a palmitic glyceride, a stearic glyceride, an arachidic glyceride, an oleic glyceride, a linoleic glyceride, a linolinic glyceride, a butyric monoglyceride, a caproic monoglyceride, a caprylic monoglyceride, a pelargonic monoglyceride, a capric monoglyceride, a lauric monoglyceride, a myristic monoglyceride, a palmitic monoglyceride, a stearic monoglyceride, an arachidic monoglyceride, an oleic monoglyceride, a linoleic monoglyceride, a linolinic monoglyceride, a butyric diglyceride, a caproic diglyceride, a caprylic diglyceride, a pelargonic diglyceride, a capric diglyceride, a lauric diglyceride, a myristic diglyceride, a palmitic diglyceride, a stearic diglyceride, an arachidic diglyceride, an oleic diglyceride, a linoleic diglyceride, a linolinic diglyceride, a butyric triglyceride, a caproic triglyceride, a caprylic triglyceride, a pelargonic triglyceride, a capric triglyceride, a lauric triglyceride, a myristic triglyceride, a palmitic triglyceride, a stearic triglyceride, an arachidic triglyceride, an oleic triglyceride, a linoleic triglyceride, a linolinic triglyceride, cholate, deoxycholate, tauro-cholate, glycocholate, taurodexycholate, ursodeoxycholate, tauroursodeoxycholate, chenodeoxycholate, EDTA, EGTA, sodium dodecyl sulfate, a polyethylene ether, a polyethylene ester, polyethylene glycol-12 lauryl ether, salicylate polysorbate 80, nonylphenoxypolyoxyethylene, dioctyl sodium sulfosuccinate, saponin, palmitoyl carnitine, lauroyl-l-carnitine, dodecyl maltoside, acyl carnitines, alkanoyl cjolline, 3-nitrobenzoate, zoonula occulden toxin, fatty acid ester of lactic acid salts, glycyrrhizic acid salt, hydroxyl beta-cyclodextrin, sodium N-[8-(2-hydroxybenzoyl)amino]caprylate, chitosan salts and derivatives, a zwitterionic surfactant, palmityl dimethyl ammonio propane sulfonate (PPS) or a structural analog thereof, a nonionic surfactant, polysorbate 20, polysorbate 40, polysorbate 60, or polysorbate 80 and any combinations thereof; (e) said odorant is selected from a group consisting of: Geranyl Acetate, Ethyl Acetate, Benzyl Acetate, Octyl Acetate, Geraniol, Citral, Citronella, Nerolidol, Terpineol, Thujone, Eugenol, Vanillin, Anisole, Thymol, Indole, aromatic compounds of Alcohols, aromatic compounds of Aldehydes, aromatic compounds of Esters, aromatic compounds of Ketones, aromatic compounds of Lactones, aromatic compounds of Thiols and any combination thereof; (f) said composition comprising said at least one chemical permeation enhancer has increased rate of absorption of at least one said drug at said site of delivery, relative to rate of absorption of said at least one drug at said site in a composition lacking said at least one chemical permeation enhancer; (g) wherein said composition comprising said at least one chemical permeation enhancer is adapted to be unable to cause either necrosis or specific inflammation at said site of delivery; (h) said composition comprising said at least one chemical permeation enhancer is adapted to be unable to cause at least one symptom associated with malfunctions of the gastrointestinal tract; (i) the composition is in a form selected from a group consisting of a gel, a solution, a cream, a spray, a powder, a tablet and any combination thereof; (j) at least one said chemical permeation enhancer is adapted to deliver drugs into epithelial cells; and any combination thereof.

23. The device of claim 1, wherein at least one of the following is being held true (a) said site of delivery is in a mucosal layer selected from a group consisting of mucosa of the intestine, mucosa of the colon, mucosa of the oral cavity and mucosa of the nasal cavity; (b) from said active configuration, said predetermined amount of gas is deliverable from said chamber to said body orifice, said body orifice is selected from a group consisting of: at least one nostril, the mouth, the throat, an ear, the vagina, the rectum, the urethra, and any combination thereof; (c) said substance is deliverable to a member selected from a group consisting of respiratory epithelium, olfactory epithelium, lower turbinates, middle turbinates, upper turbinates, ethmoid bone, brain, lungs, pharynx, blood and any combination thereof through said nasal passages; (d) said device is in said activated state, the predetermined volume of said gas is in the range of about 0.1 to about 50 ml and the predetermined pressure of said gas is in the range of about 1 to about 20 bar; and any combination thereof.

24. The device of claim 1, wherein said delivery end (1100) comprises at least one expandable portion (1120).

25. The device of claim 24, wherein at least one of the following is being held true (a) said at least one expandable portion (1120) either completely surrounds said delivery end (1100) or partially surrounds said delivery end (1100); (b) at least one said expandable portion (1120) is inflatable; (c) at least one said expandable portion (1120), at such times as not expanded, is either storable within said device or is on the surface of said device; (d) at least one said expandable portion is inflatable either before or at the time of said activation of said device; (e) at least one said expandable portion is detachable from said device such that said detachable portion is adapted to seal said nasal passage after removal of said delivery end (1100) from said nasal passage; (f) said detachable portion, after detachment from said device, is adapted to be removable from said nasal passage; and any combination thereof.

26. A multi-use device for delivering a predetermined amount of at least one substance to a body orifice of a subject, said device characterized by a main longitudinal axis; said device comprising:

a. a container for containing said at least one substance;

b. a delivery end for placement in proximity to said orifice, said delivery end being in fluid communication with said container;

c. a valve mechanically connectable to said container, characterized by at least two configurations: (i) an ACTIVE CONFIGURATION in which said valve enables delivery of predetermined amount of said substance from said container to said body orifice via said delivery end; and, (ii) an INACTIVE CONFIGURATION, in which said valve prevents delivery of said predetermined amount of said substance from said container to said body orifice; said valve comprising at least one hollow element in communication with said fluid tight chamber and said container; said hollow element comprising at least one opening, being sealed with at least one sealing element, when said valve is in said INACTIVE CONFIGURATION;

wherein the at least one hollow element is disposed to contact and be positionally limited by a movable spherical element disposed within the delivery end, the spherical element being disposed radially outward from the at least one hollow element, and wherein displacement of the spherical element from a first area to a second area within the delivery end facilitates piercing by the at least one hollow element of said container, the second area being larger than the first area;

d. a fluid tight chamber adapted to contain predetermined amount of pressurized gas at a predetermined pressure;

wherein once said valve is reconfigured from said INACTIVE CONFIGURATION to said ACTIVE CONFIGURATION, said at least one sealing is removed from said at least one opening;

further wherein said pressurized gas, once said valve is reconfigured from said INACTIVE CONFIGURATION to said ACTIVE CONFIGURATION, is adapted to exit said fluid tight chamber, enter said hollow element and therefrom, through said at least one opening, into said container and entrain said substance and deliver the same via said delivery end to a predetermined site of delivery within said body orifice.

27. The multi-use device of claim 26, further comprising a charger adapted to reversibly move a piston within said fluid tight chamber by a predetermined amount, said movement of said piston adapted to pressurize said gas;

wherein the charger comprises two levers, the two levers configured to be counter-rotating in a plane comprising the two levers.

28. A method for dispensing a flowable substance, comprising steps of:

a. providing a multi-use device for delivering a predetermined amount of at least one substance to a body orifice of a subject, said device characterized by a main longitudinal axis; said device comprising:

i. a container for containing said at least one substance;

ii. a delivery end for placement in proximity to said orifice, said delivery end being in fluid communication with said container;

iii. a valve mechanically connectable to said container, characterized by at least two configurations: (i) an ACTIVE CONFIGURATION in which said valve enables delivery of predetermined amount of said substance from said container to said body orifice via said delivery end; and, (ii) an INACTIVE CONFIGURATION, in which said valve prevents delivery of said predetermined amount of said substance from said container to said body orifice;

iv. a fluid tight chamber adapted to contain predetermined amount of pressurized gas at a predetermined pressure;

V. at least one hollow piercing needle in communication with said valve, said fluid tight chamber and said container; said hollow piercing needle comprises at least one sharp end, adapted to pierce said container, and comprising at least one opening, the at least one hollow piercing needle being disposed to contact and be positionally limited by a movable spherical element disposed within the delivery end, the spherical element being disposed radially outward from the at least one hollow piercing needle, and wherein displacement of the spherical element from a first area to a second area within the delivery end facilitates piercing by the at least one hollow piercing needle of said container, the second area being larger than the first area;

b. emplacing said substance in said chamber;

c. placing said valve in said inactive configuration;

d. pressurizing said fluid-tight chamber with said gas to said predetermined pressure;

e. reconfiguring said valve from said INACTIVE CONFIGURATION to said ACTIVE CONFIGURATION; thereby piercing said container;

thereby enabling said pressurized gas to exit said fluid tight chamber, enter said hollow piercing needle and therefrom, through said at least one opening, into said container and entraining said substance and delivering the same via said delivery end to a predetermined site of delivery within said body.

* * * * *